US011158808B2

(12) United States Patent
Kim et al.

(10) Patent No.: US 11,158,808 B2
(45) **Date of Patent: *Oct. 26, 2021**

(54) ORGANIC LIGHT EMITTING DISPLAY DEVICE

(71) Applicants: LG Display Co., Ltd., Seoul (KR); LG Chem, Ltd., Seoul (KR)

(72) Inventors: Jungkeun Kim, Seoul (KR); Dohan Kim, Goyang-si (KR); Jeongdae Seo, Incheon (KR); Hyoseok Kim, Daejeon (KR); Heungwoo Choi, Daejeon (KR); Wanpyo Hong, Daejeon (KR)

(73) Assignees: LG Display Co., Ltd., Seoul (KR); LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/842,486

(22) Filed: Apr. 7, 2020

(65) Prior Publication Data

US 2020/0235302 A1 Jul. 23, 2020

Related U.S. Application Data

(63) Continuation of application No. 15/250,214, filed on Aug. 29, 2016, now Pat. No. 10,658,593.

(30) Foreign Application Priority Data

Dec. 3, 2015 (KR) ........................ 10-2015-0171452
May 10, 2016 (KR) ........................ 10-2016-0057107

(51) Int. Cl.
*H01L 51/00* (2006.01)
*H01L 51/52* (2006.01)
(Continued)

(52) U.S. Cl.
CPC ........ *H01L 51/0052* (2013.01); *C07C 255/47* (2013.01); *C07D 213/61* (2013.01);
(Continued)

(58) Field of Classification Search
CPC ... C07C 255/45; C07C 255/47; C07C 255/51; C07C 255/52; H01L 51/0052; H01L 51/5088; H01L 51/5058
See application file for complete search history.

(56) References Cited

U.S. PATENT DOCUMENTS

RE44,304 E * 6/2013 Marks ..................... C07C 45/46 549/59
2009/0091248 A1 4/2009 Kim et al.
(Continued)

FOREIGN PATENT DOCUMENTS

JP 2010-535270 A 11/2010
KR 10-2014-0085433 A 7/2014
(Continued)

OTHER PUBLICATIONS

Endo et al., "Synthesis and Electronic Structure of Dicyanofulvene-Fused Electron Accepting Molecule Based on a 1,5-Dihydro-s-Indacene Framework," Organic Letters, 16, 5608-5611 (2014).
(Continued)

*Primary Examiner* — Jennifer A Boyd
*Assistant Examiner* — Sean M DeGuire
(74) *Attorney, Agent, or Firm* — Morgan, Lewis & Bockius LLP

(57) ABSTRACT

An organic light emitting display device is provided. The organic light emitting display device may include at least one light emitting part between an anode and a cathode, and the at least one light emitting part having at least one organic
(Continued)

100 layer and a light emitting layer, wherein the at least one organic layer comprises a compound represented by Chemical Formula 1 or 2.

34 Claims, 3 Drawing Sheets

(51) Int. Cl.

| | |
|---|---|
| ***H01L 51/50*** | (2006.01) |
| ***C07C 255/47*** | (2006.01) |
| ***C07D 213/61*** | (2006.01) |
| ***C09K 11/06*** | (2006.01) |

(52) U.S. Cl.

CPC .......... *C09K 11/06* (2013.01); *H01L 51/0053* (2013.01); *H01L 51/0064* (2013.01); *H01L 51/0067* (2013.01); *H01L 51/5056* (2013.01); *H01L 51/5278* (2013.01); *C07C 2603/10* (2017.05); *C09K 2211/1007* (2013.01); *C09K 2211/1011* (2013.01); *C09K 2211/1029* (2013.01); *H01L 51/506* (2013.01); *H01L 51/5012* (2013.01); *H01L 51/5064* (2013.01); *H01L 51/5088* (2013.01); *H01L 51/5206* (2013.01); *H01L 51/5221* (2013.01)

(56) References Cited

U.S. PATENT DOCUMENTS

| | | | | |
|---|---|---|---|---|
| 2014/0117338 | A1* | 5/2014 | Cho | H01L 51/5044 257/40 |
| 2014/0167016 | A1 | 6/2014 | Yoo et al. | |
| 2014/0183493 | A1 | 7/2014 | Lee et al. | |
| 2019/0207123 | A1 | 7/2019 | Yoon et al. | |
| 2020/0303651 | A1 | 9/2020 | Kim et al. | |

FOREIGN PATENT DOCUMENTS

| | | | |
|---|---|---|---|
| WO | 2008/106210 | A1 | 9/2008 |
| WO | 2009/017798 | A1 | 2/2009 |
| WO | 2013/190427 | A1 | 12/2013 |

OTHER PUBLICATIONS

Chen et al., Synthesis, Optical and Electroluminescent Properties of a Novel Indacene, 2003, Synthetic Metals, 139:529-534.

Endo et al., Synthesis and Electronic Structure of Dicyanofulvene-Fused Electron Accepting Molecule Based on a 1,5-Dihydro-s-Indacene Framework, 2014, Org. Lett., 16:5608-5611.

Zhu et al., Modular Synthesis of 1H-Indenes, Dihydro-s-Indacene, and Diindenoindacene—a Carbon-Bridged p-Phenlylenevinylene Congener, 2009, J. American Chemical Society, 131:13596-13597.

Office Action issued in corresponding European Patent Application No. 16182682.1 dated Jun. 12, 2020.

* cited by examiner

ORGANIC LIGHT EMITTING DISPLAY DEVICE

CROSS-REFERENCE TO RELATED APPLICATIONS

This application is a continuation of U.S. patent application Ser. No. 15/250,214, filed on Aug. 29, 2016, which claims the priority benefit of Korean Patent Application Nos. 10-2015-0171452 filed on Dec. 3, 2015, and 10-2016-0057107 filed on May 10, 2016, the entire disclosure of which are all incorporated herein by reference for all purposes as if fully set forth herein.

BACKGROUND OF THE DISCLOSURE

Field of the Disclosure

The present disclosure relates to an organic light emitting display device, and more particularly, to an organic light emitting display device with reduced operating voltage and improved efficiency.

Discussion of the Related Art

Image displays used for displaying a variety of information m the screen are one of the core technologies of the information and communication era. Such image displays have been developed to be thinner, lighter, more portable, and to have high performance. With the development of the information society, various demands for display devices are m the rise. To meet these demands, research onpanel displays such as liquid crystal displays (LCD), plasma display panels (PDP), electroluminescent displays (ELD), field emission displays (FED), organic light emitting diodes (OLEO), etc. is actively under way.

Among these types of displays, the organic light emitting display devices are a type of devices that, when the charges are injected into an organic emissive layer formed between an anode and a cathode, the emission of light due to the formation of electron-hole pairs takes place and extinguishes. The organic light emitting display devices are advantageous in that they can be fabricated on a flexible transparent substrate such as plastic substrate, can be operated at a relatively low voltage, have less power consumption, and deliver vivid color reproduction, as compared with the plasma display panels or the inorganic light emitting displays. Particularly, the white OLED devices are used for various purposes in lighting, thin light sources, backlights for liquid crystal displays, or full-color displays employing color filters.

An organic light emitting display device has a lamination structure of an anode, a hole injection layer, a hole transport layer, an light emitting layer, an electron transport layer, an electron injection layer, and a cathode, and the hole injection layer and the electron injection layer are used to facilitate charge injection. A P-type hole injection layer, which is a type of hole injection layer, is involved in the generation, injection, and transport of holes. The P-type hole injection layer is a layer formed of a single P-type material, or includes a host and a P-type material therein. The host serves to inject holes from the anode into the light emitting layer through the HOMO (highest occupied molecular orbital) energy level, and is a material commonly used as the hole injection layer. The P-type dopant is a material that has a strong electron-attracting substituent and attracts electrons from the LUMO (lowest unoccupied molecular orbital) energy level of the hole transport layer adjacent to the P-type hole injection layer to the HOMO energy level of the P-type dopant. The P-type hole injection layer with a strong electron-attracting substituent forms a hole transport path by accepting electrons from the HOMO energy level of the host or the HOMO energy level of the hole injection layer or hole transport layer to the LUMO energy level of the P-type hole injection layer. After all, the LUMO energy level of the P-type hole injection layer and the HOMO energy level of the hole transport layer adjacent to the P-type hole injection layer or the host may be similar in energy level to enable efficient hole generation, so P-type hole injecting materials having a strong electron-attracting substituent are needed.

However, the P-type hole injecting materials are not easy to synthesize due to their strong electron-attracting substituent, and have problems with thermal stability and deposition stability. Particularly, $F_4$-TCNQ, one of the P-type hole injecting materials, sublimes easily, which affects the contamination of deposition sources, the performance reproducibility and thermal stability of devices during device fabrication. Moreover, it is not easy to develop P-type hole injecting materials whose LUMO energy level is similar to the HOMO energy level of the host or the HOMO energy level of the hole transport layer. In order to make the LUMO energy level similar to the HOMO energy level, it is necessary to introduce a strong electron-attracting substituent into the P-type hole injecting material. However, the stronger the electron-attracting substituent is, the harder it is to improve the purity of the material, making the synthesis of the material difficult. Besides, it is necessary that the strong electron-attracting substituent does not absorb visible light, which makes the development of P-type hole injecting materials difficult.

SUMMARY OF THE DISCLOSURE

Accordingly, the present disclosure is directed to an organic light emitting display device that substantially obviates one or more of the problems due to limitations and disadvantages of the related art.

An object of the present disclosure is to provide an organic light emitting display device with reduced operating voltage and improved efficiency.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

To achieve these and other advantages and in accordance with the purpose of the disclosure, as embodied and broadly described, an organic light emitting display device comprises at least one light emitting part between an anode and a cathode, and the at least one light emitting part having at least one organic layer and a light emitting layer, wherein the at least one organic layer comprises a compound represented by the following Chemical Formula 1 or 2:

[Chemical Formula 1]

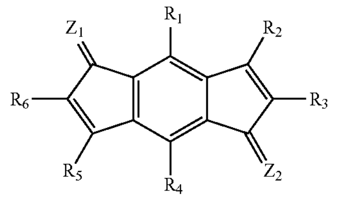

-continued

[Chemical Formula 2]

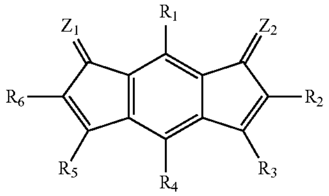

where $R_1$ to $R_6$ each independently represents one among a hydrogen atom, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted or unsubstituted alkyl group with 1 to 12 carbon atoms, a substituted or unsubstituted alkoxy group with 1 to 12 carbon atoms, a substituted or unsubstituted ether group with 1 to 12 carbon atoms, a cyano group, a fluorine group, a trifluoromethyl group, a trifluoromethoxy group, and a trimethylsilyl group, and at least one among $R_1$ to $R_6$ comprises a cyano group, and $Z_1$ and $Z_2$ are independently represented by the following Chemical Formula 3:

[Chemical Formula 3]

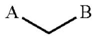

where A and B are independently represented by one among a hydrogen atom, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted or unsubstituted alkyl group with 1 to 12 carbon atoms, a substituted or unsubstituted alkoxy group with 1 to 12 carbon atoms, a substituted or unsubstituted ether group with 1 to 12 carbon atoms, a cyano group, a fluorine group, a trifluoromethyl group, a trifluoromethoxy group, and a trimethylsilyl group.

The substituent of the aryl group, heteroaryl group, alkyl group, alkoxy group, and ether group is one among an alkyl with 1 to 12 carbon atoms, an aryl with 6 to 15 carbon atoms, a hetero aryl with 1 to 15 carbon atoms and 1 to 4 heteroatoms one among O, N, S, and Si, a cyano group, a fluorine group, a trifluoromethyl group, a trifluoromethoxy group, and a trimethylsilyl group.

The compound represented by Chemical Formula 1 is represented by one among the following compounds:

A01

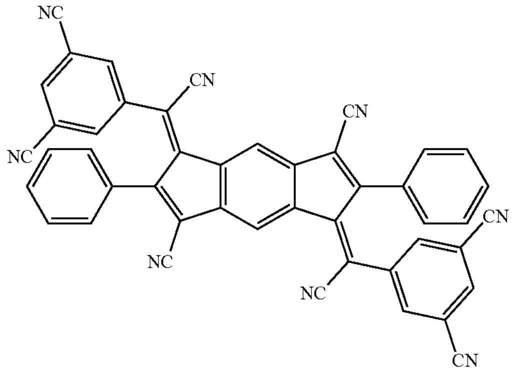

-continued

A02

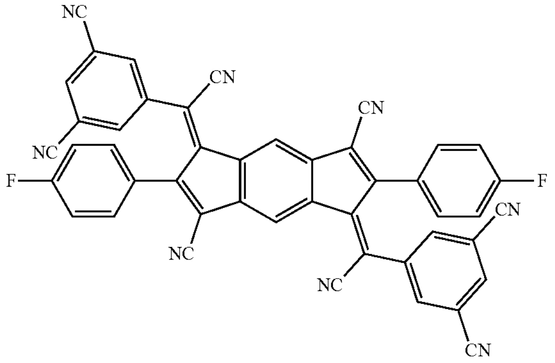

A03

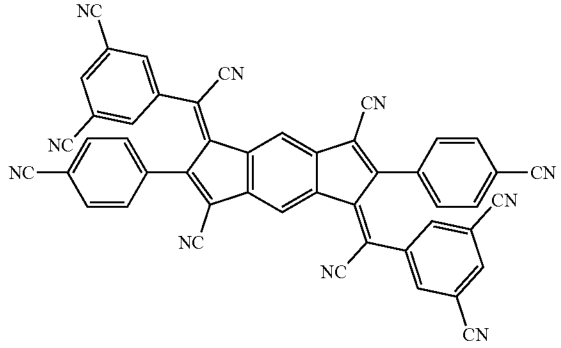

A04

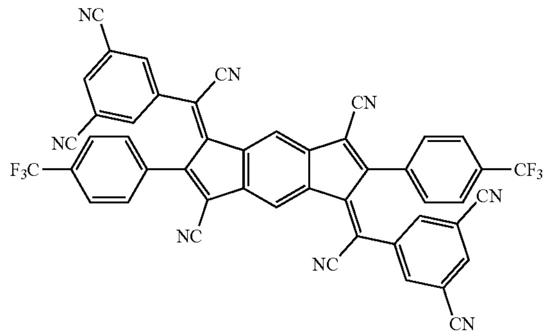

A05

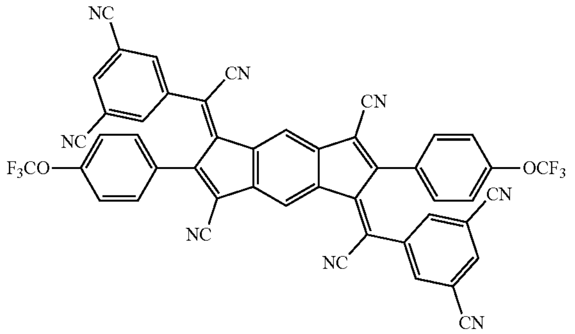

-continued
A06
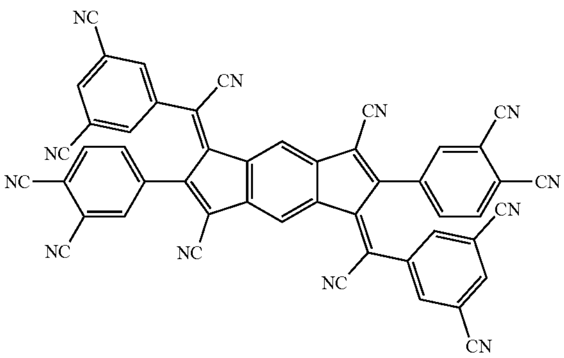
A07
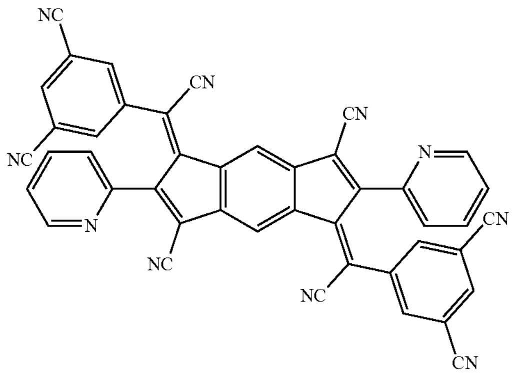
A08
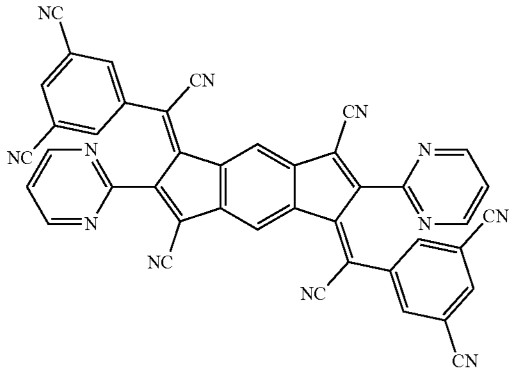
A09
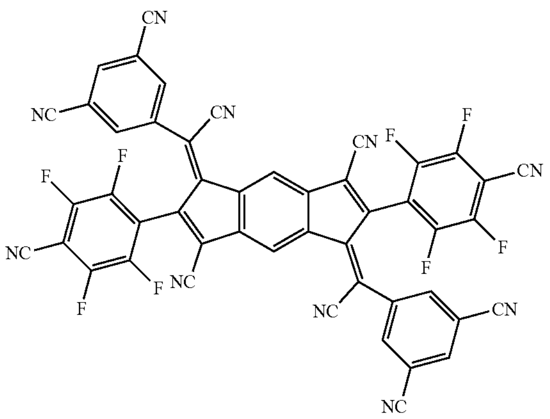
-continued
A10
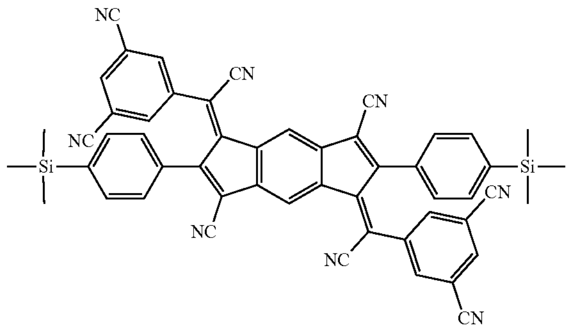
A11
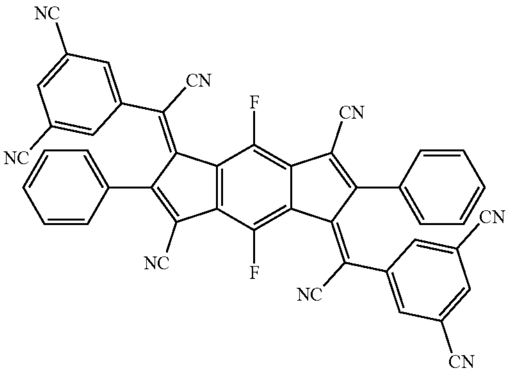
A12
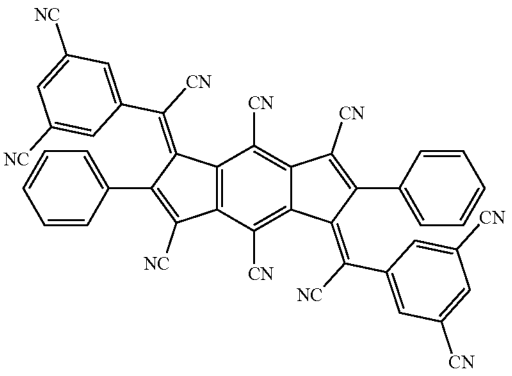
A13
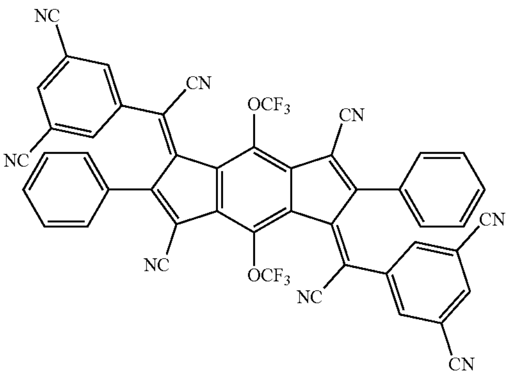

A14
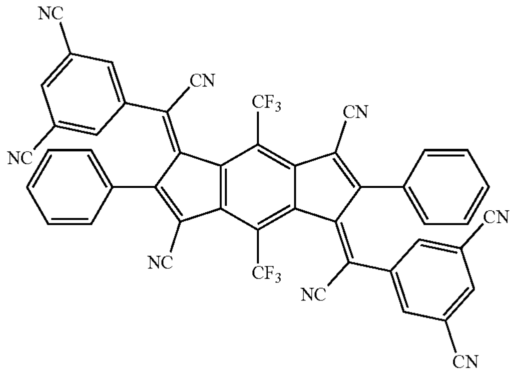
A15
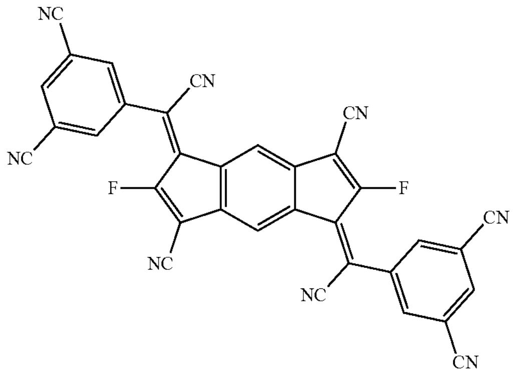
A16
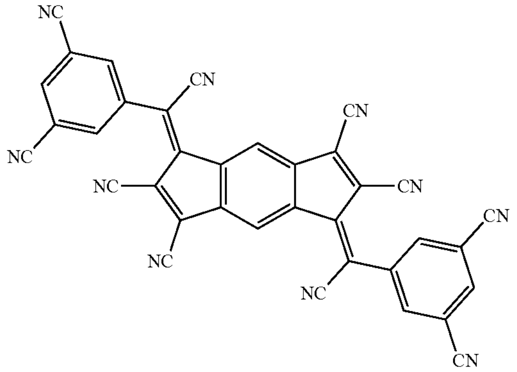
A17
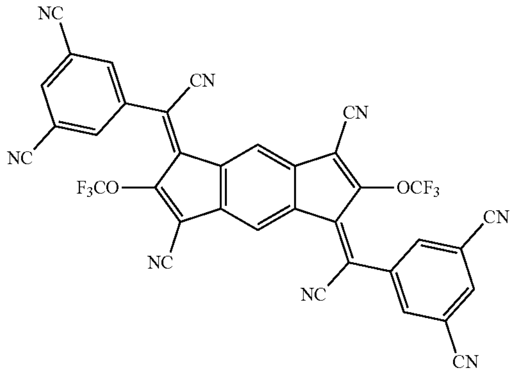
A18
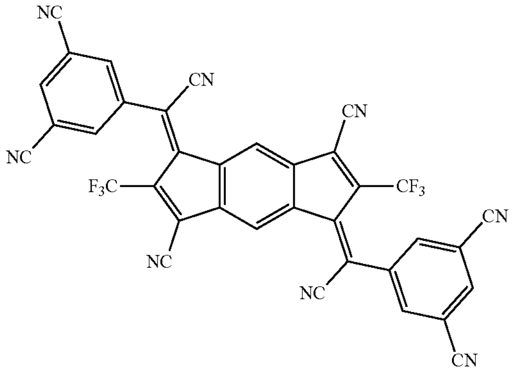
A19
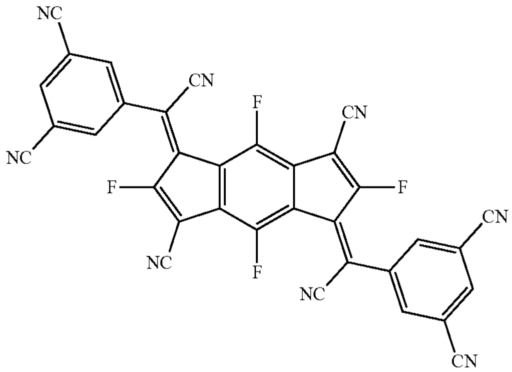
A20
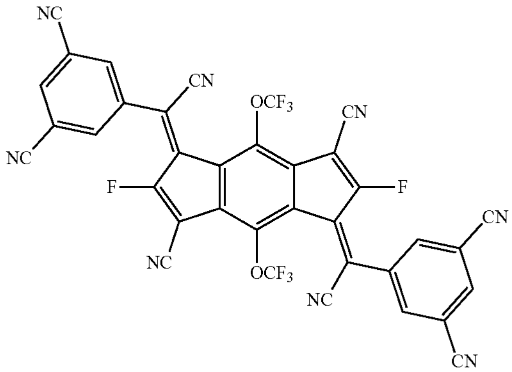
A21
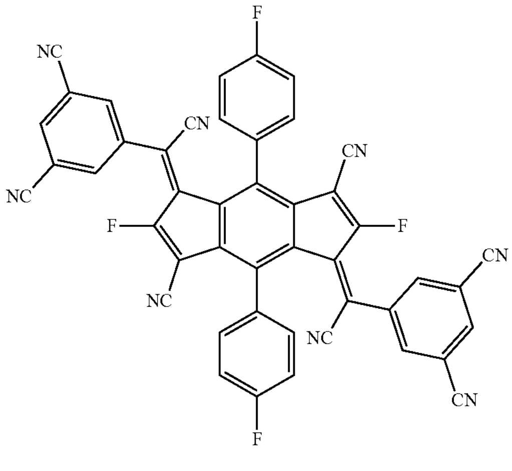

-continued
A22
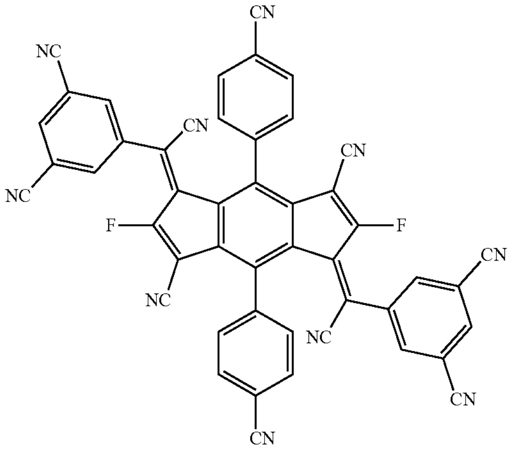
A23
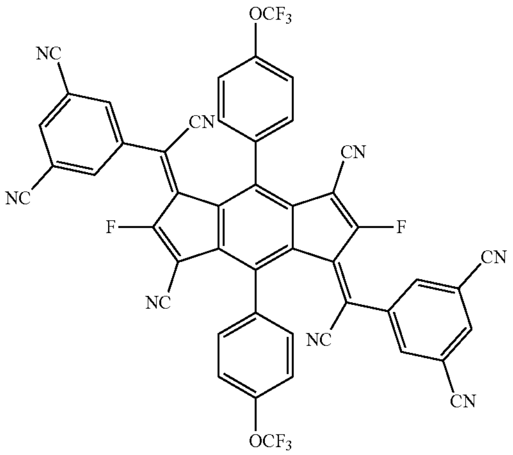
A24
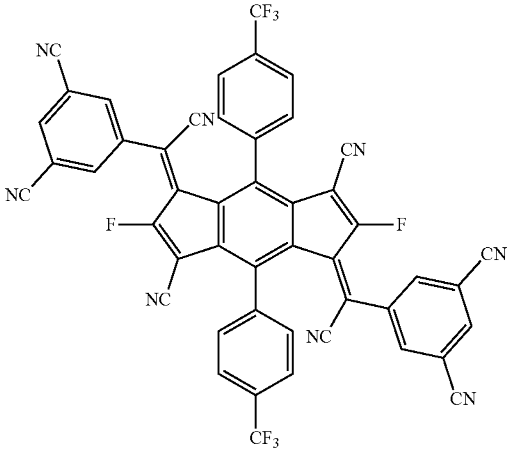
-continued
A25
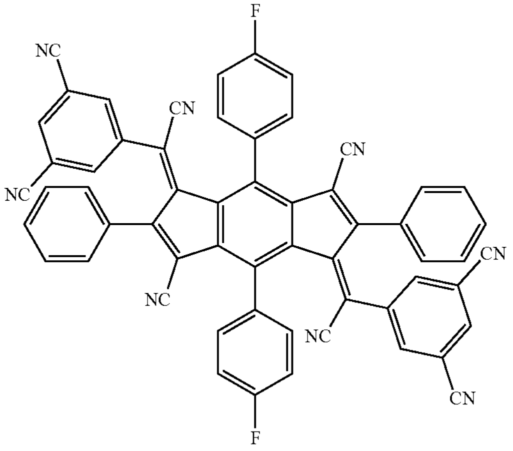
A26
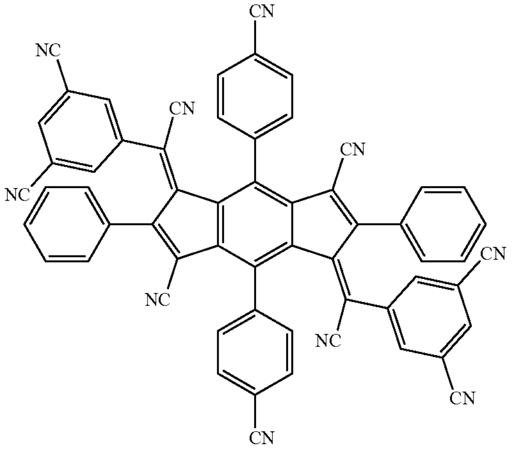
A27
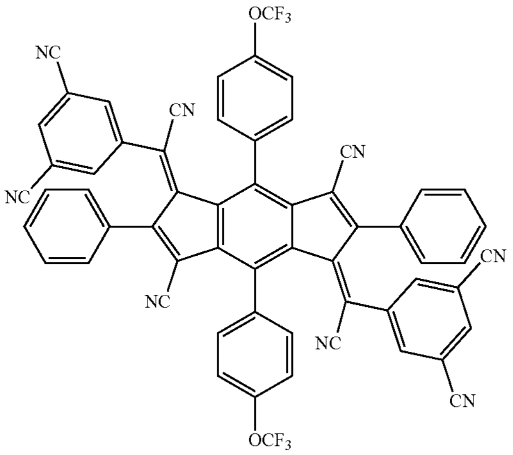

-continued
A28
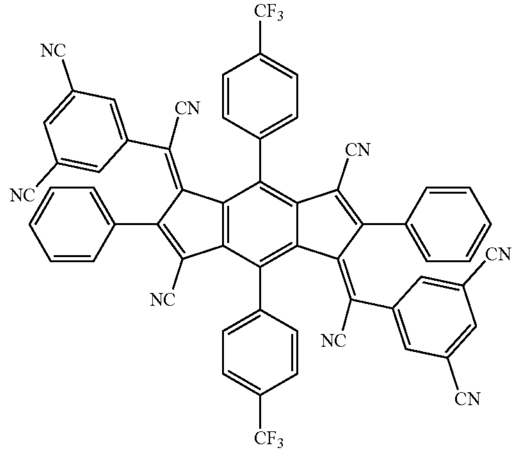
A29
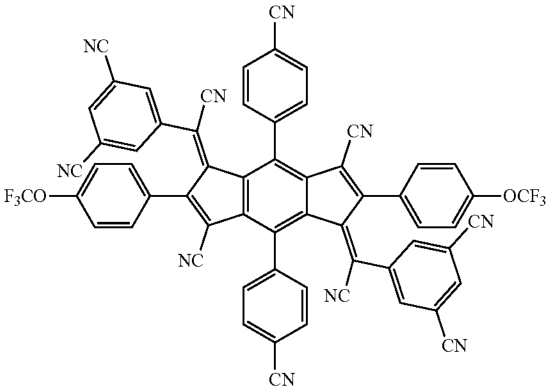
A30
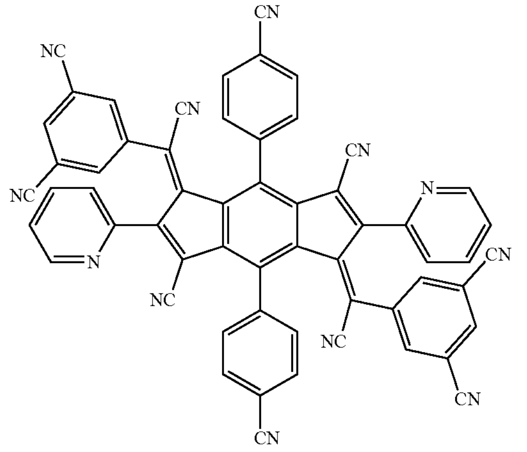
A31
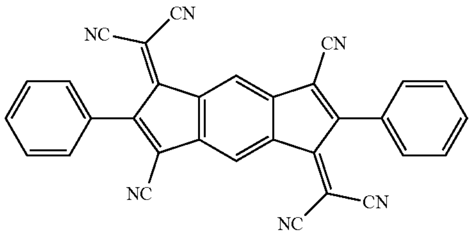
-continued
A32
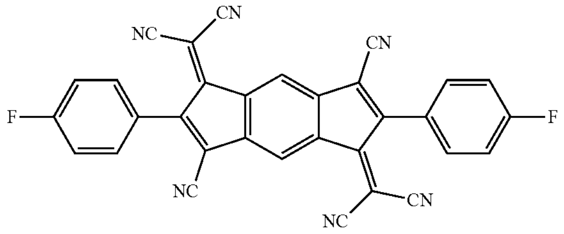
A33
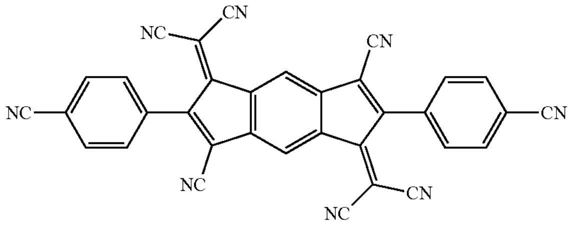
A34
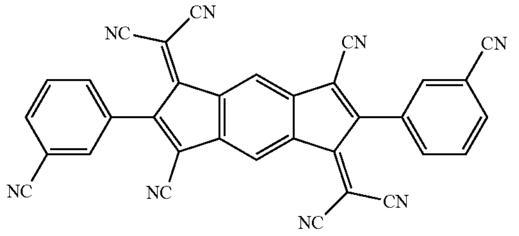
A35
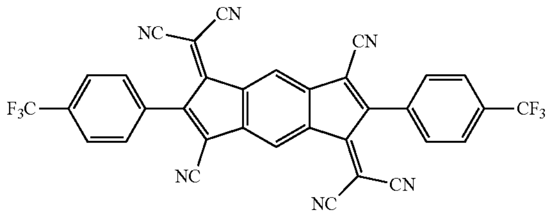
A36
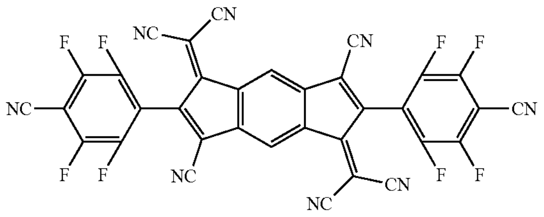
A37
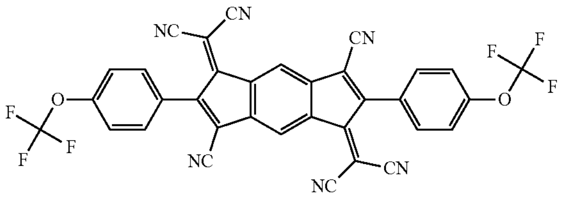

-continued
A38
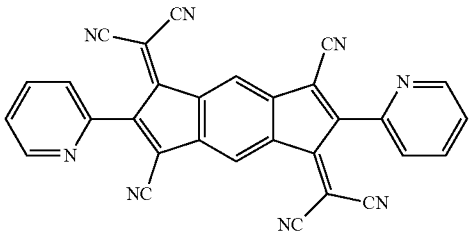
A39
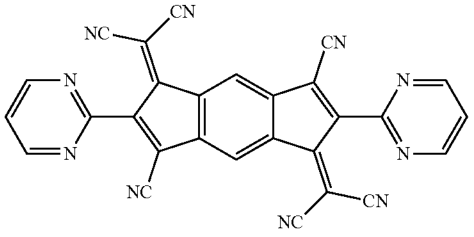
A40
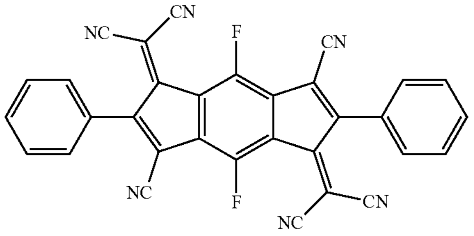
A41
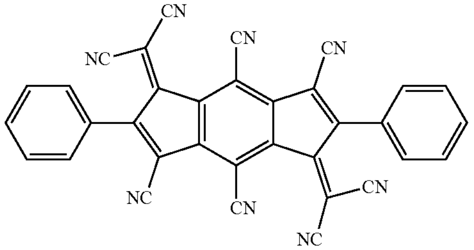
A42
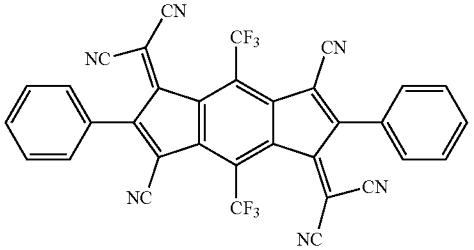
A43
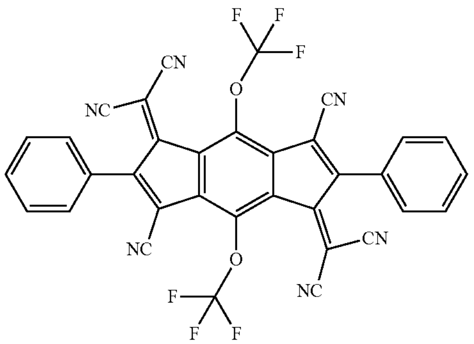
-continued
A44
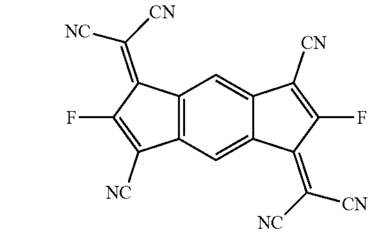
A45
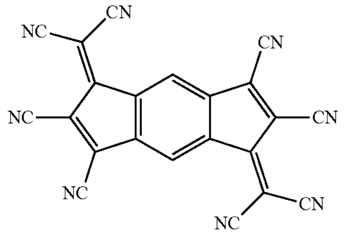
A46
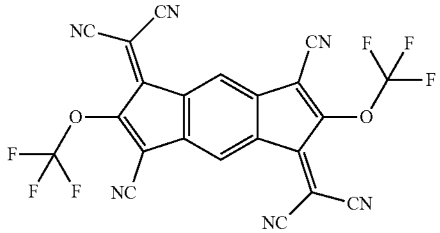
A47
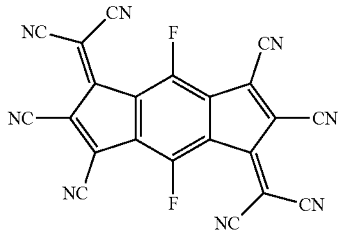
A48
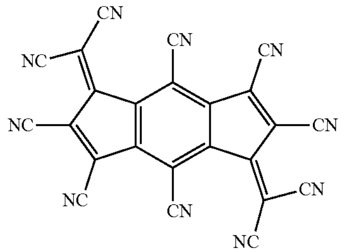
A49
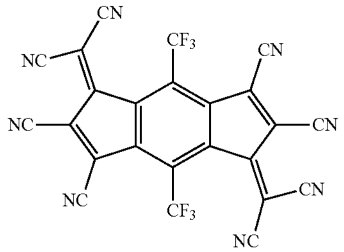

-continued
A50
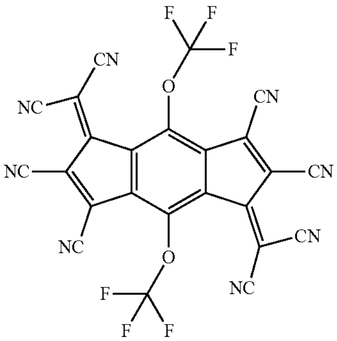
A51
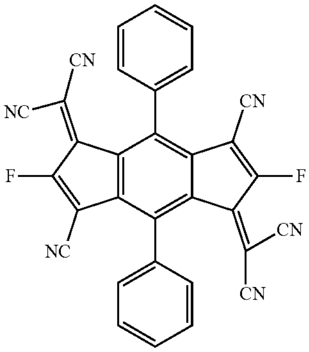
A52
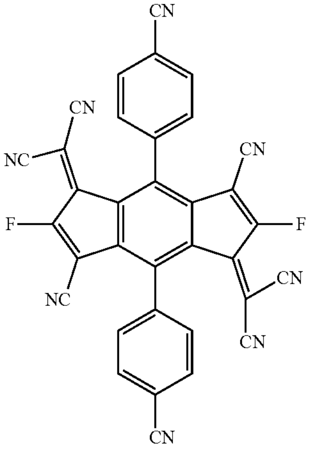
A53
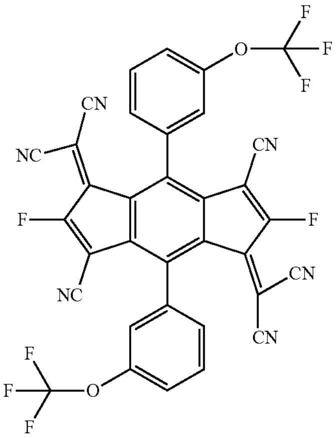
-continued
A54
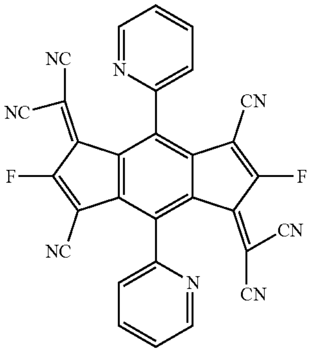
A55
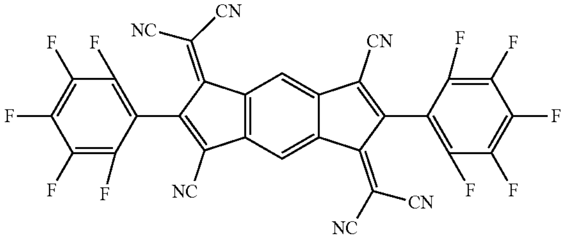
lp;2p
A56
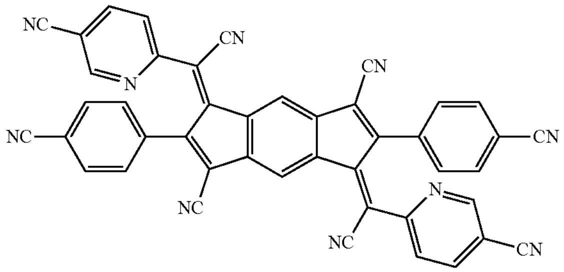
A57
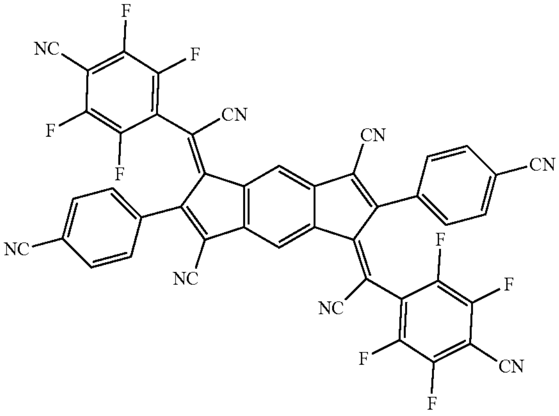

-continued
A58
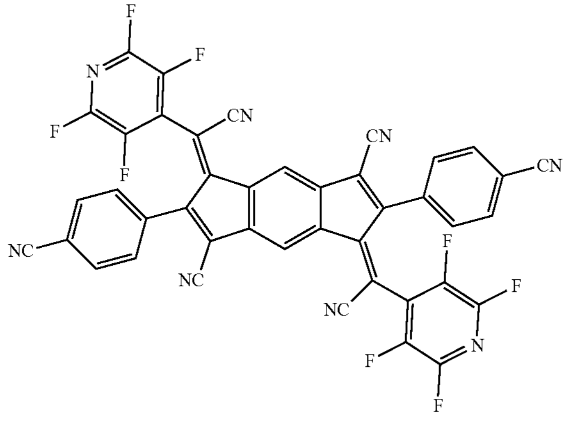
A59
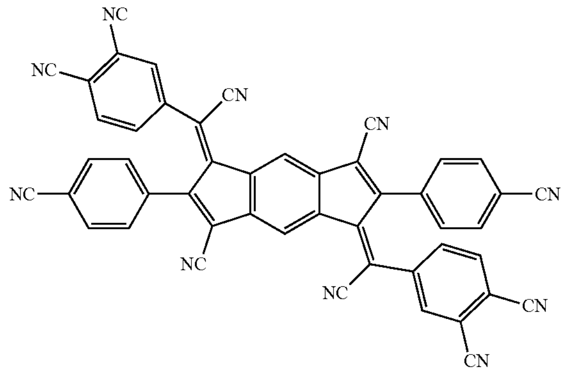
A60
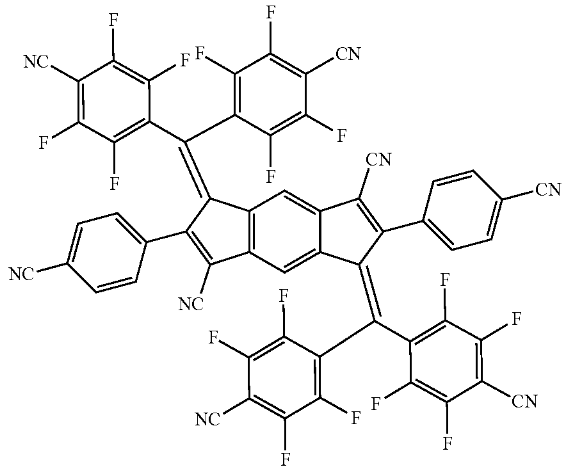
-continued
A61
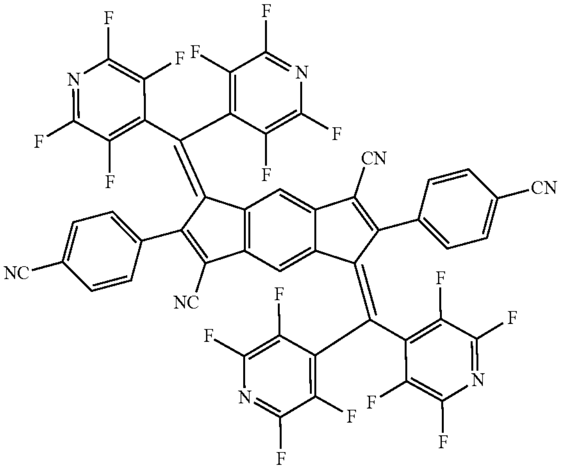
A62
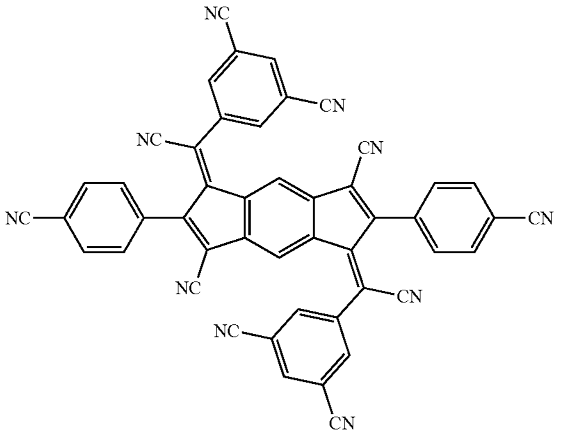
A63
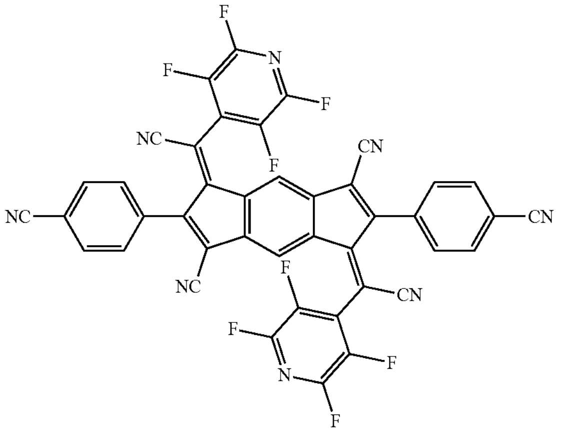
A64
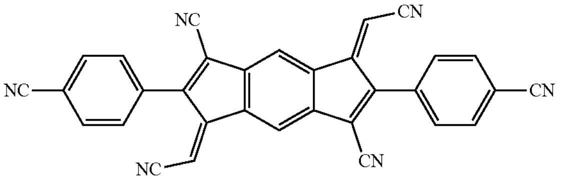

The compound represented by the above Chemical Formula 2 is represented by one among the following compounds:
B1
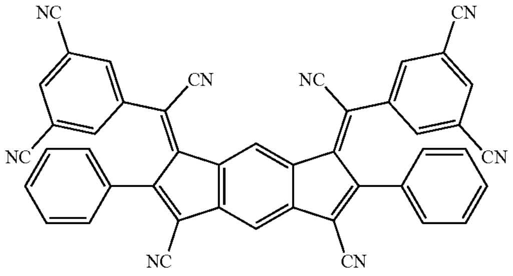
B2
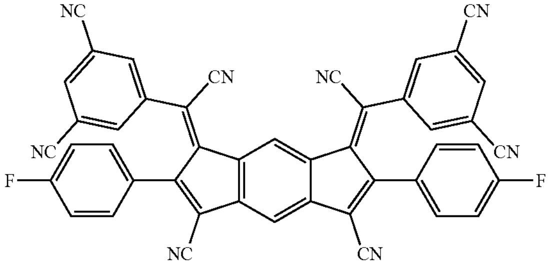
B3
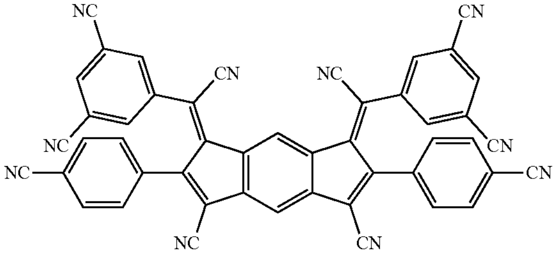
B4
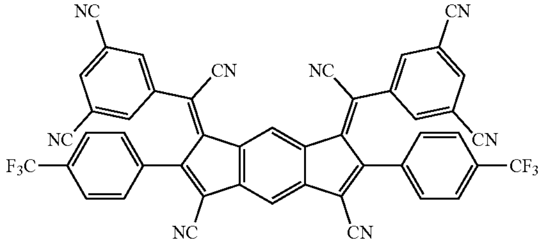
B5
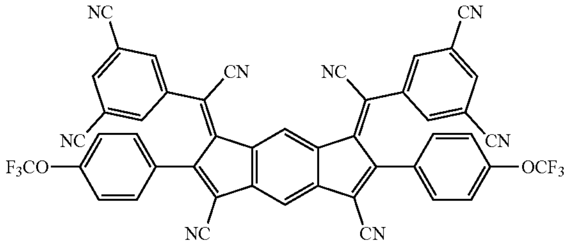
-continued
B6
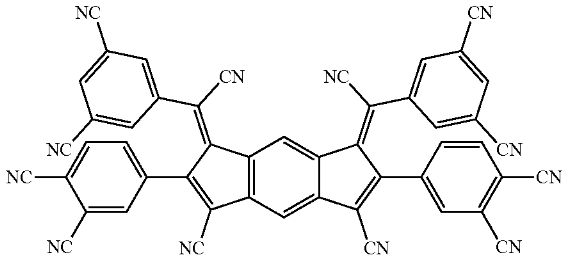
B7
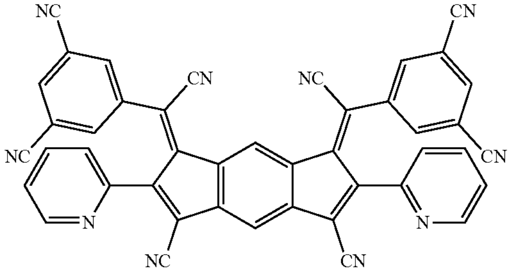
B8
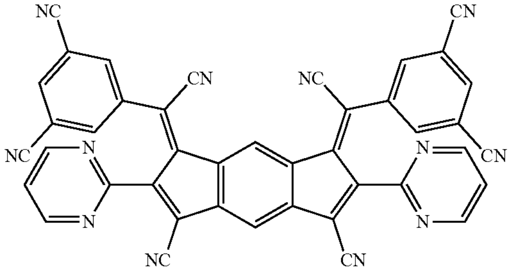
B9
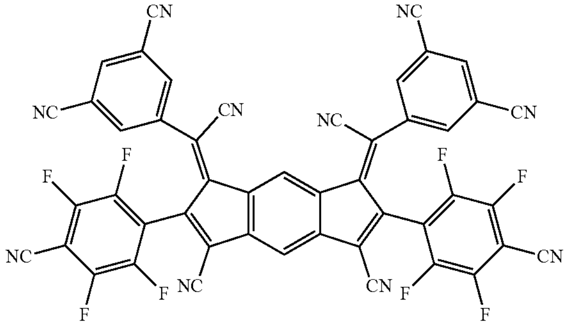
B10
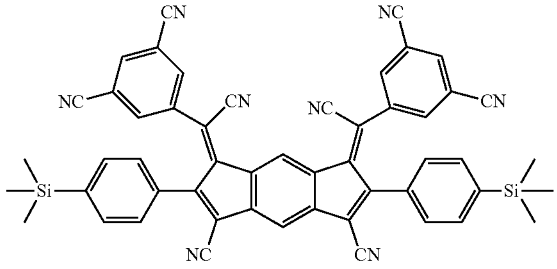

-continued
B11
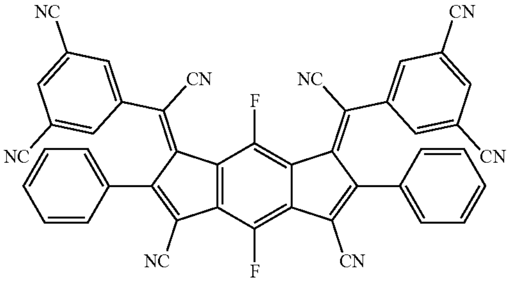
B12
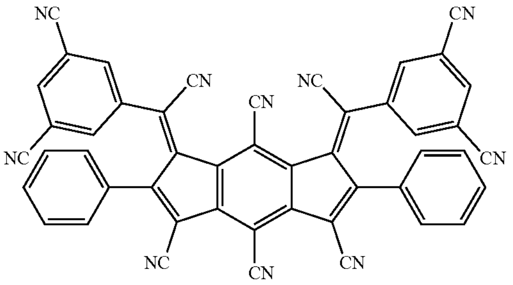
B13
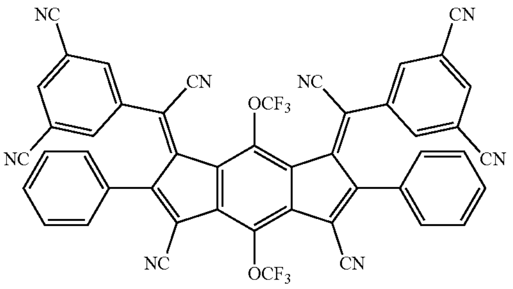
B14
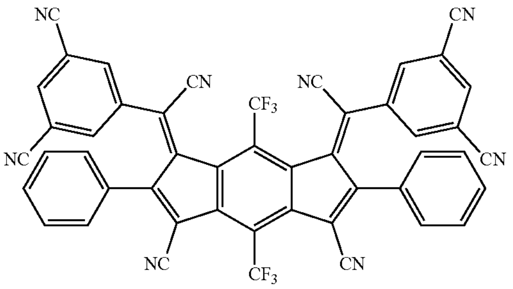
B15
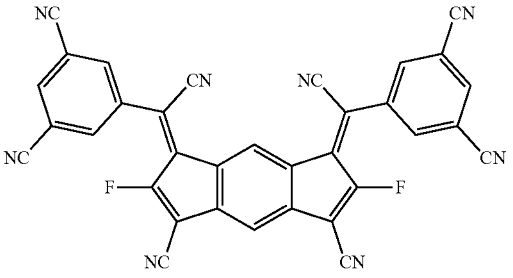
-continued
B16
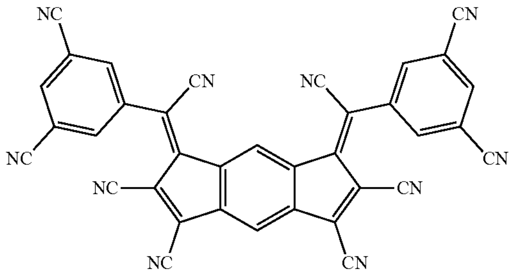
B17
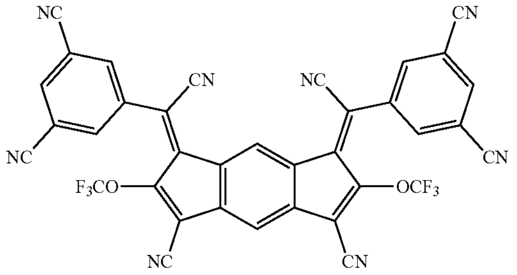
B18
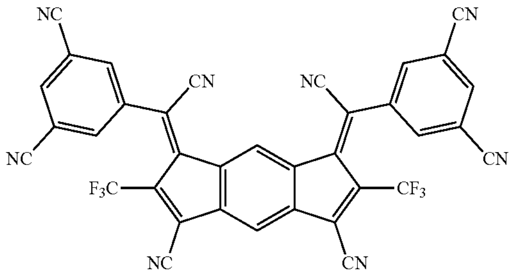
B19
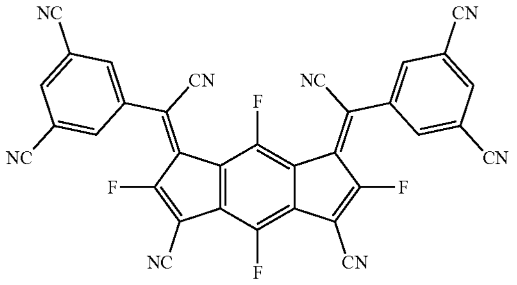
B20
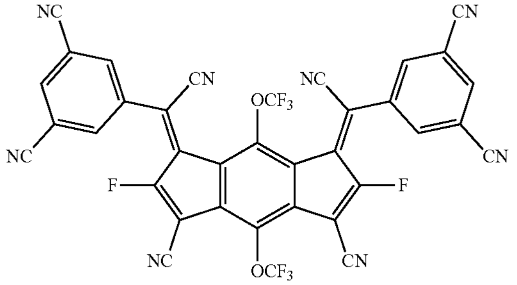

-continued
B21
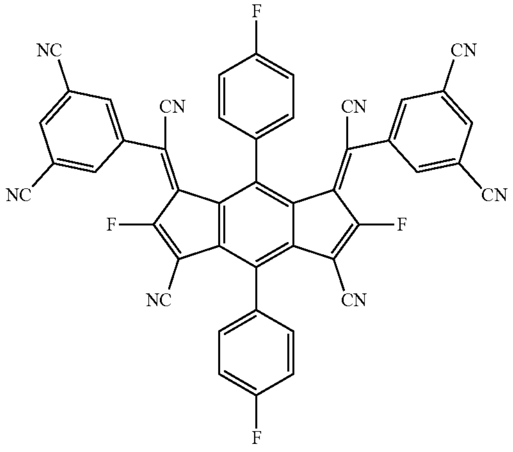
B22
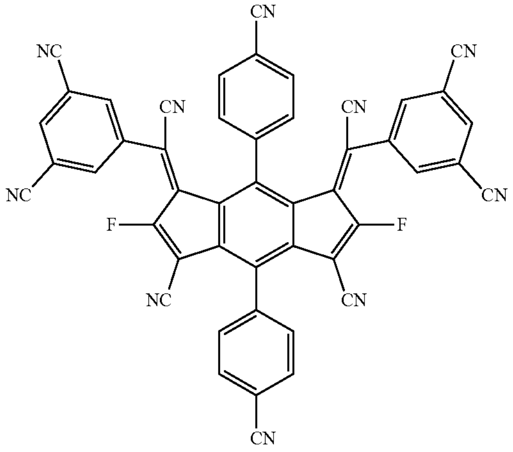
B23
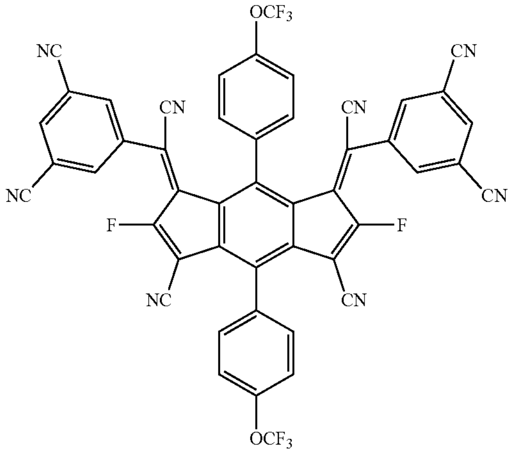
-continued
B24
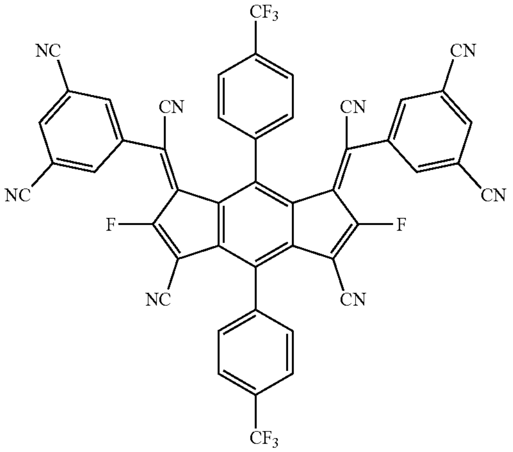
B25
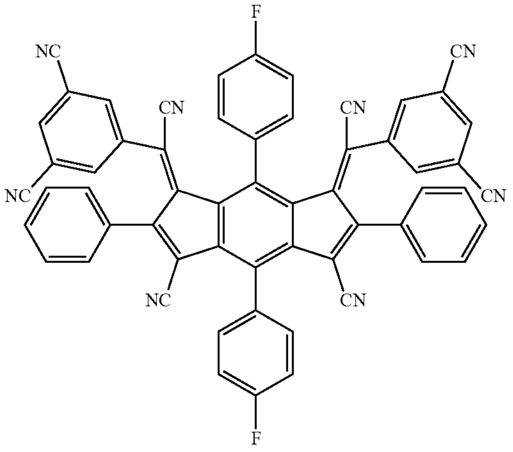
B26
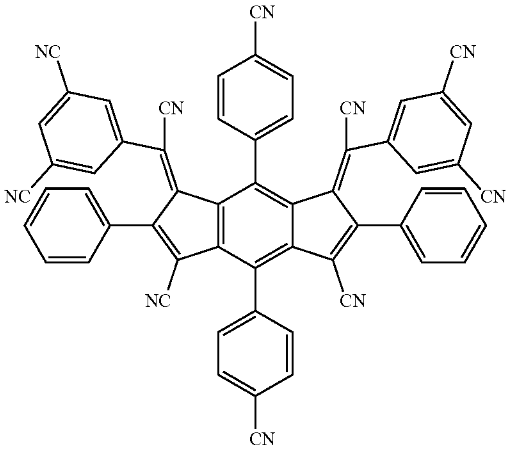

-continued
B27
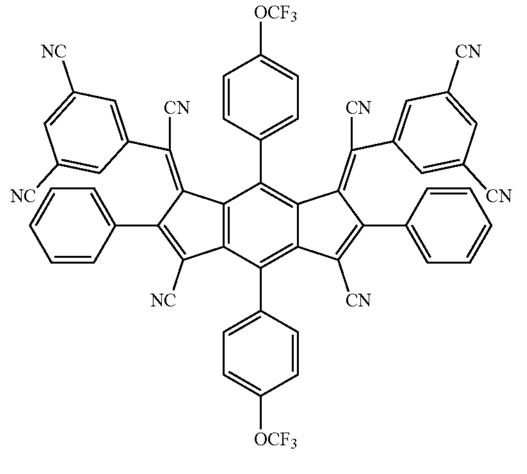
B28
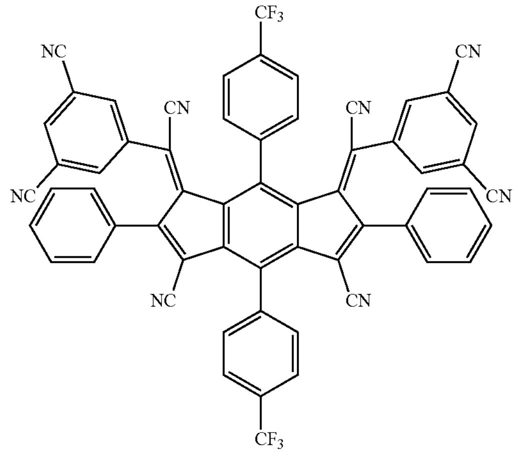
B29
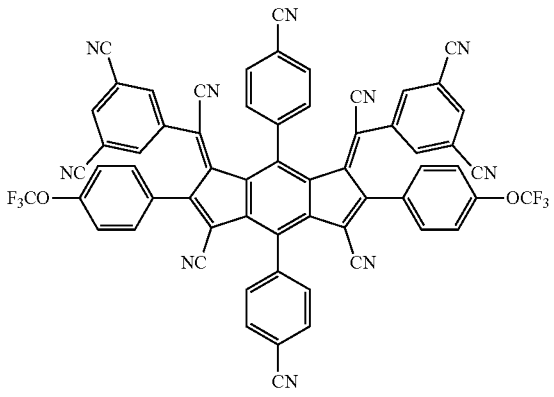
-continued
B30
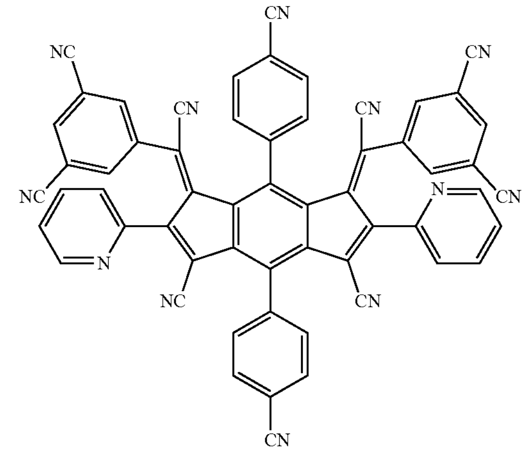
B31
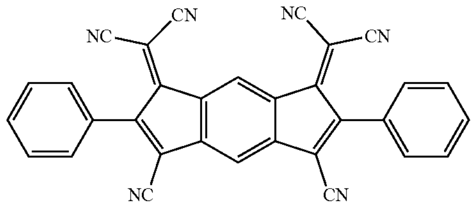
B32
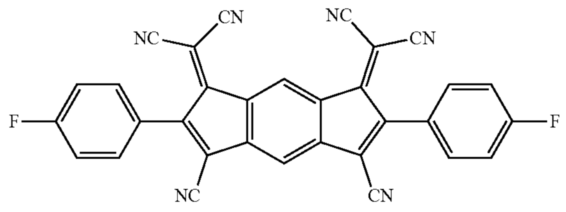
B33
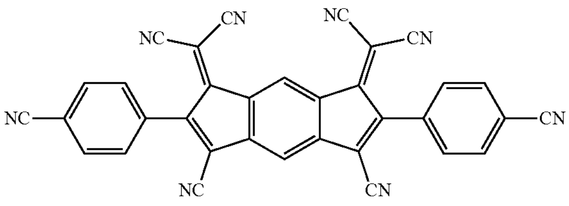
B34
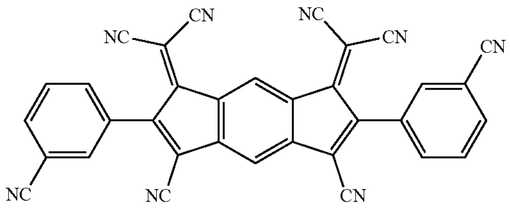
B35
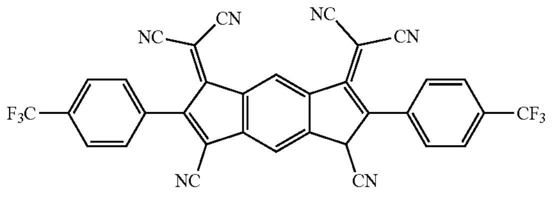

-continued
B36
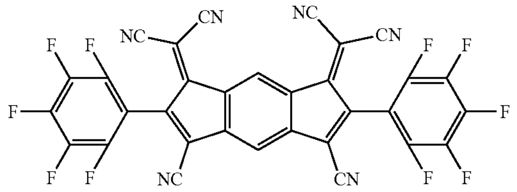
B37
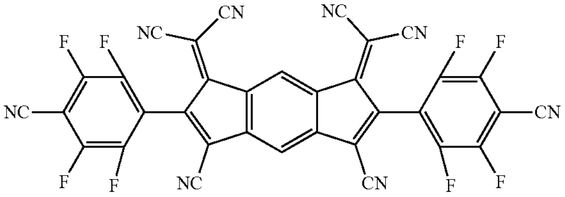
B38
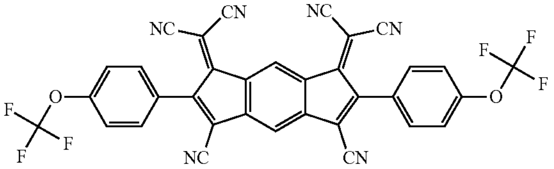
B39
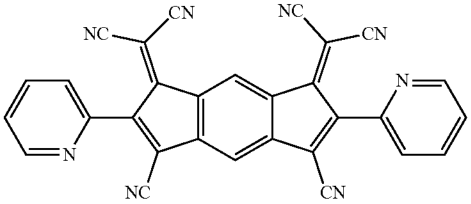
B40
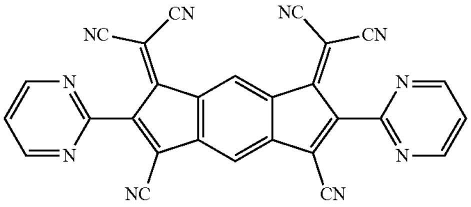
B41
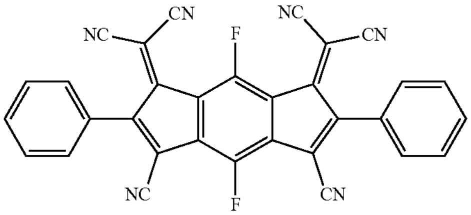
B42
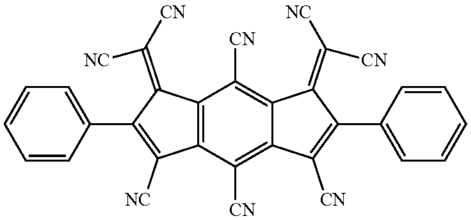
-continued
B43
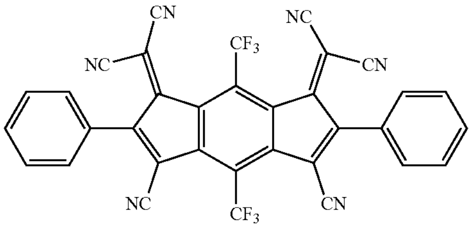
B44
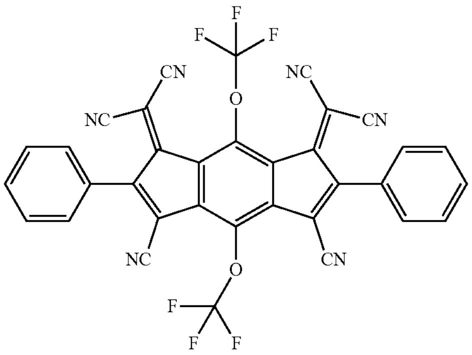
B45
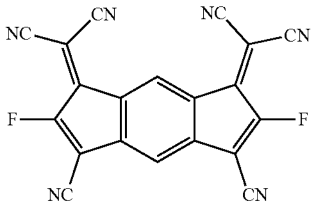
B46
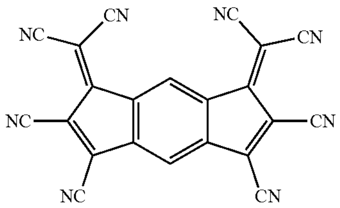
B47
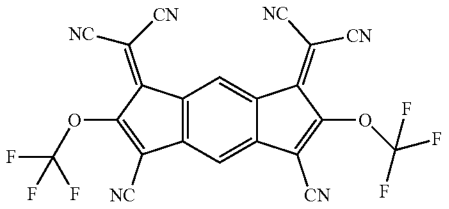
B48
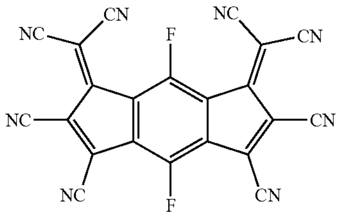

-continued

B49

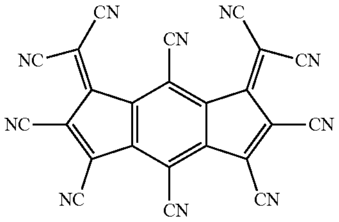

B50

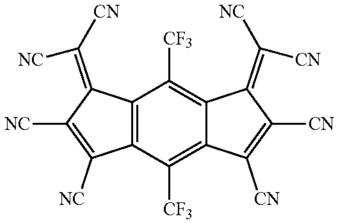

B51

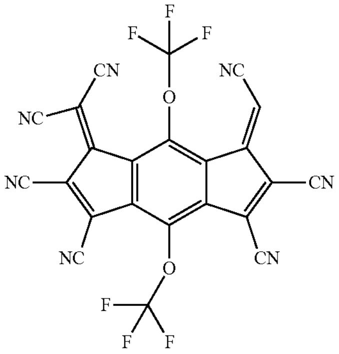

B52

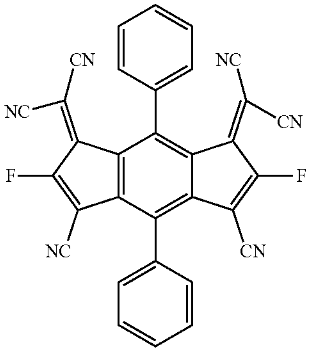

B53

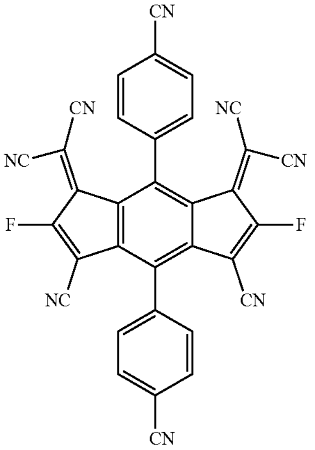

-continued

B54

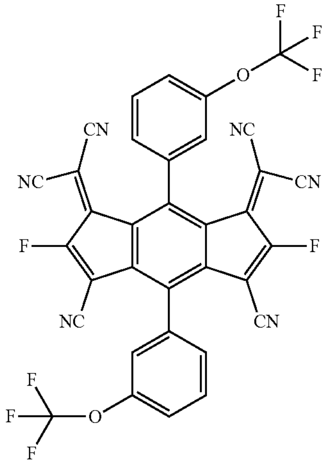

B55

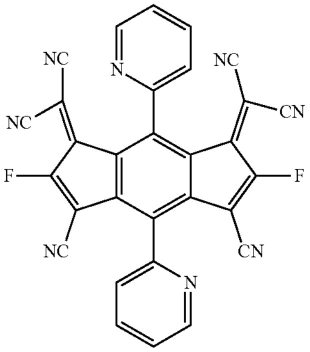

B56

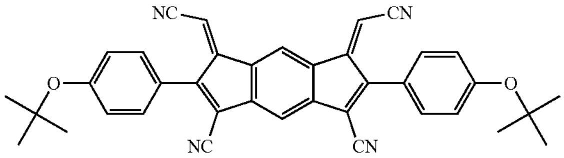

The at least one organic layer includes a hole injection layer.

A dopant of the hole injection layer includes the compound.

The hole injection layer includes the compound.

The at least one organic layer includes a P-type charge generation layer.

A dopant of the P-type charge generation layer includes the compound.

The P-type charge generation layer includes the compound.

In another aspect, an organic light emitting display device comprises at least one light emitting part between an anode and a cathode, and the at least one light emitting part having a hole injection layer and a light emitting layer, and a charge generation layer having a P-type charge generation layer between the at least one light emitting parts, wherein at least one among the hole injection layer and the P-type charge generation layer comprises a compound represented by the following Chemical Formula 1 or 2:

[Chemical Formula 1]

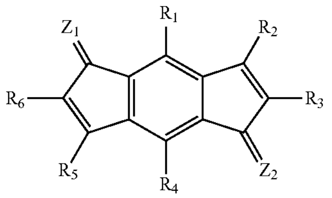

[Chemical Formula 2]

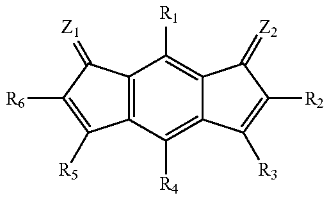

where $R_1$ to $R_6$ each independently represents one among a hydrogen atom, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted or unsubstituted alkyl group with 1 to 12 carbon atoms, a substituted or unsubstituted alkoxy group with 1 to 12 carbon atoms, a substituted or unsubstituted ether group with 1 to 12 carbon atoms, a cyano group, a fluorine group, a trifluoromethyl group, a trifluoromethoxy group, and a trimethylsilyl group, and at least one among $R_1$ to $R_6$ comprises a cyano group, and $Z_1$ and $Z_2$ are independently represented by the following Chemical Formula 3:

[Chemical Formula 3]

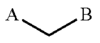

where A and B independently represent one among a hydrogen atom, a substituted or unsubstituted aryl group with 6 to 12 carbon atoms, a substituted or unsubstituted heteroaryl group with 1 to 12 carbon atoms, a substituted or unsubstituted alkyl group with 1 to 12 carbon atoms and 1 to 4 heteroatoms one among O, N, S, and Si, a substituted or unsubstituted alkoxy group with 1 to 12 carbon atoms, a substituted or unsubstituted ether group with 1 to 12 carbon atoms, a cyano group, a fluorine group, a trifluoromethyl group, a trifluoromethoxy group, and a trimethylsilyl group.

The substituent of the aryl group, heteroaryl group, alkyl group, alkoxy group, and ether group is one among an alkyl with 1 to 12 carbon atoms, an aryl with 6 to 15 carbon atoms, a hetero aryl with 1 to 15 carbon atoms and 1 to 4 heteroatoms one among O, N, S, and Si, a cyano group, a fluorine group, a trifluoromethyl group, a trifluoromethoxy group, and a trimethylsilyl group.

The compound represented by Chemical Formula 1 is represented by one among the following compounds:

A01

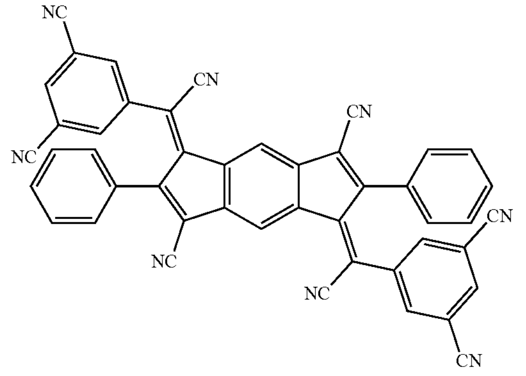

A02

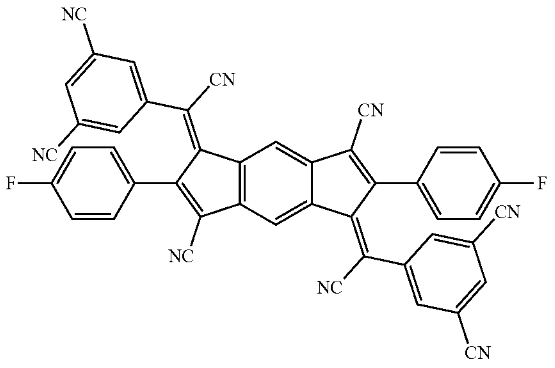

A03

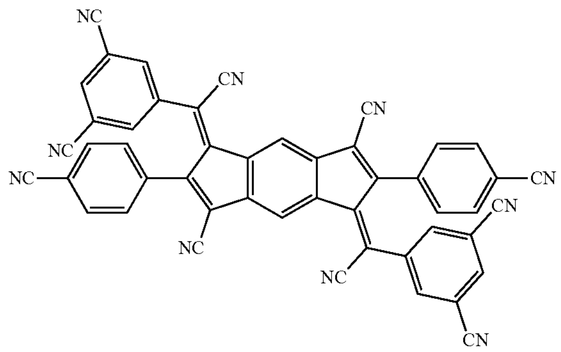

A04

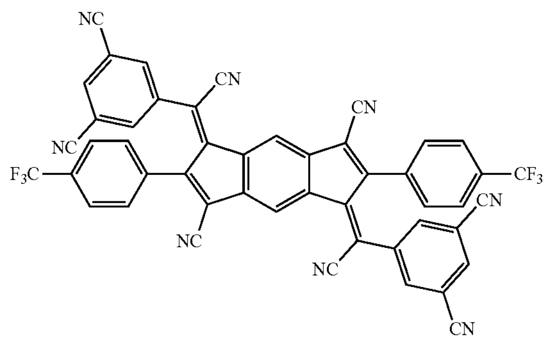

-continued
A05
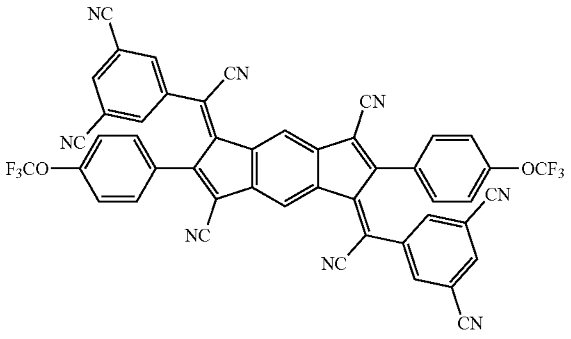
A06
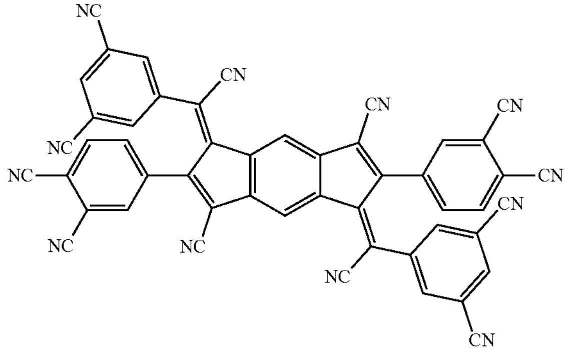
A07
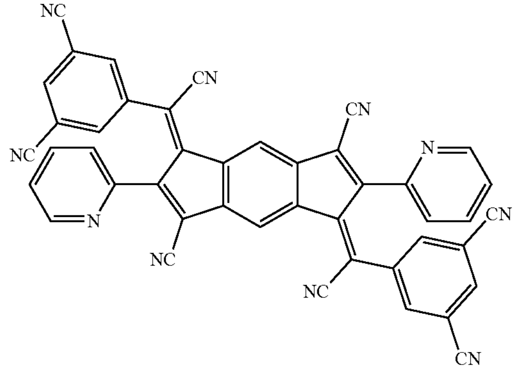
A08
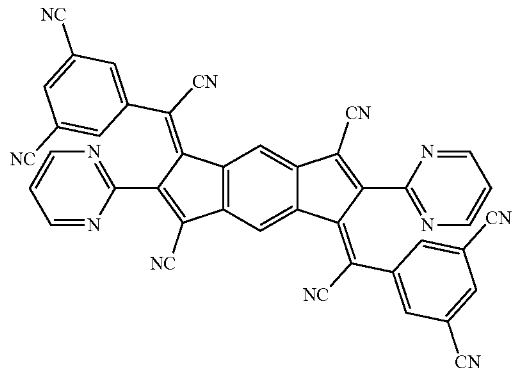
-continued
A09
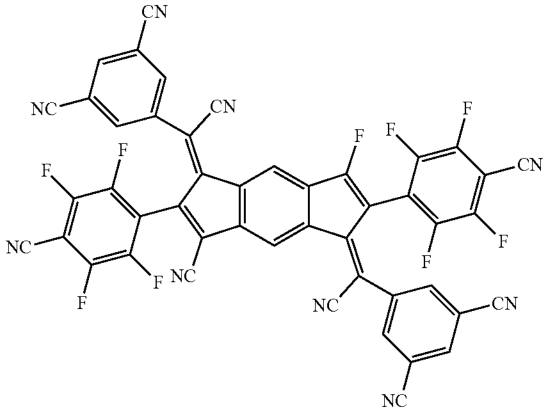
A10
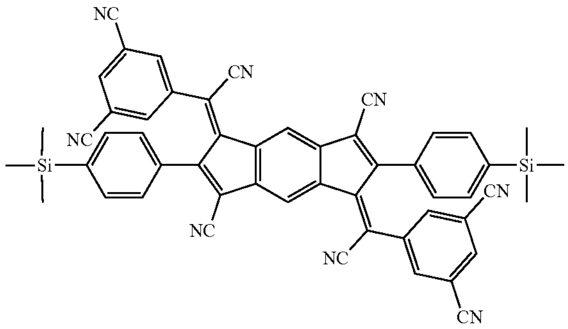
A11
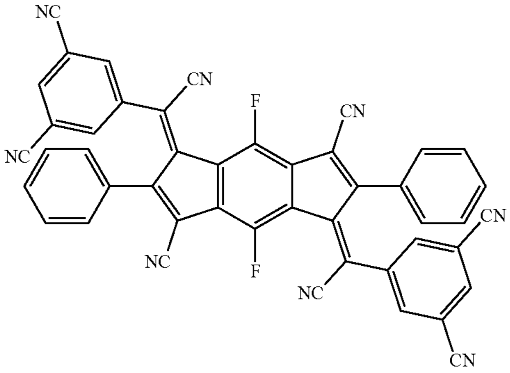
A12
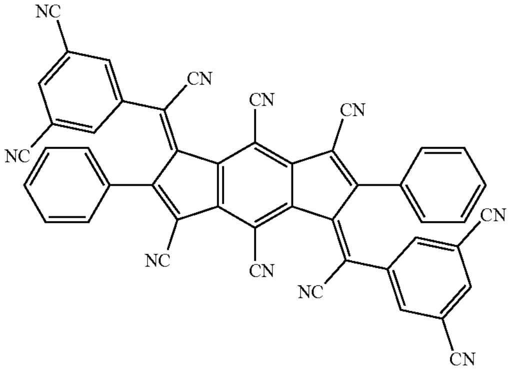

-continued
A13
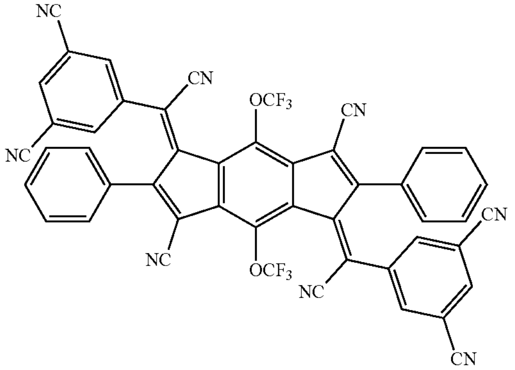
A14
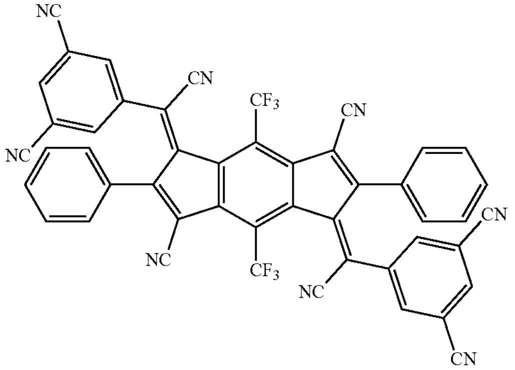
A15
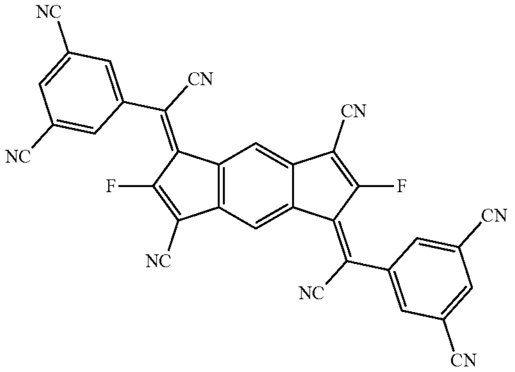
A16
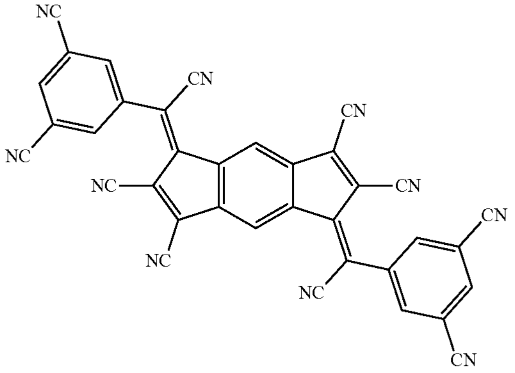
-continued
A17
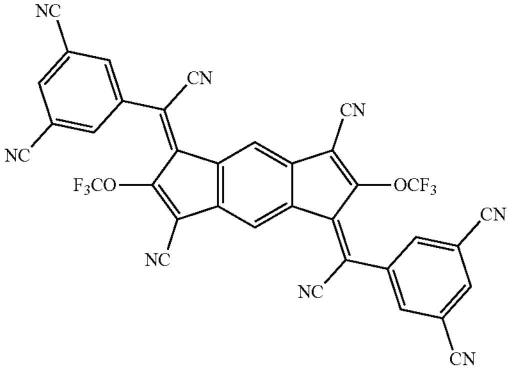
A18
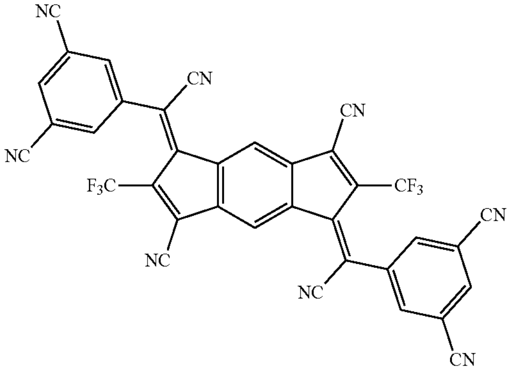
A19
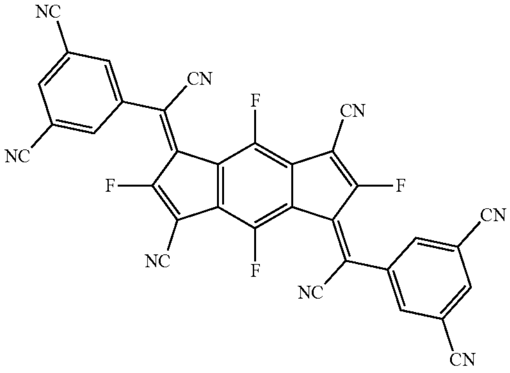
A20
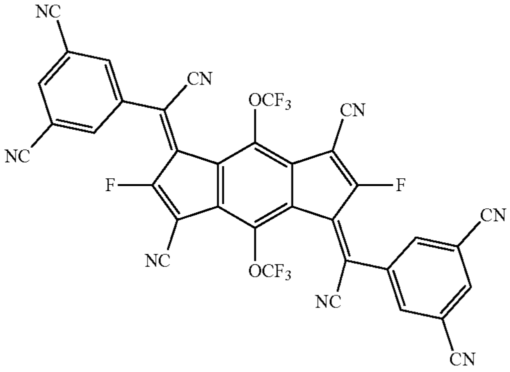

-continued
A21
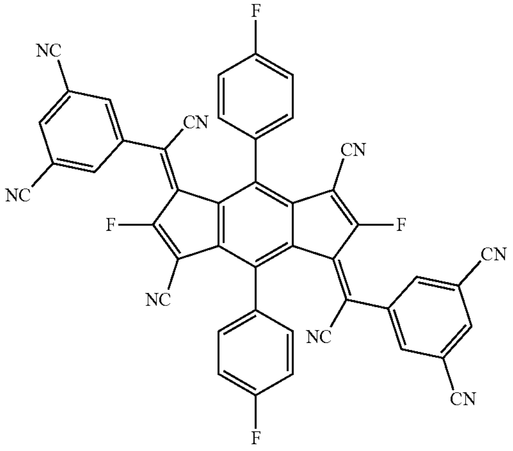
A22
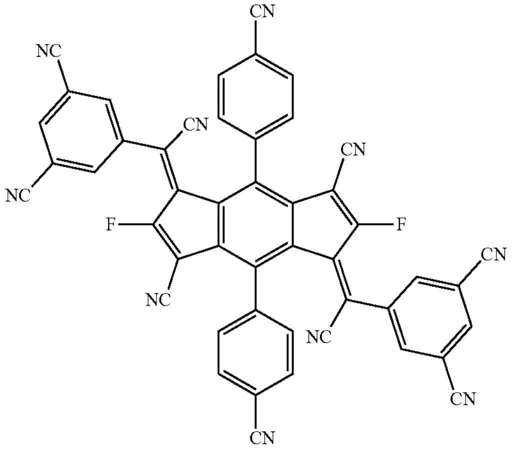
A23
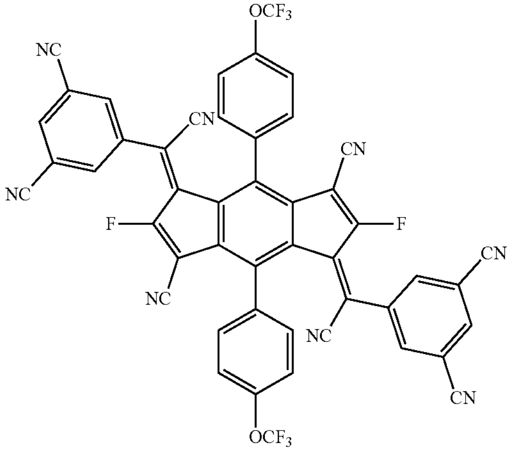
-continued
A24
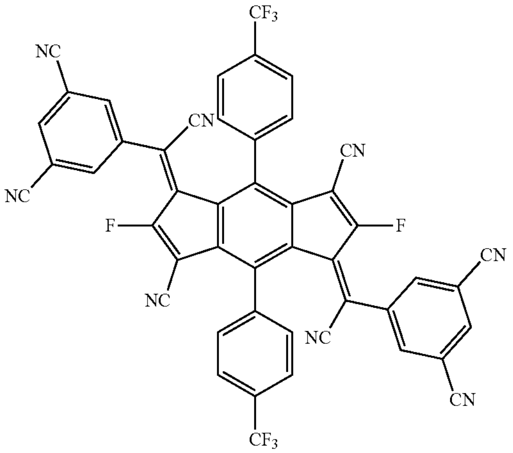
A25
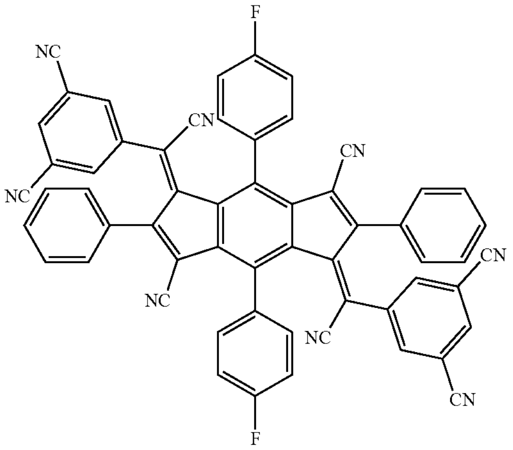
A26
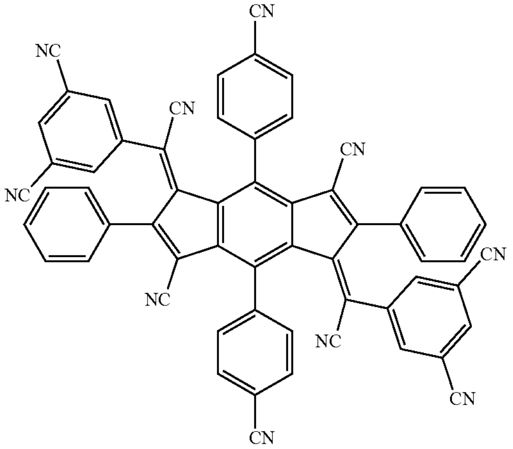

-continued
A27
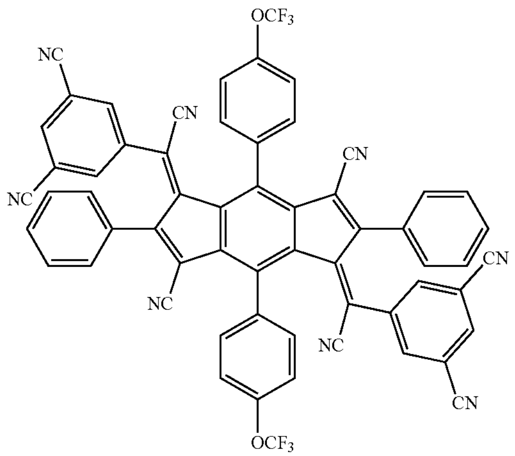
A28
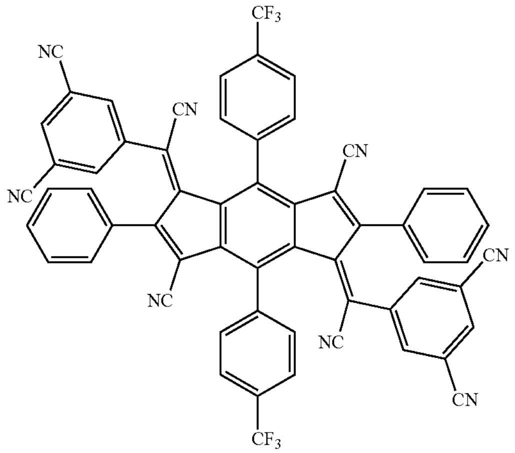
A29
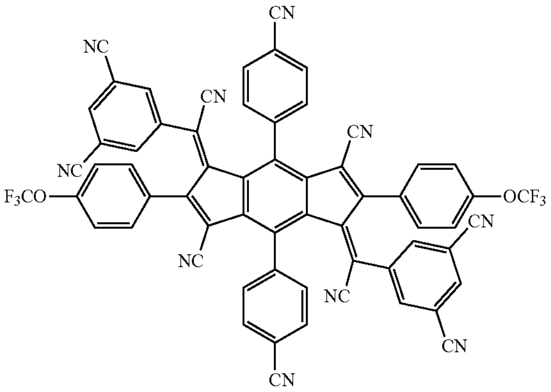
-continued
A30
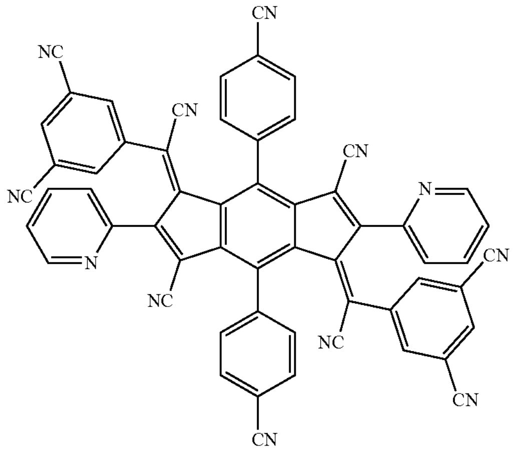
A31
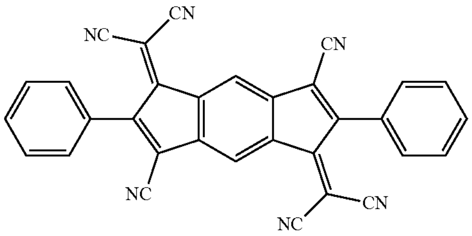
A32
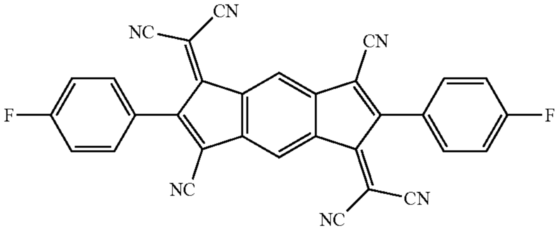
A33
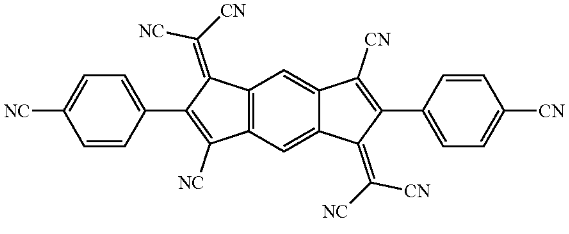
A34
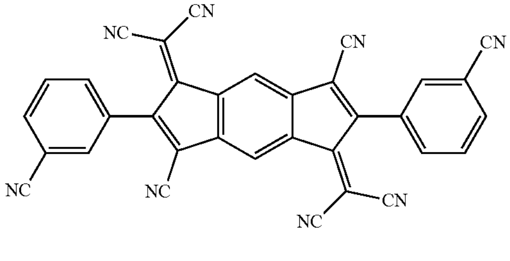

-continued
A35
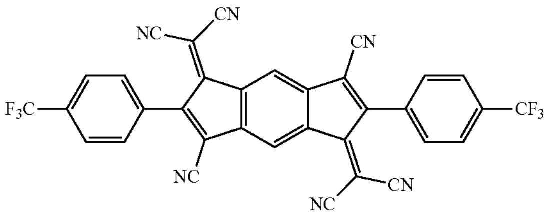
A36
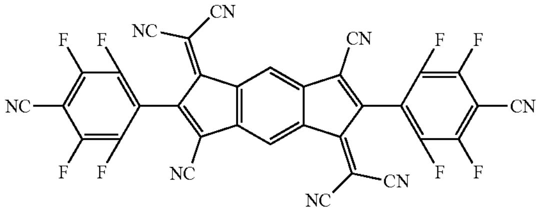
A37
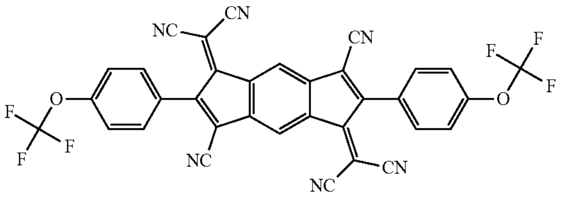
A38
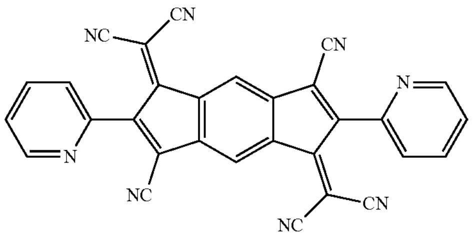
A39
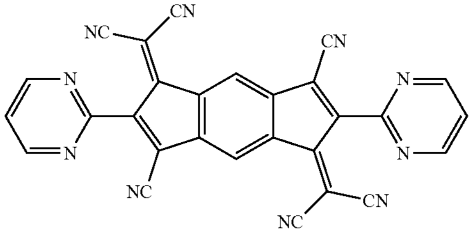
A40
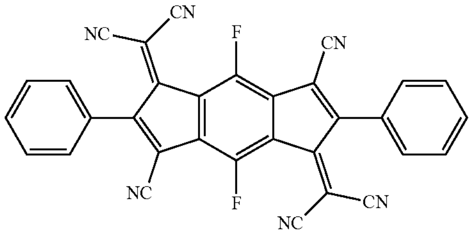
-continued
A41
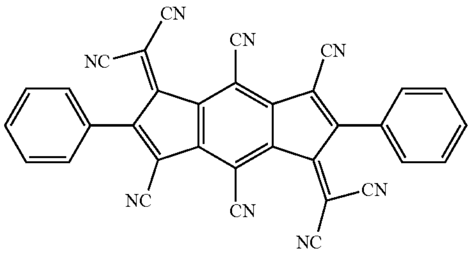
A42
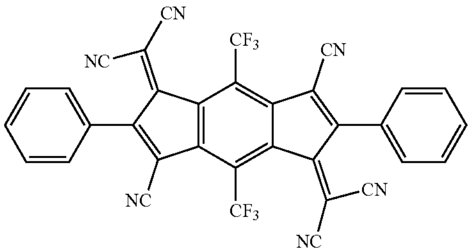
A43
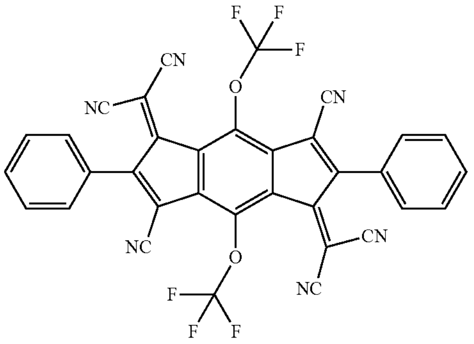
A44
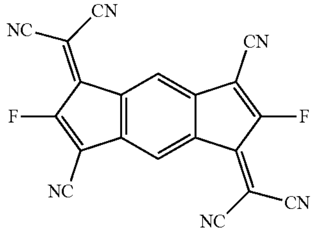
A45
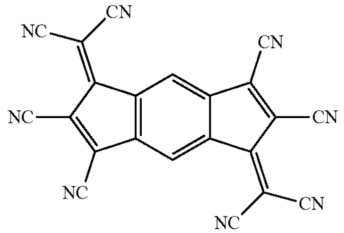
A46
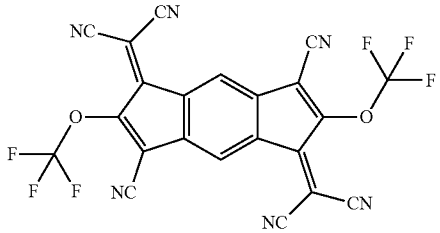

-continued
A47
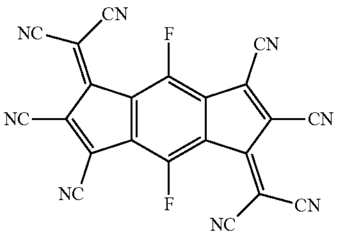
A48
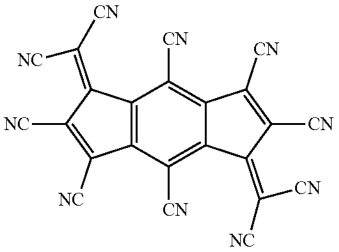
A49
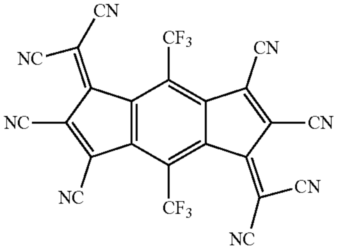
A50
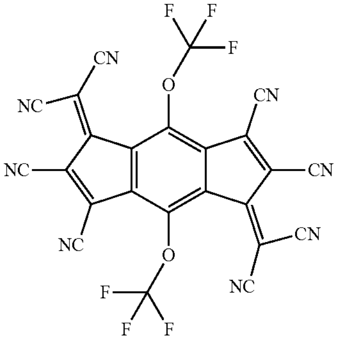
A51
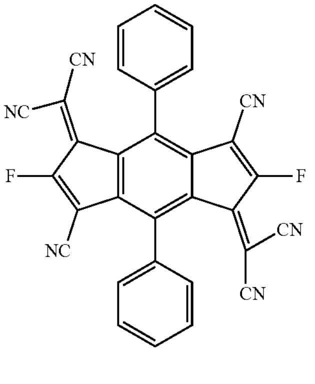
-continued
A52
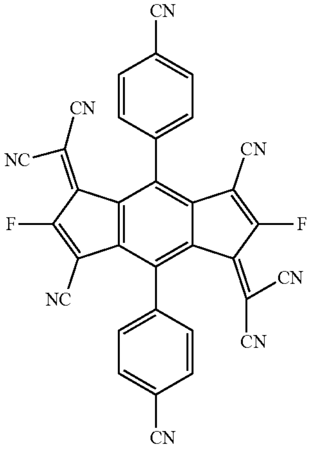
A53
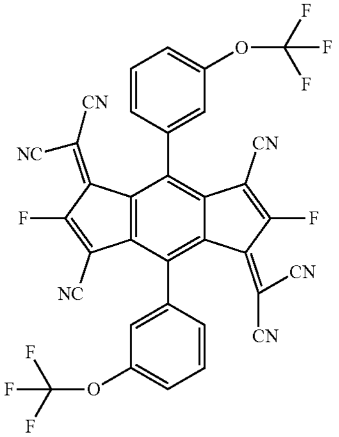
A54
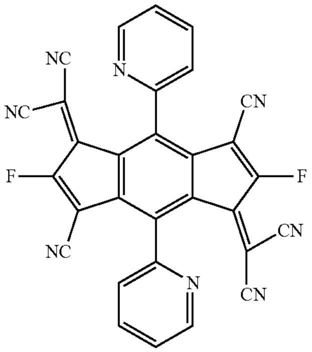
A55
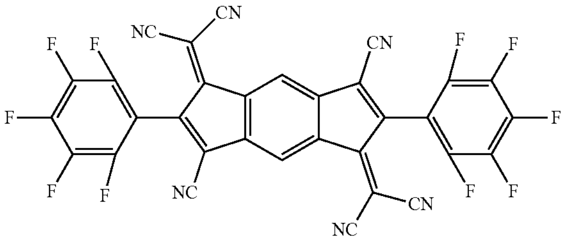

-continued
A56
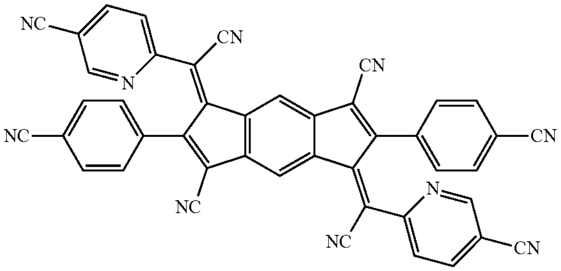
A57
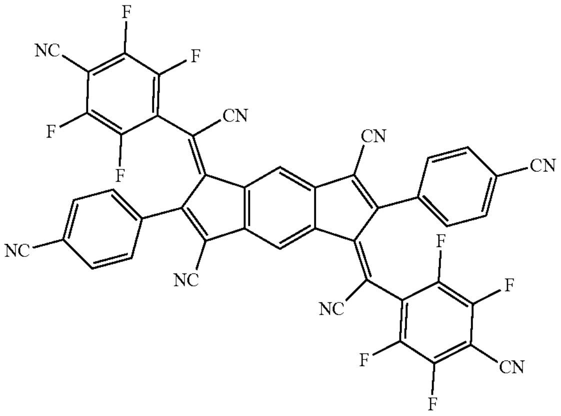
A58
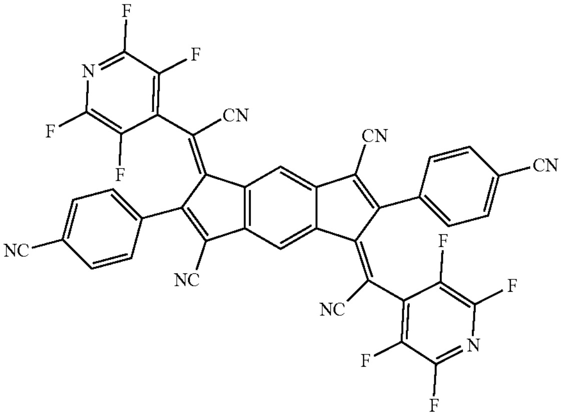
A59
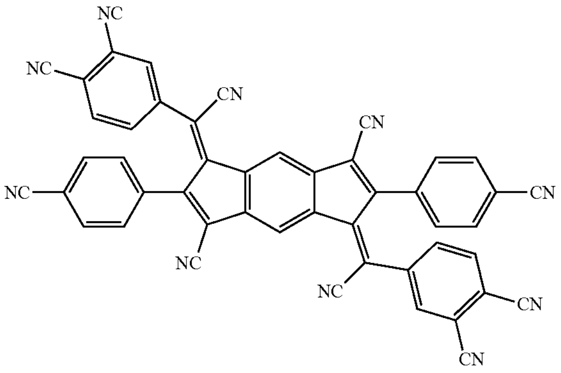
-continued
A60
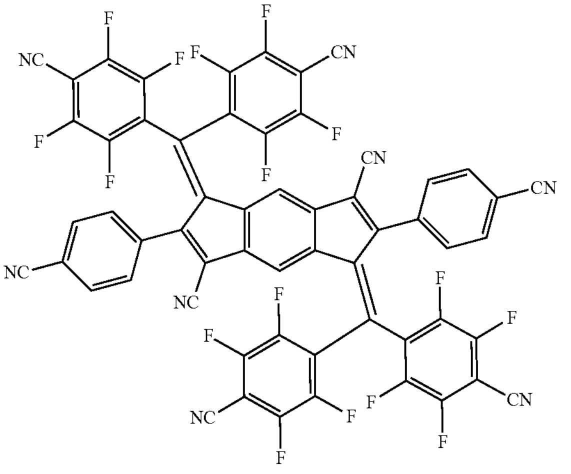
A61
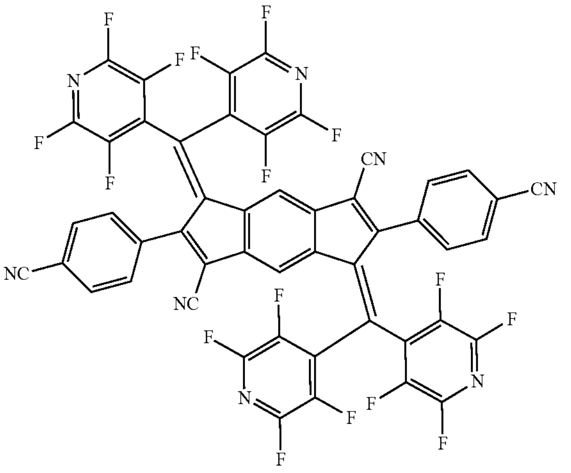
A62
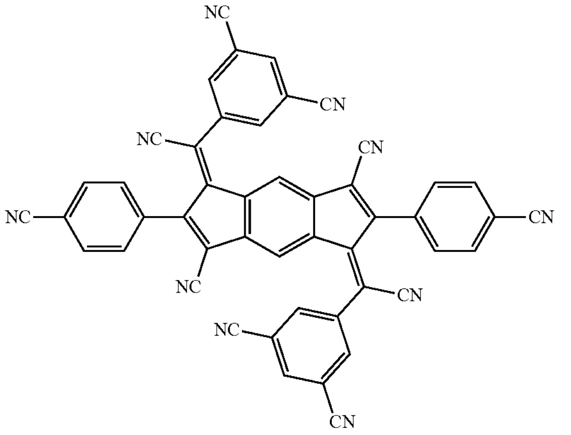

-continued
A63
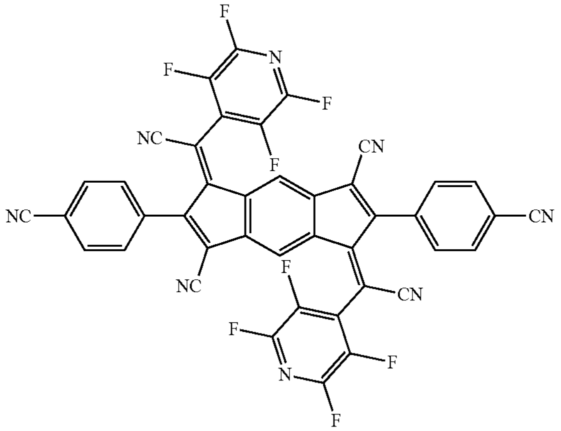
A64
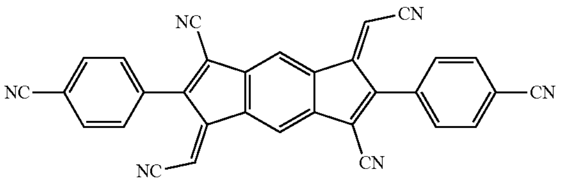
The compound represented by the above Chemical Formula 2 is represented by one among the following compounds:
B1
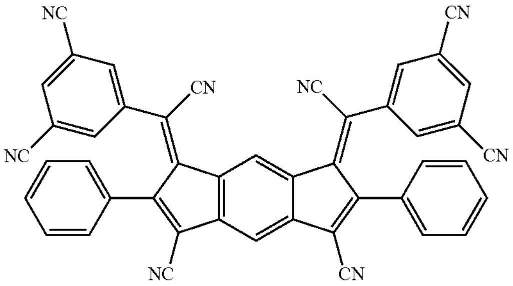
B2
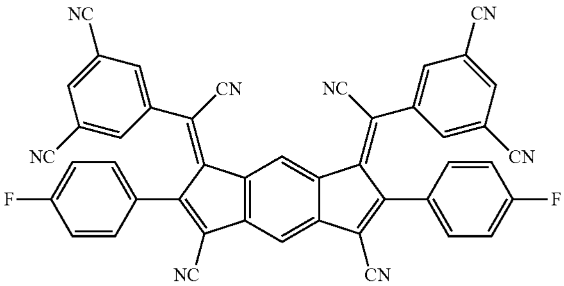
-continued
B3
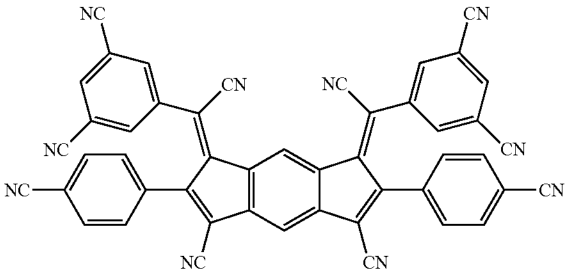
B4
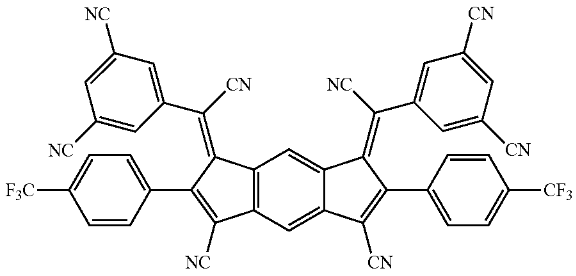
B5
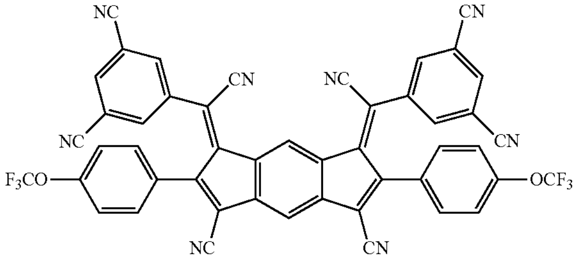
B6
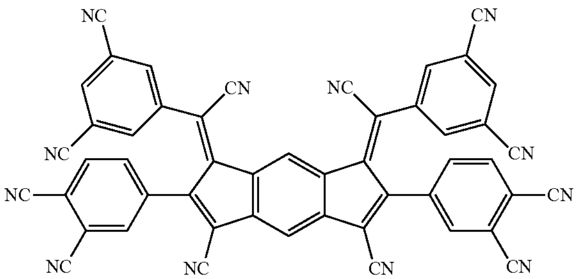
B7
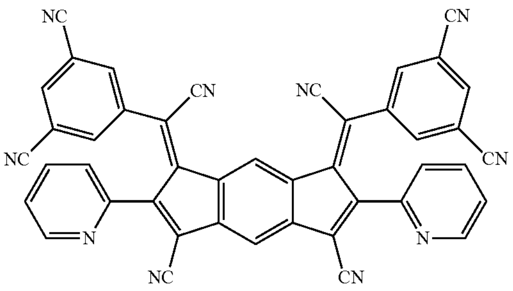

-continued
B8
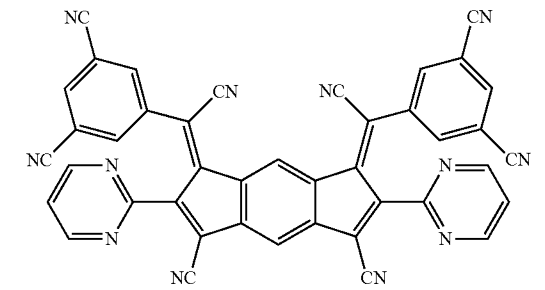
B9
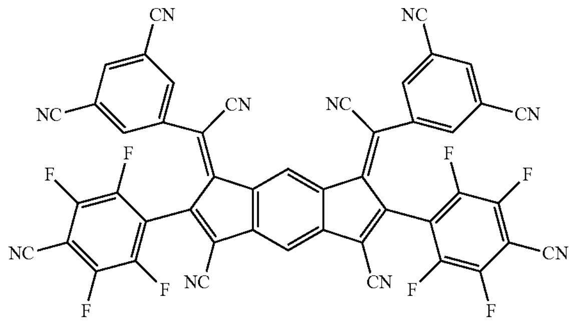
B10
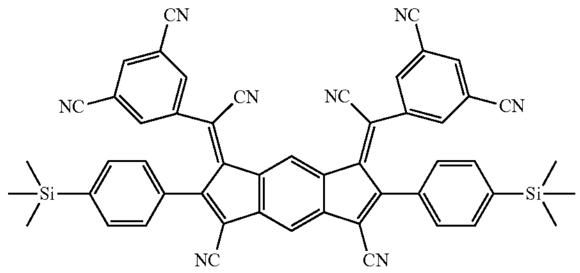
B11
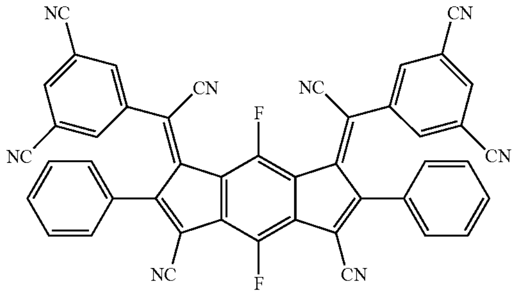
B12
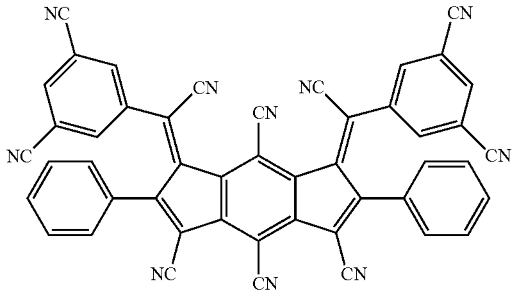
-continued
B13
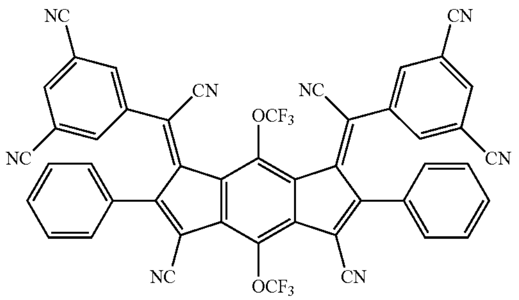
B14
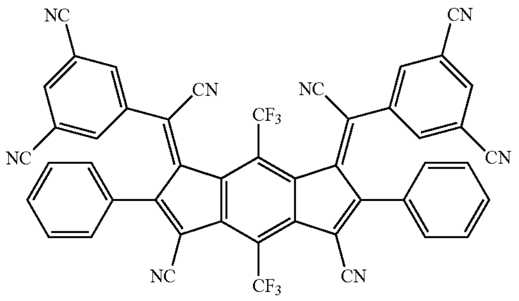
B15
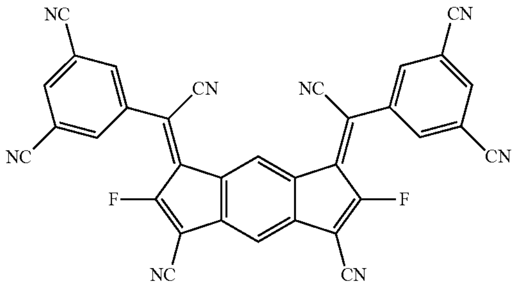
B16
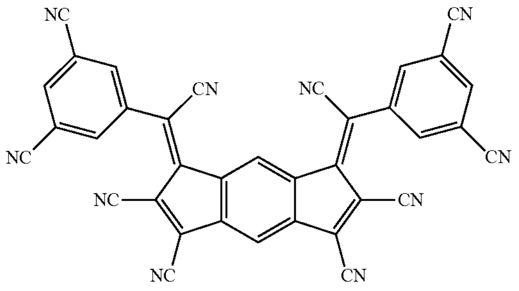
B17
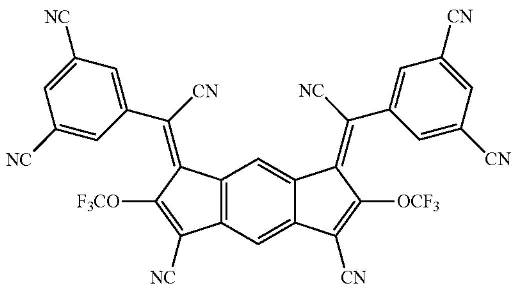

-continued
B18
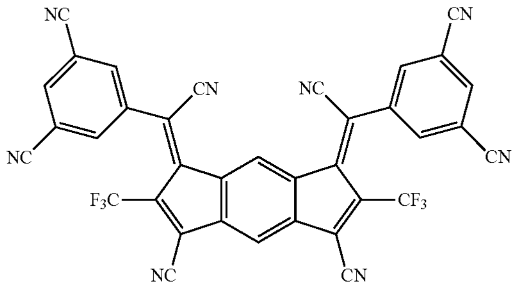
B19
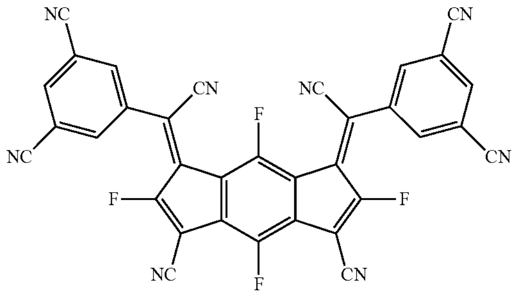
B20
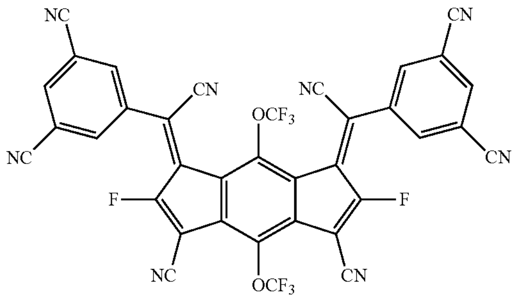
B21
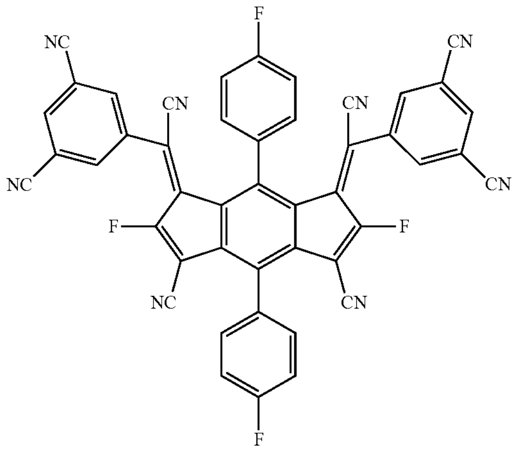
-continued
B22
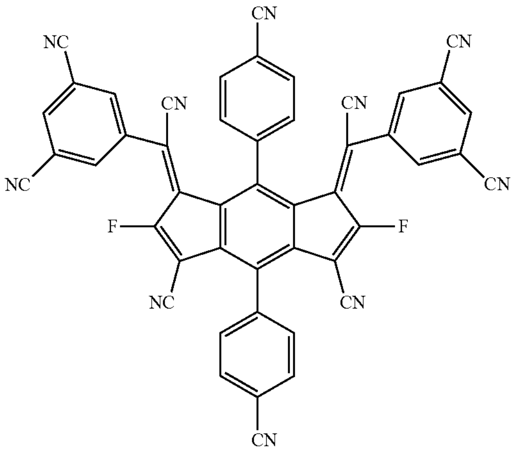
B23
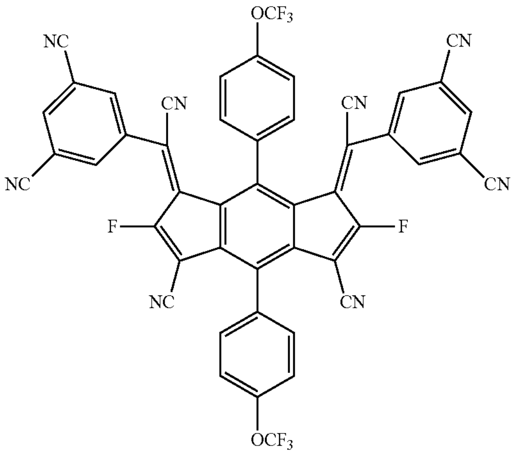
B24
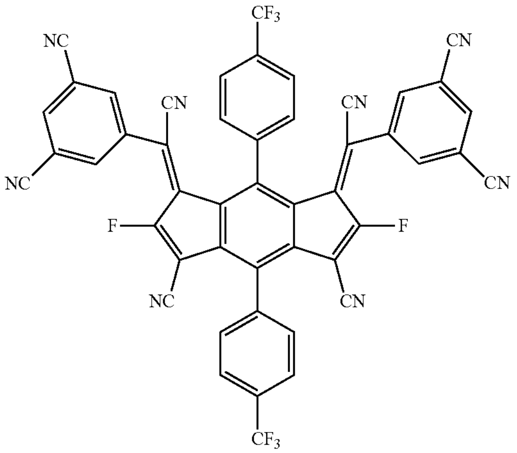

-continued
B25
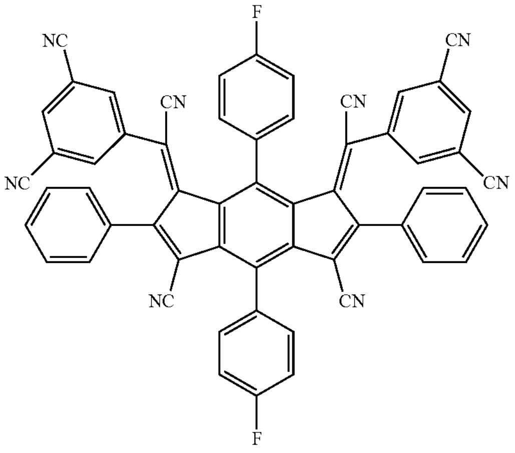
B26
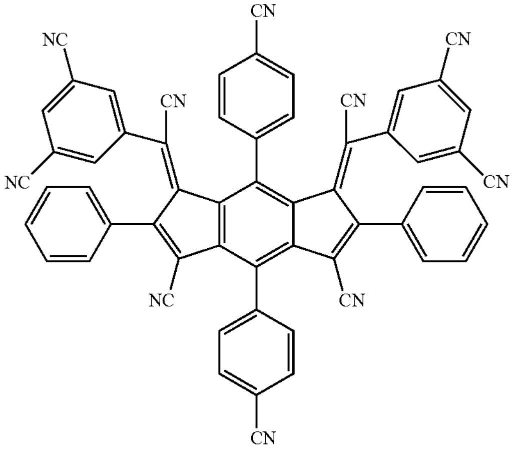
B27
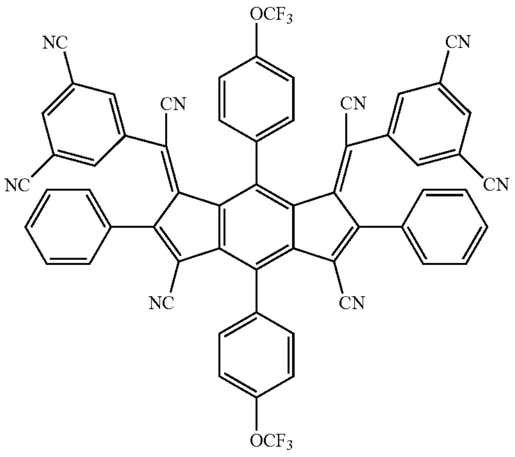
-continued
B28
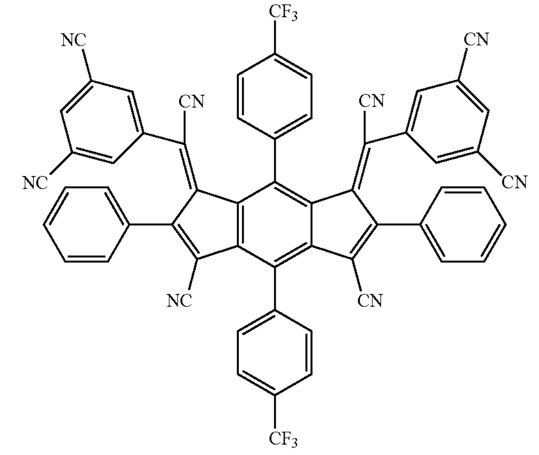
B29
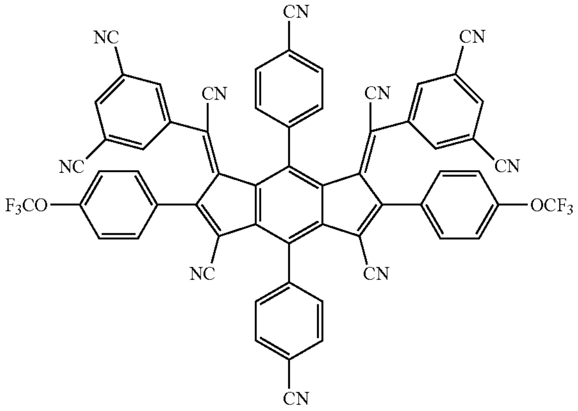
B30
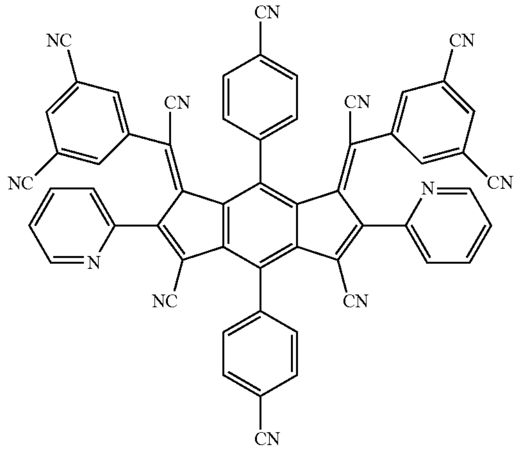
B31
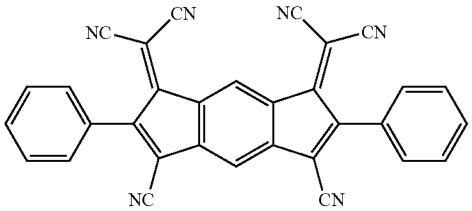

-continued
B32
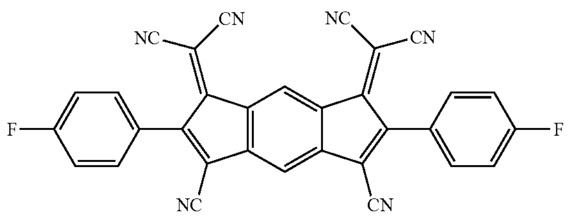
B33
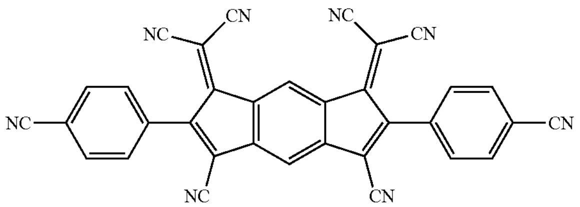
B34
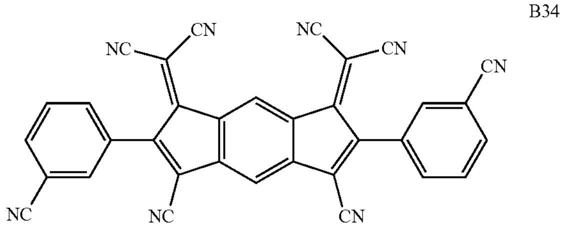
B35
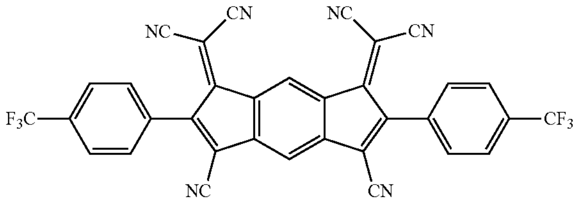
B36
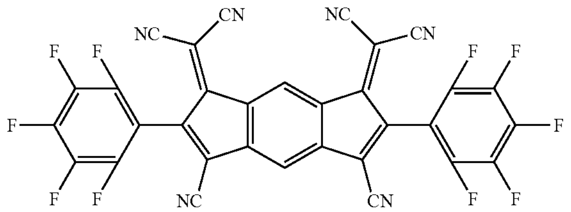
B37
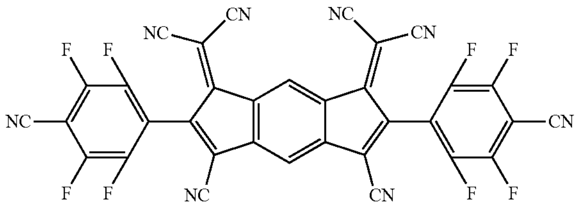
B38
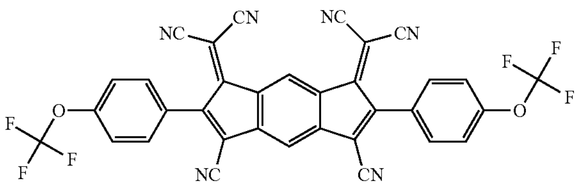
-continued
B39
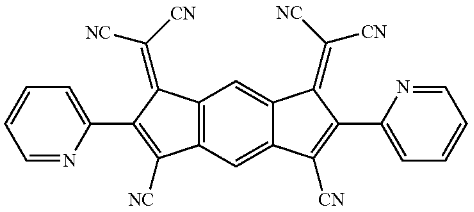
B40
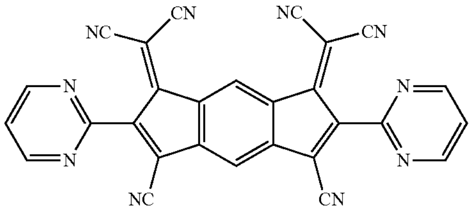
B41
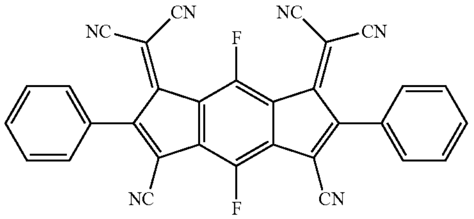
B42
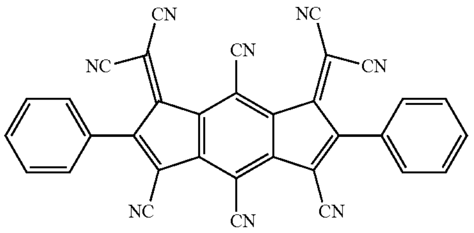
B43
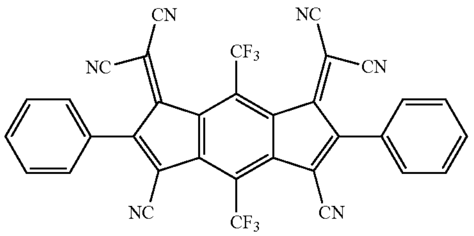
B44
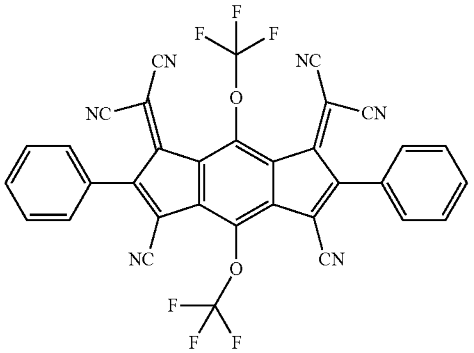

-continued
B45
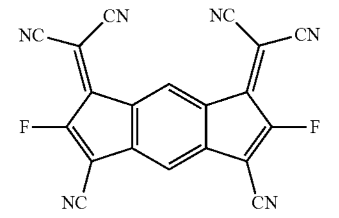
B46
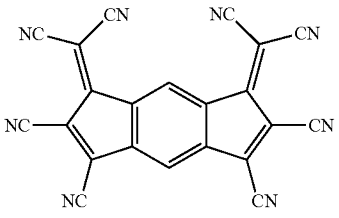
B47
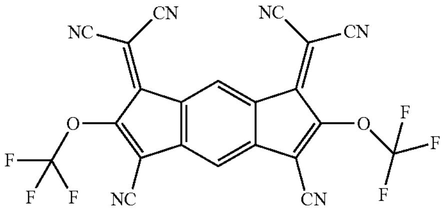
B48
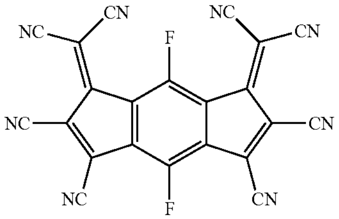
B49
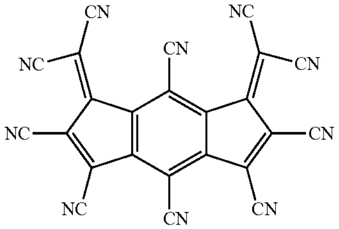
B50
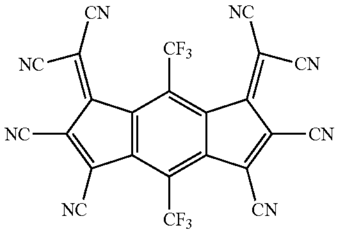
-continued
B51
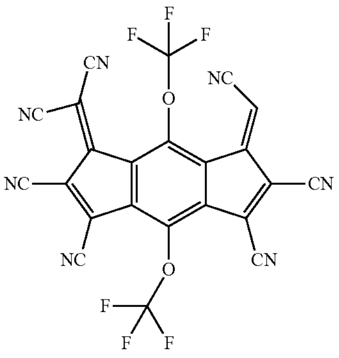
B52
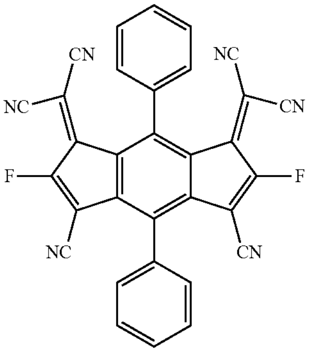
B53
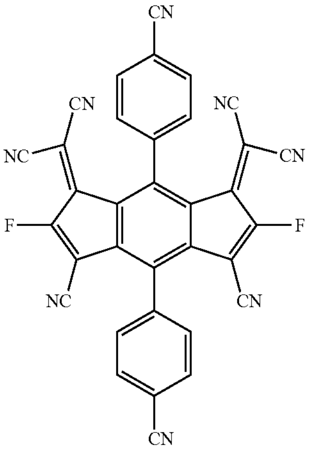
B54
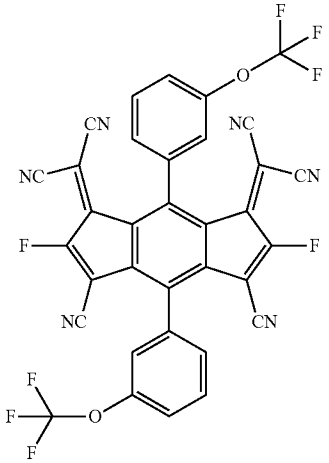

-continued

B55

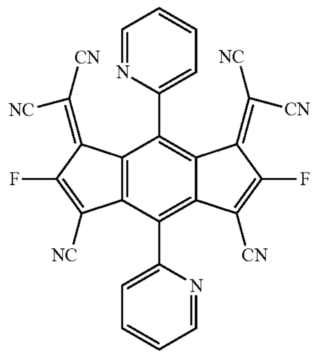

B56

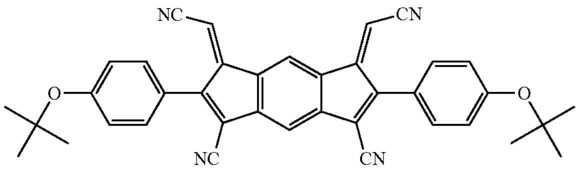

A dopant for the hole injection layer includes the compound.

The hole injection layer includes the compound.

A dopant for the P-type charge generation layer includes the compound.

The P-type charge generation layer includes the compound.

BRIEF DESCRIPTION OF THE DRAWINGS

The accompanying drawings, which are included to provide a further understanding of the disclosure and are incorporated in and constitute a part of this specification, illustrate embodiments of the disclosure and together with the description serve to explain the principles of the disclosure.

DETAILED DESCRIPTION OF THE EMBODIMENTS

Figure 1:
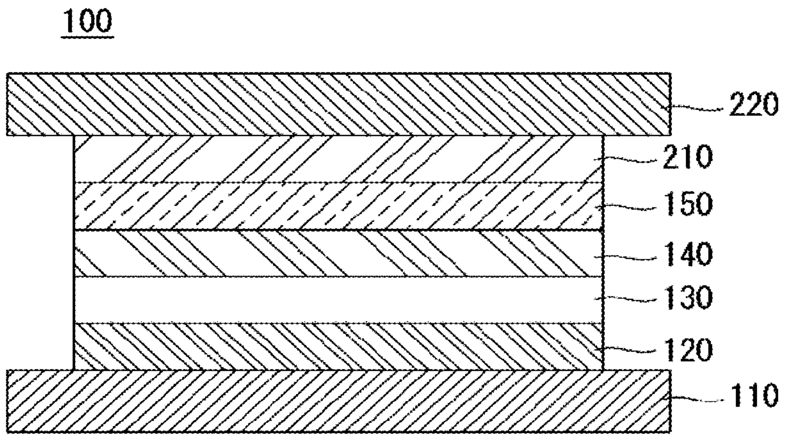
FIG. 1 is a cross-sectional view showing an organic light emitting display device according to a first exemplary embodiment of the present disclosure.

The advantages and features of the present disclosure and methods for accomplishing the same may be understood more readily by reference to the following detailed descriptions of exemplary embodiments and the accompanying drawings. The present disclosure may, however, be embodied in many different forms and should not be construed as being limited to the exemplary embodiments set forth herein. Rather, these exemplary embodiments are provided so that this disclosure will be thorough and complete and will fully convey the concept of the present disclosure to those skilled in the art, and the present disclosure is defined by the appended claims.

The shapes, sizes, percentages, angles, numbers, etc shown in the figures to describe the exemplary embodiments of the present disclosure are merely examples and not limited to those shown in the figures. Like reference numerals denote like elements throughout the specification. In describing the present disclosure, detailed descriptions of related well-known technologies will be omitted to avoid unnecessary obscuring the present disclosure. When the terms 'comprise', 'have', 'consist of' and the like are used, other parts may be added as long as the term 'only' is not used. The singular forms may be interpreted as the plural forms unless explicitly stated.

The elements may be interpreted to include an error margin even if not explicitly stated.

When the position relation between two parts is described using the terms 'on', 'over', 'under', 'next to' and the like, one or more parts may be positioned between the two parts as long as the term 'immediately' or 'directly' is not used.

When the temporal relationship between two events is described using the terms 'after', 'following', 'next', 'before' and the like, the two events may not occur in succession as long as the term 'immediately' or 'directly' is not used.

It will be understood that, although the terms first, second, etc., may be used to describe various elements, these elements should not be limited by these terms. These terms are only used to distinguish one element from another element. Thus, a first element discussed below could be termed a second element without departing from the technical spirit of the present disclosure.

The features of various exemplary embodiments of the present disclosure may be combined with one another either partly or wholly, and may technically interact or work together in various ways. The exemplary embodiments may be carried out independently or in combination with one another.

Hereinafter, various exemplary embodiments of the present disclosure will be described in detail with reference to the accompanying drawings.

FIG. 1 is a cross-sectional view showing an organic light emitting display device according to a first exemplary embodiment of the present disclosure. All the components of the organic light emitting display device according to all embodiments of the present disclosure are operatively coupled and configured.

Referring to FIG. 1, an organic light emitting display device 100 according to the first exemplary embodiment of the present disclosure comprises an anode 110, a hole injection layer 120, a hole transport layer 130, an light emitting layer 140, an electron transport layer 150, an electron injection layer 210, and a cathode 220.

The anode 110 is a hole injection electrode, and may be formed of one among ITO (indium tin oxide), IZO (indium zinc oxide), or ZnO (zinc oxide) having a high work function. Also, if the anode 110 is a reflective electrode, the anode 110 may further comprise a reflective layer formed of one among aluminum (Al), silver (Ag), or nickel (Ni) under a layer formed of one among ITO, IZO, or ZnO.

The hole injection layer 120 is formed on the anode 110. The hole injection layer 120 has to comprise a strong electron-attracting substituent, in order to make LUMO energy level of the hole injection layer similar to or lower than the HOMO energy level of the host of the hole injection layer or the HOMO energy level of the hole transport layer.

However, compounds comprising an electron-attracting substituent are hard to synthesize because of the electron-attracting substituents, and are not easy to develop due to their low thermal and deposition stability. In view of this, the present inventors conducted various tests to improve the hole injection properties and the device's efficiency and lifetime by forming a hole injection layer of a material that ensures process stability and comprises an electron-attracting substituent.

Through a number of tests or experiments which were performed on materials that do not affect the lifetime or efficiency of the organic light emitting display device and that cause no rise in operating voltage, the present inventors developed compounds that can exhibit hole injection properties by ensuring process stability and comprising an electron-attracting substituent. In the present disclosure, a hole injection layer is formed using a compound comprising indene as a core and an electron-attracting substituent. The composition and deposition of the compound is simplified because indene provides process stability against heat or deposition. Moreover, the compound of this disclosure can improve the hole injection properties by comprising an electron-attracting substituent attached to the core and making the LUMO energy level of the compound similar to or lower than the HOMO energy level of the host of the hole injection layer 120, the host of a P-type charge generation layer, or the hole transport layer.

Accordingly, the hole injection layer 120 of this disclosure comprises a compound represented by the following Chemical Formula 1 or 2:

[Chemical Formula 1]

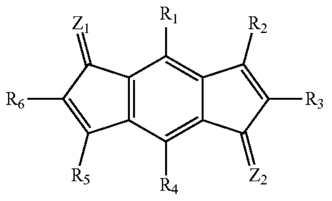

[Chemical Formula 2]

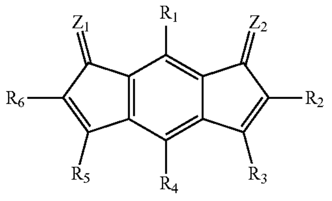

where $R_1$ to $R_6$ each independently represents one among a hydrogen atom, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted or unsubstituted alkyl group with 1 to 12 carbon atoms, a substituted or unsubstituted alkoxy group with 1 to 12 carbon atoms, a substituted or unsubstituted ether group with 1 to 12 carbon atoms, a cyano group, a fluorine group, a trifluoromethyl group, a trifluoromethoxy group, and a trimethylsilyl group, and at least one among $R_1$ to $R_6$ comprises a cyano group.

$Z_1$ and $Z_2$ are independently represented by the following Chemical Formula 3:

[Chemical Formula 3]

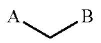

where A and B are independently represented by one among a hydrogen atom, a substituted or unsubstituted aryl group with 6 to 12 carbon atoms, a substituted or unsubstituted heteroaryl group with 1 to 12 carbon atoms, a substituted or unsubstituted alkyl group with 1 to 12 carbon atoms and 1 to 4 heteroatoms one among O, N, S, and Si, a substituted or unsubstituted alkoxy group with 1 to 12 carbon atoms, a substituted or unsubstituted ether group with 1 to 12 carbon atoms, a cyano group, a fluorine group, a trifluoromethyl group, a trifluoromethoxy group, and a trimethylsilyl group.

The substituent of the aryl group, heteroaryl group, alkyl group, alkoxy group, and ether group may be one among an alkyl with 1 to 12 carbon atoms, an aryl with 6 to 15 carbon atoms, a hetero aryl with 1 to 15 carbon atoms and 1 to 4 heteroatoms one among O, N, S, and Si, a cyano group, a fluorine group, a trifluoromethyl group, a trifluoromethoxy group, and a trimethylsilyl group.

The compound represented by Chemical Formula 1 is represented by at least one among the following compounds:

A01

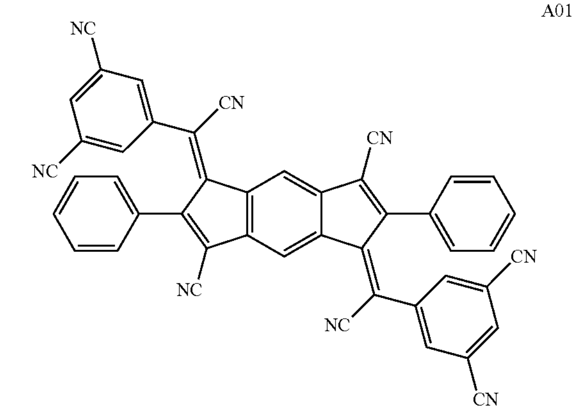

A02

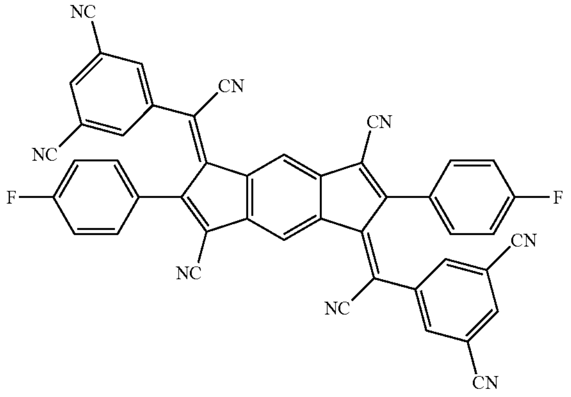

A03
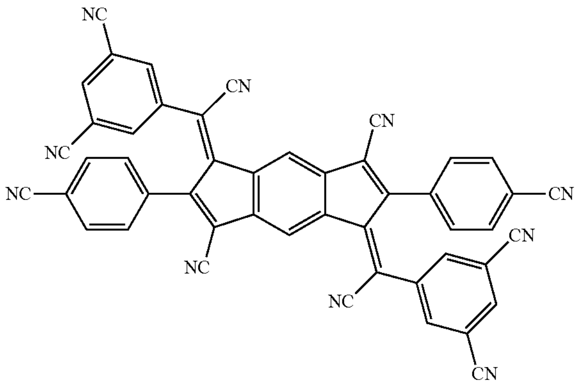
A04
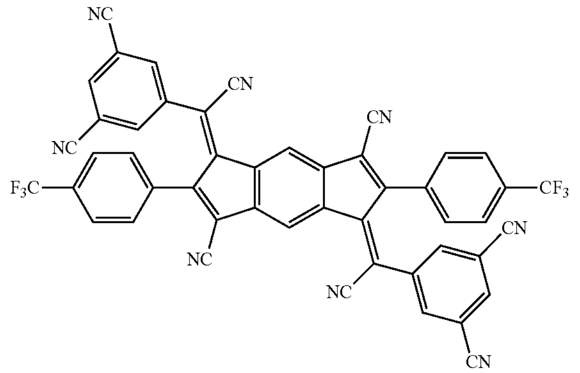
A05
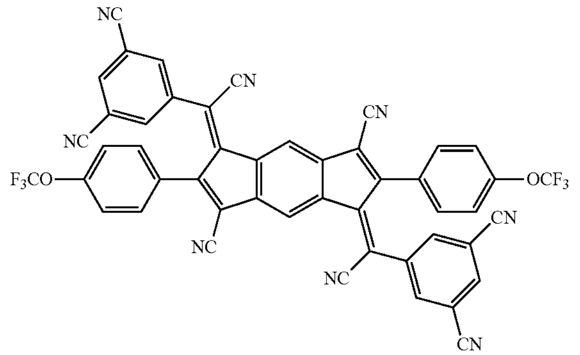
A06
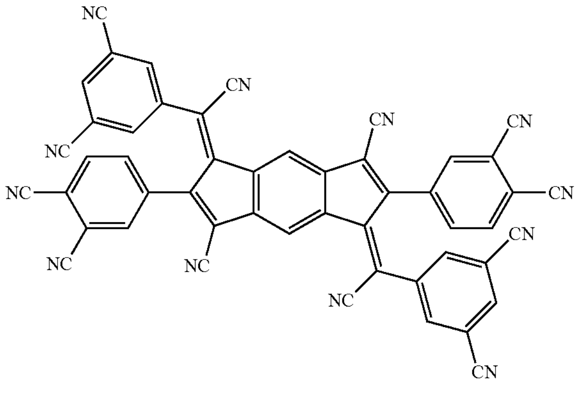
A07
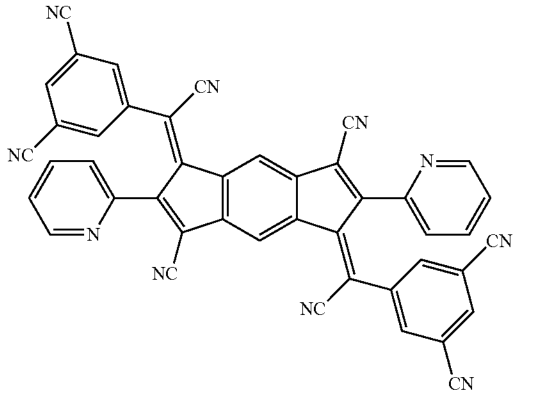
A08
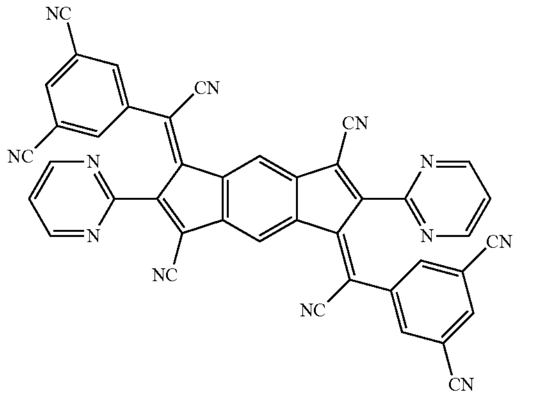
A09
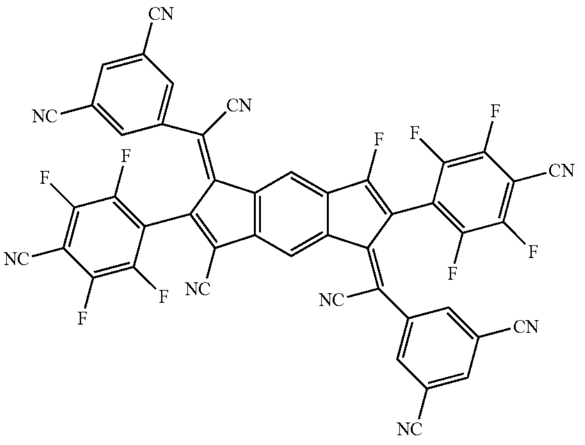

-continued
A10
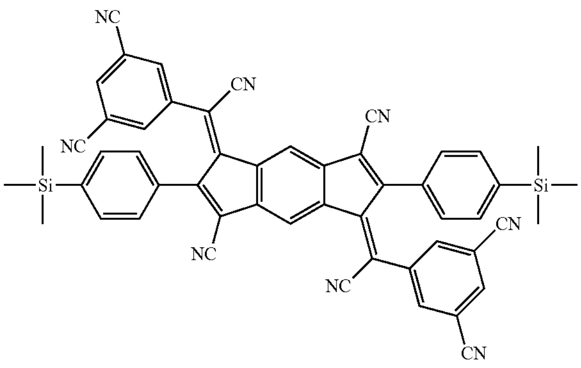
A11
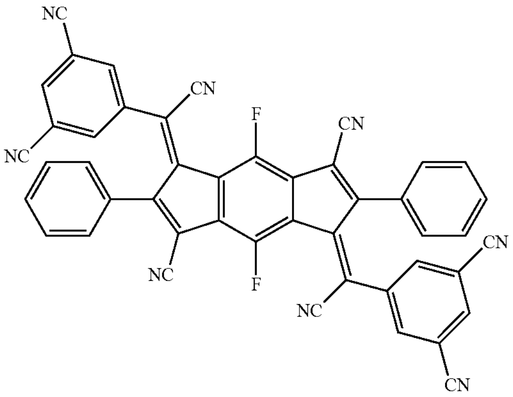
A12
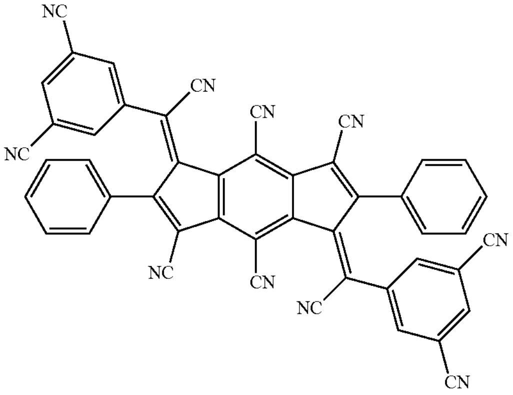
A13
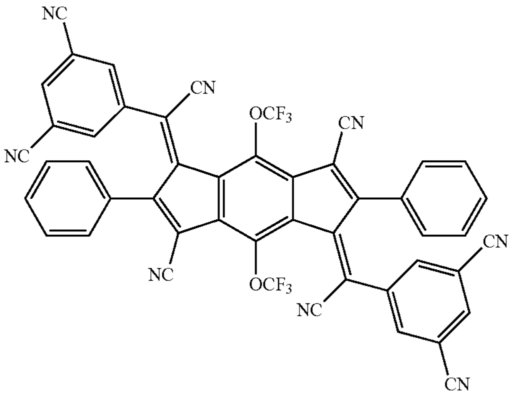
-continued
A14
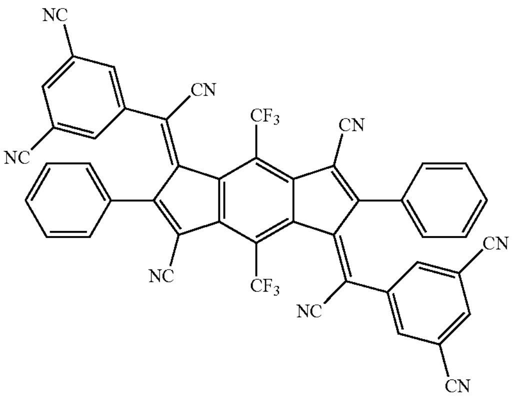
A15
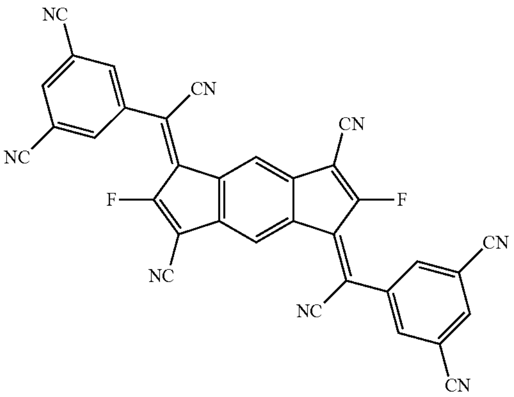
A16
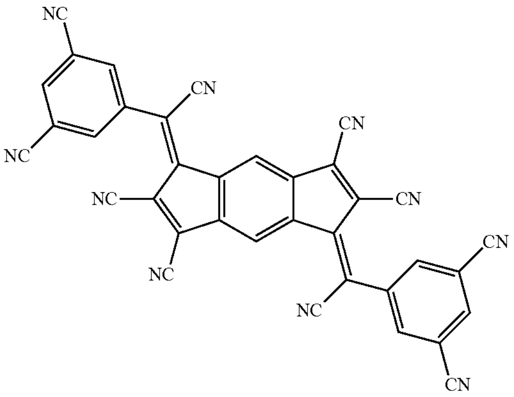

-continued
A17
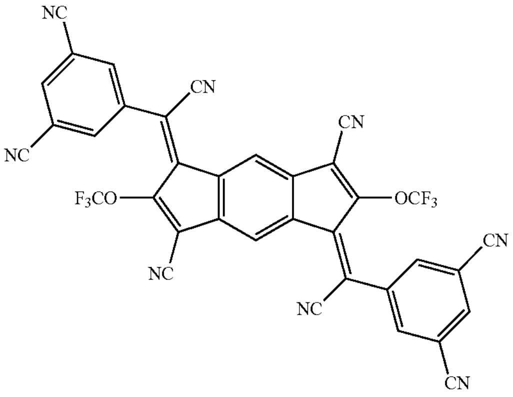
A18
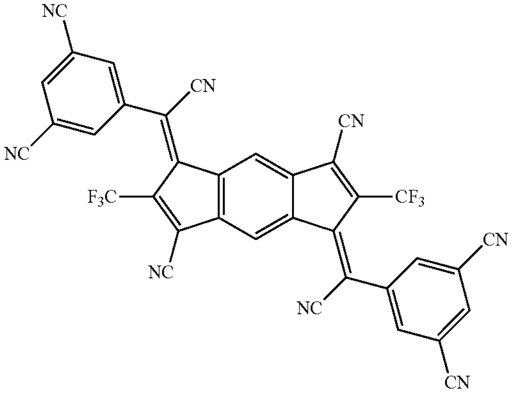
A19
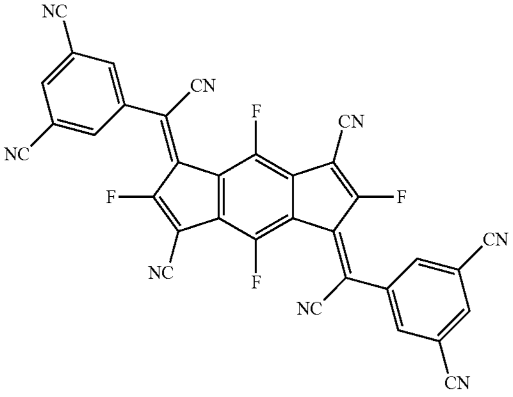
-continued
A20
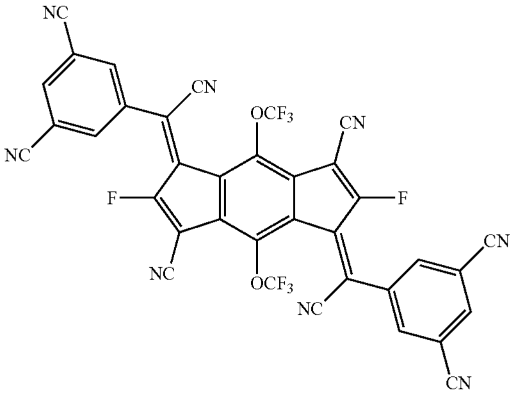
A21
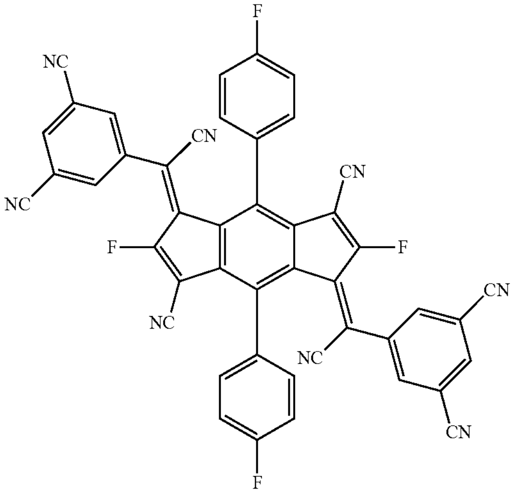
A22
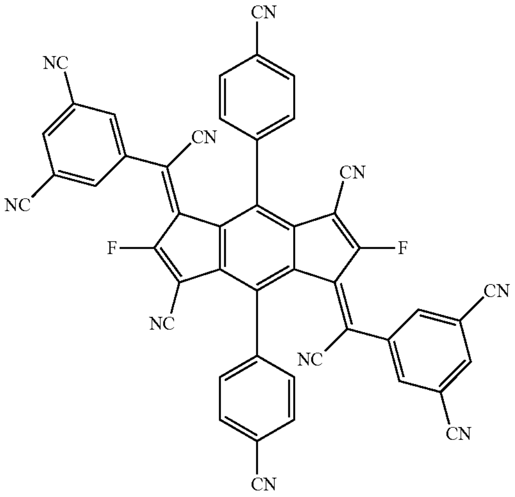

-continued
A23
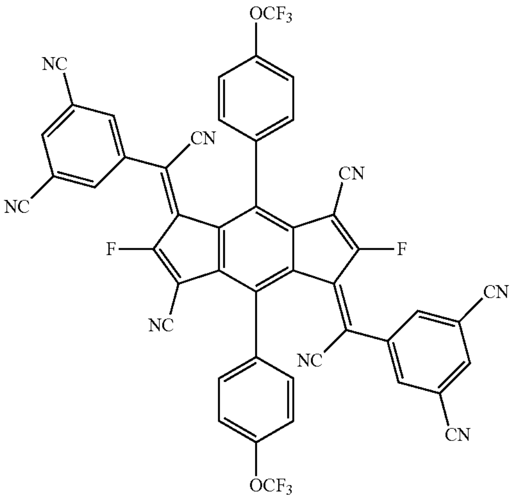
A24
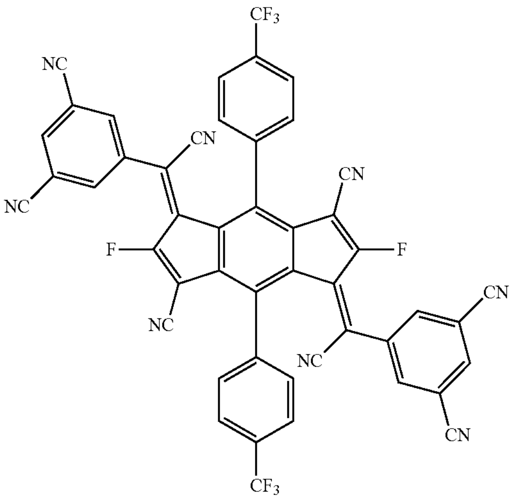
A25
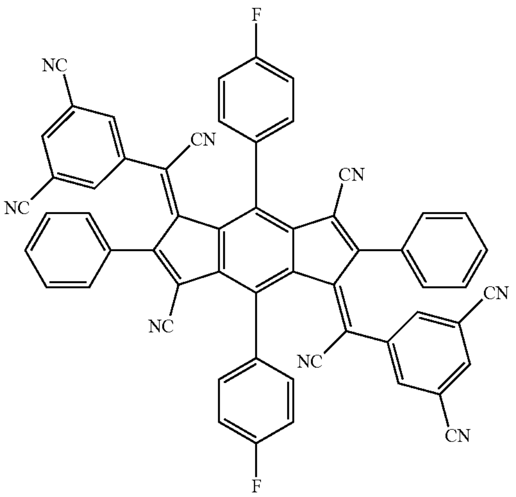
-continued
A26
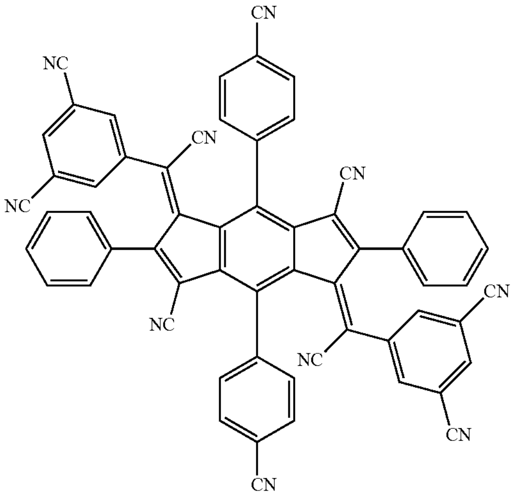
A27
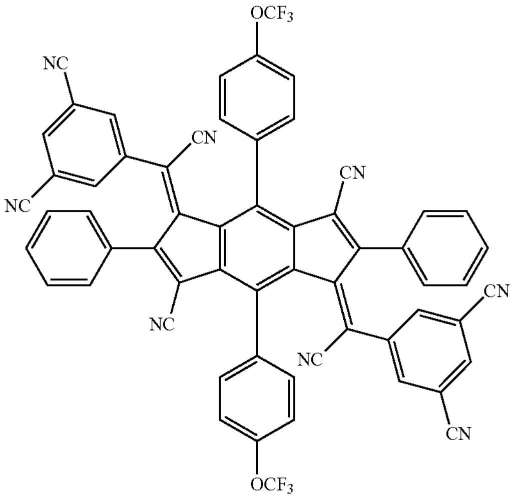
A28
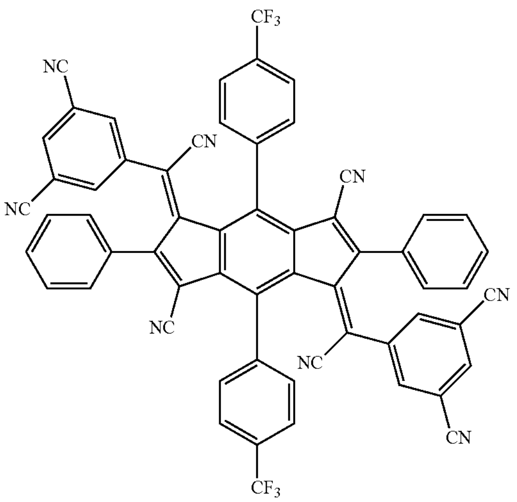

-continued
A29
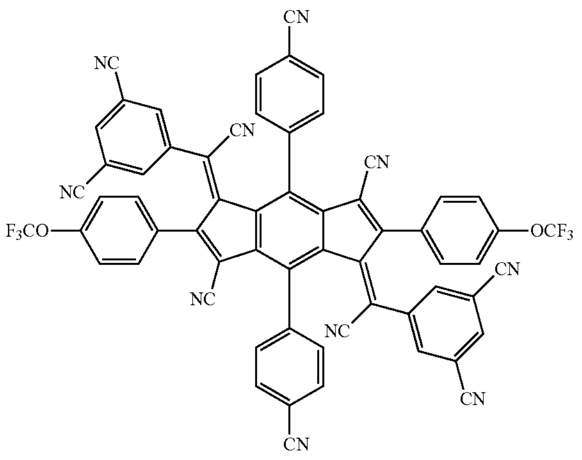
A30
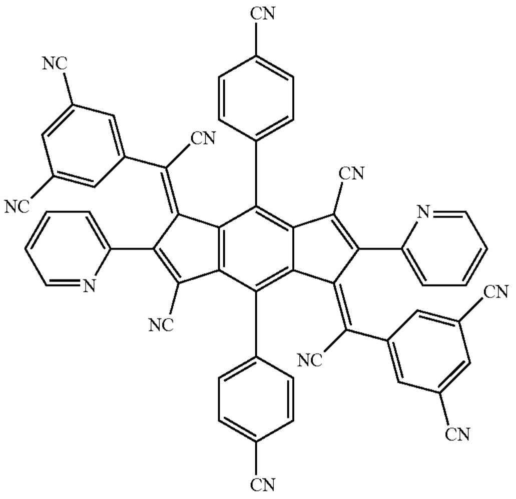
A31
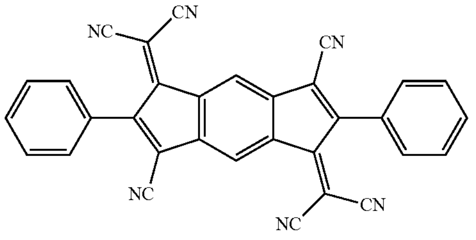
A32
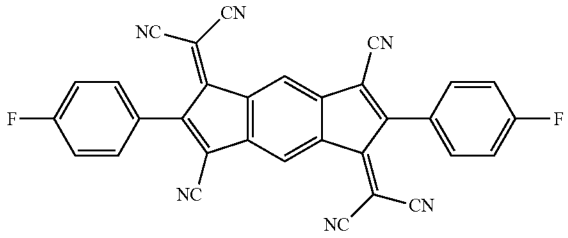
-continued
A33
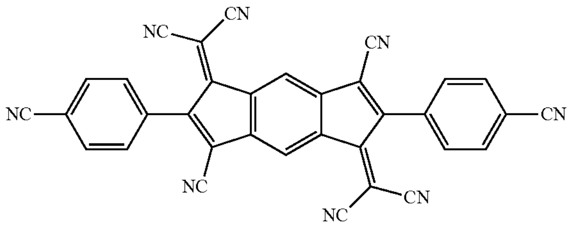
A34
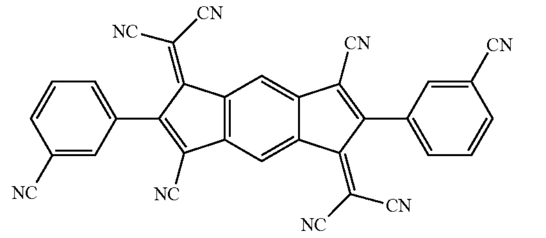
A35
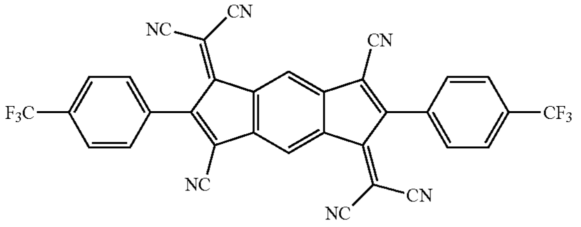
A36
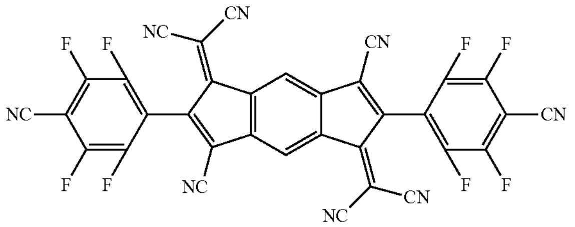
A37
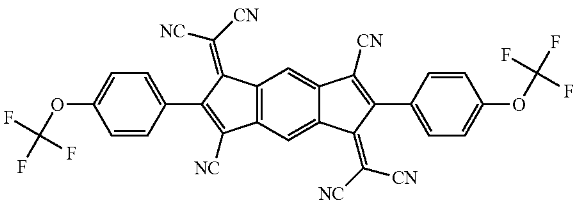
A38
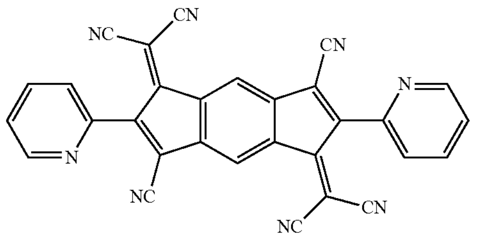

-continued
A39
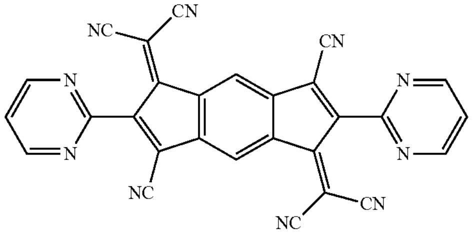
A40
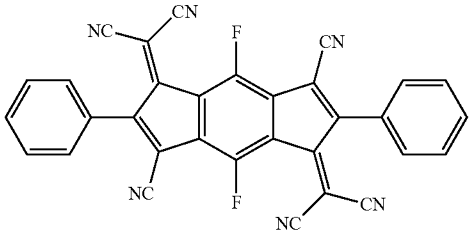
A41
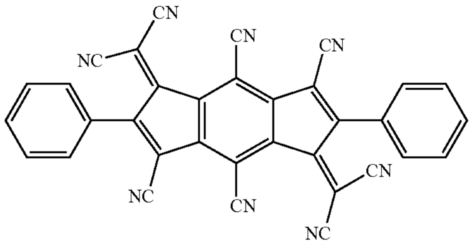
A42
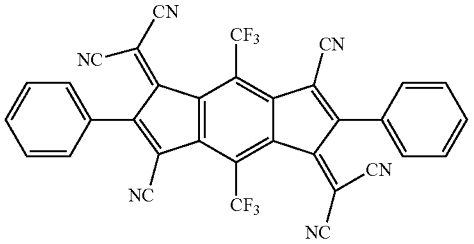
A43
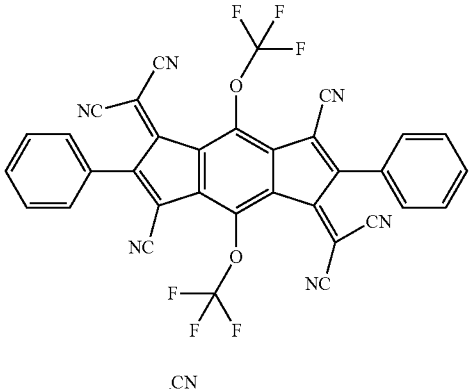
A44
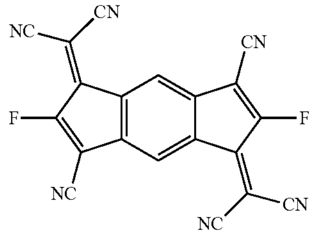
-continued
A45
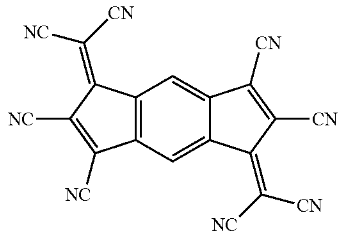
A46
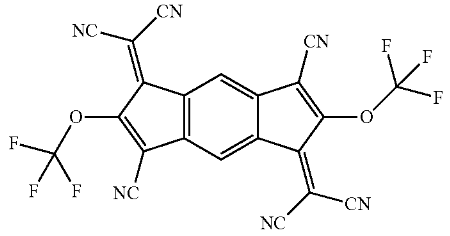
A47
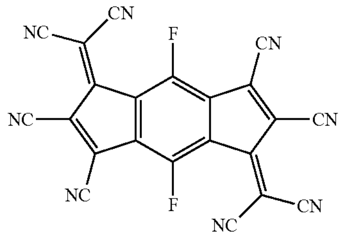
A48
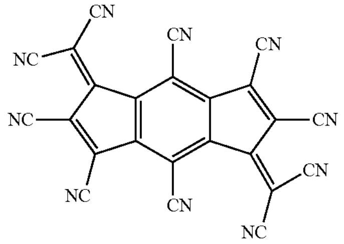
A49
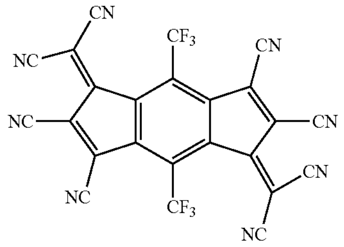
A50
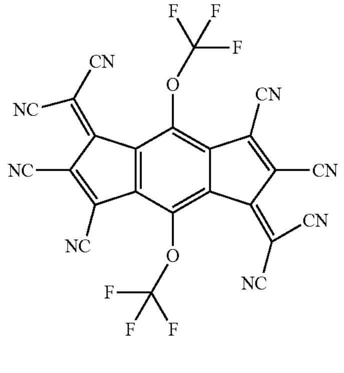

-continued
A51
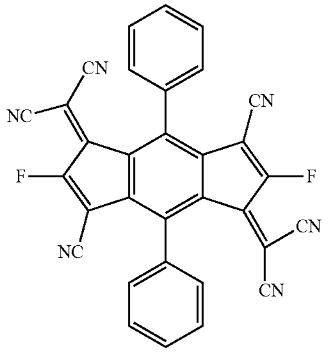
A52
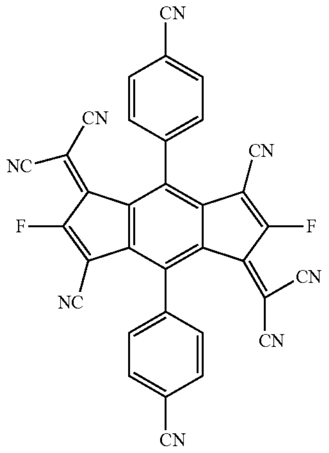
A53
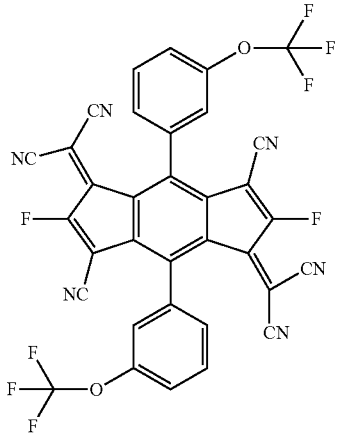
A54
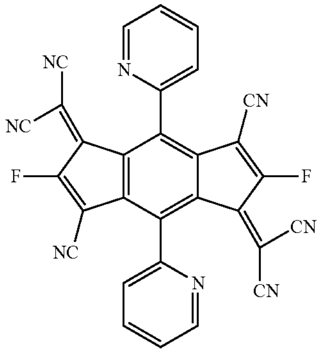
-continued
A55
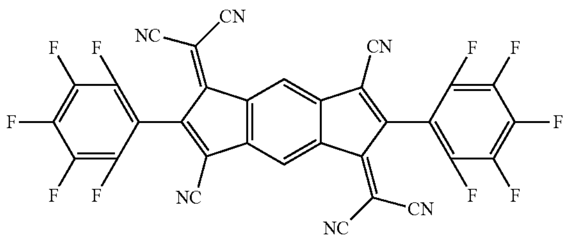
A56
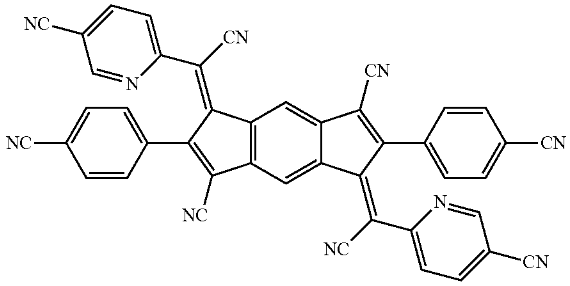
A57
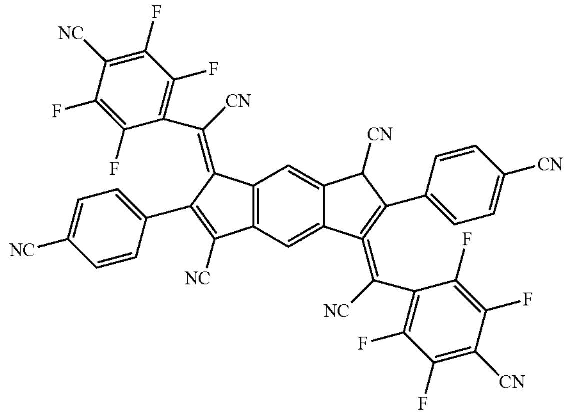
A58
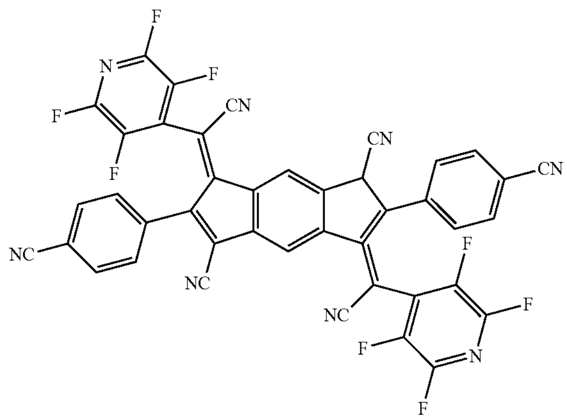

-continued
A59
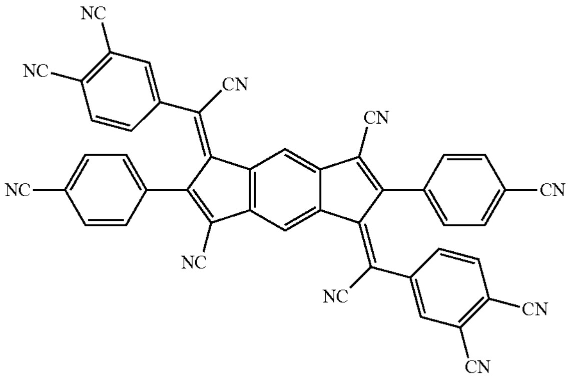
A60
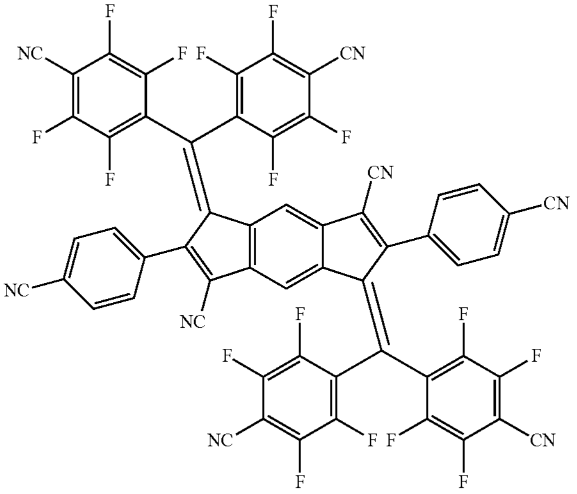
A61
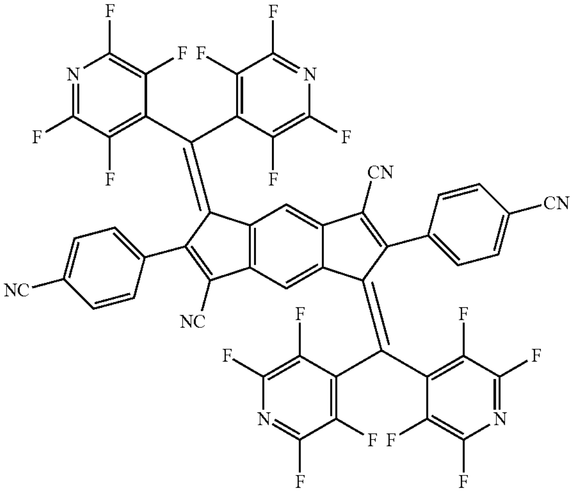
-continued
A62
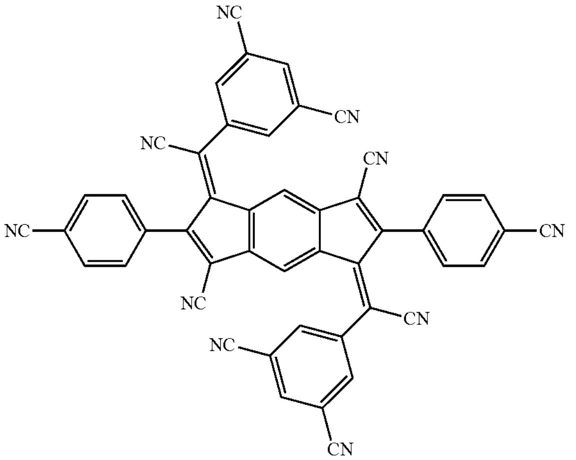
A63
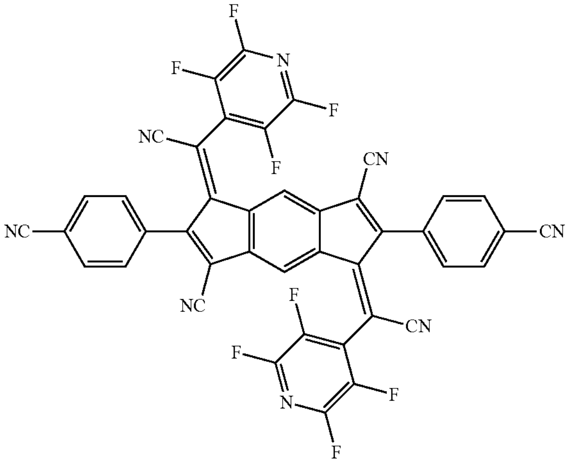
A64
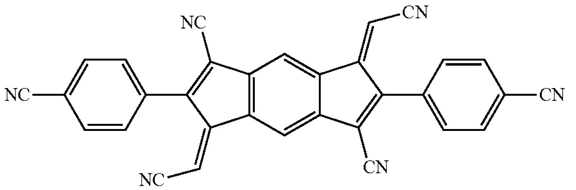
The compound represented by the above Chemical Formula 2 is represented by one among the following compounds:
B1
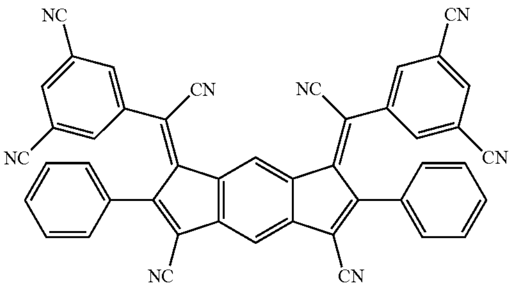

-continued
B2
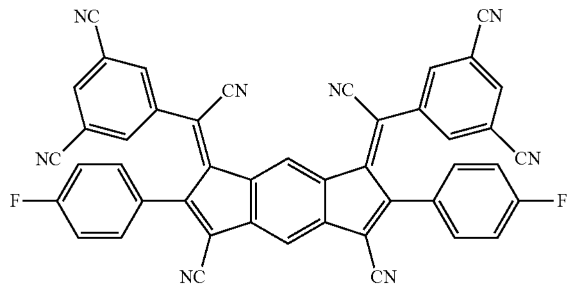
B3
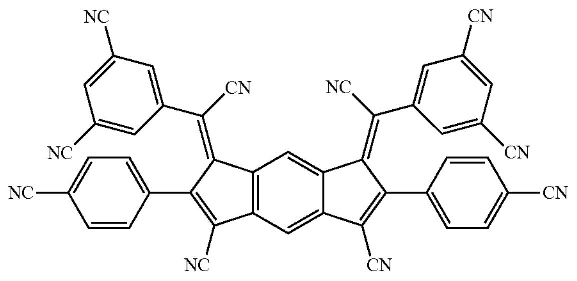
B4
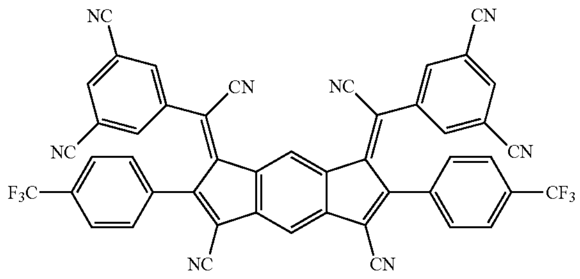
B5
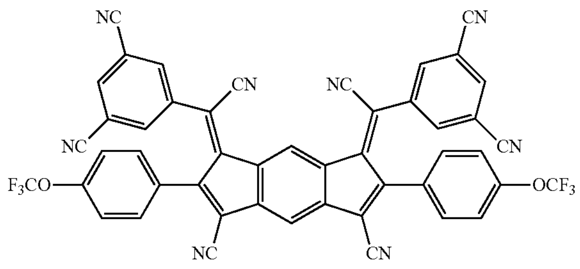
B6
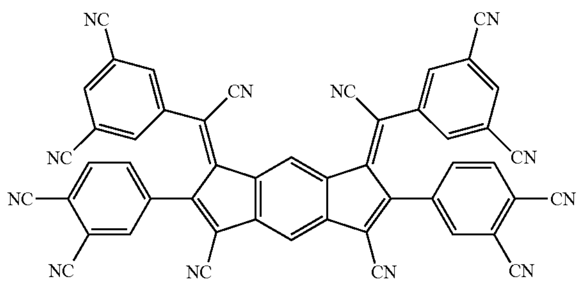
-continued
B7
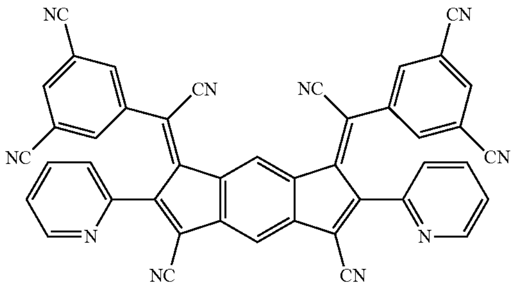
B8
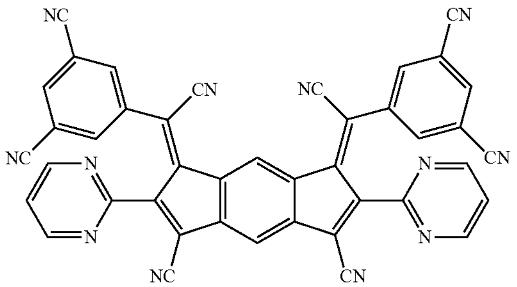
B9
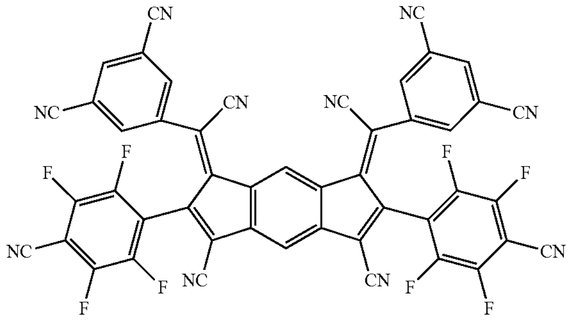
B10
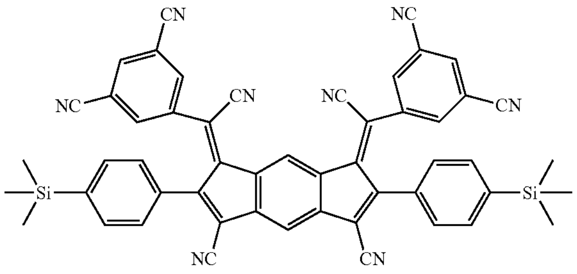
B11
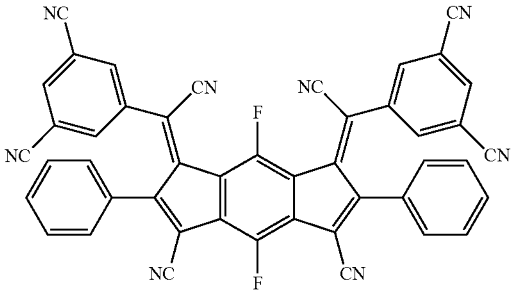

-continued
B12
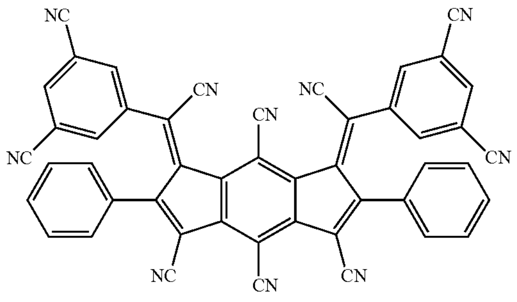
B13
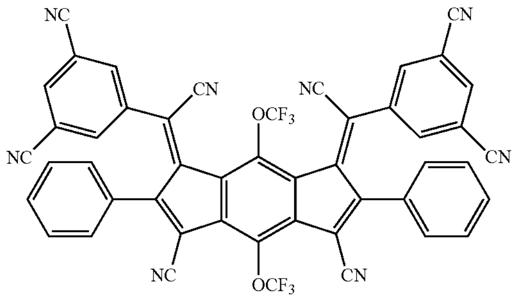
B14
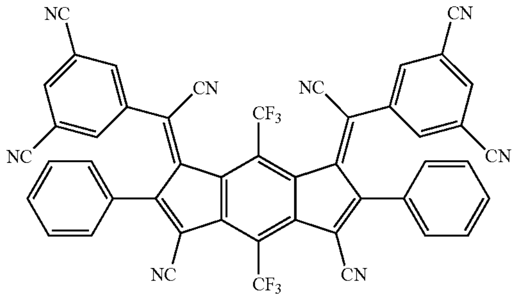
B15
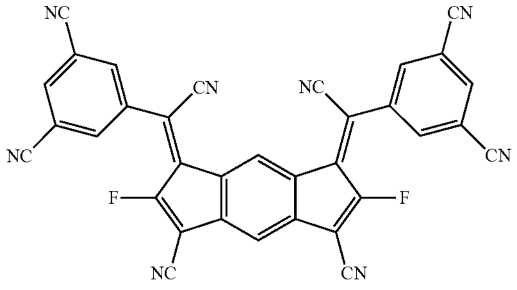
B16
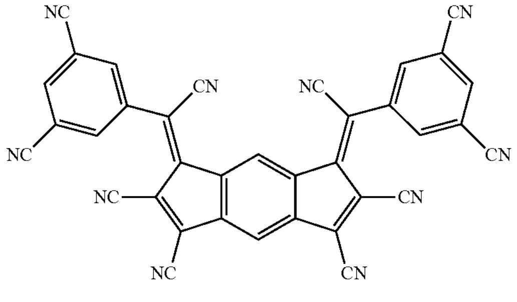
-continued
B17
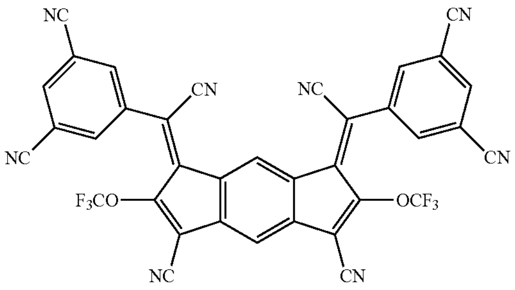
B18
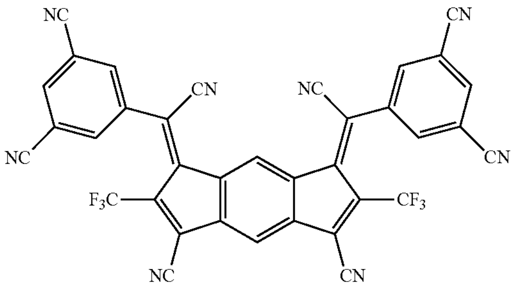
B19
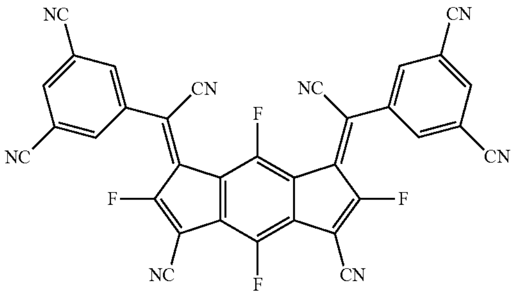
B20
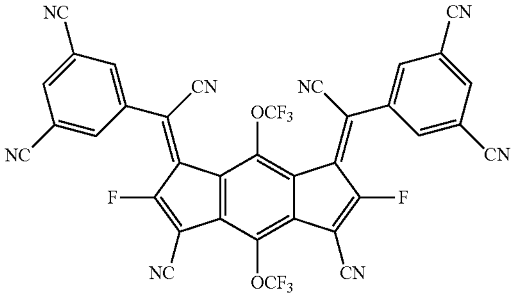

-continued
B21
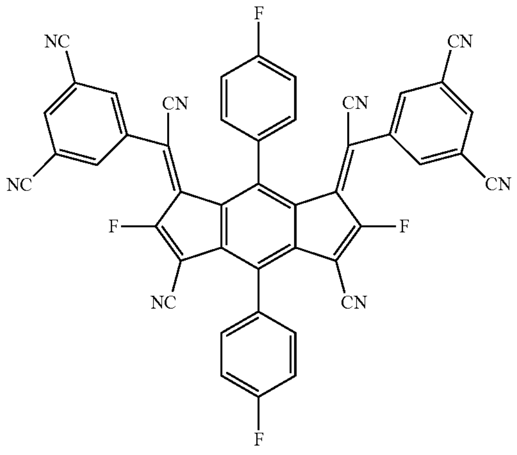
B22
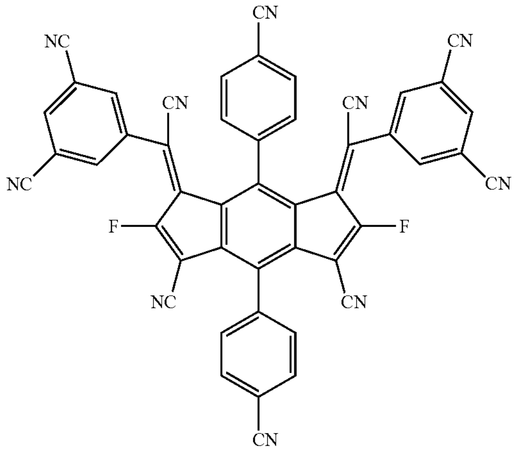
B23
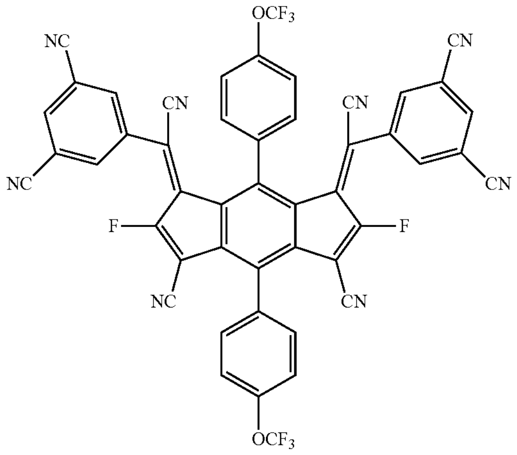
-continued
B24
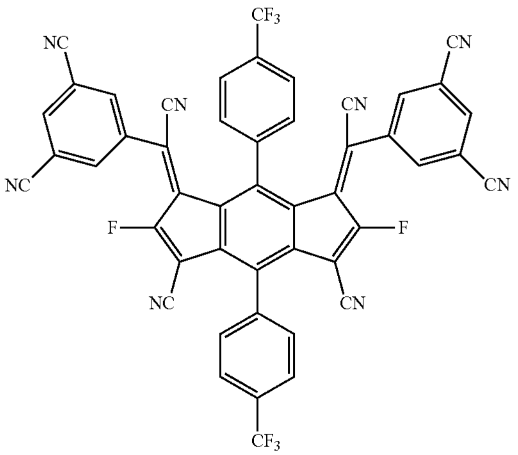
B25
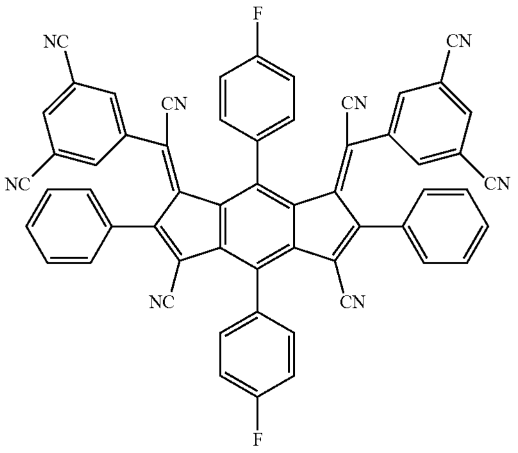
B26
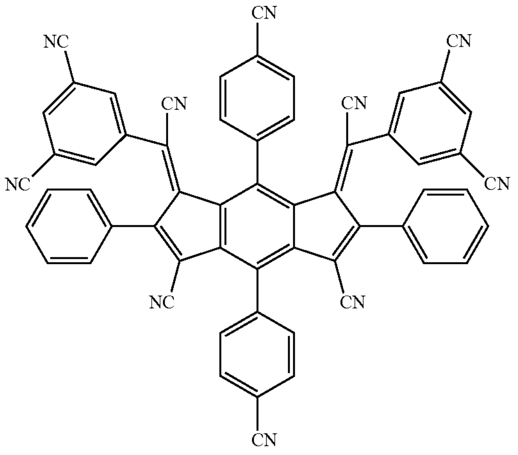

-continued
B27
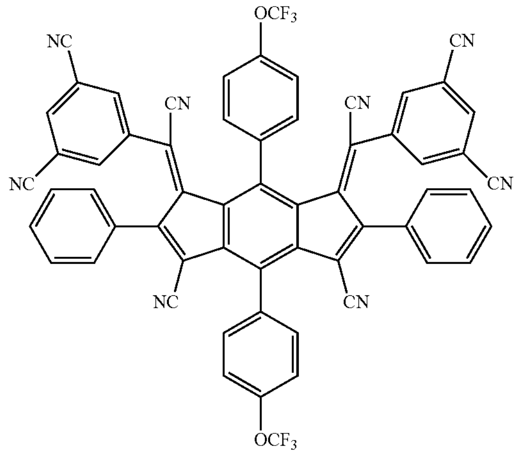
B28
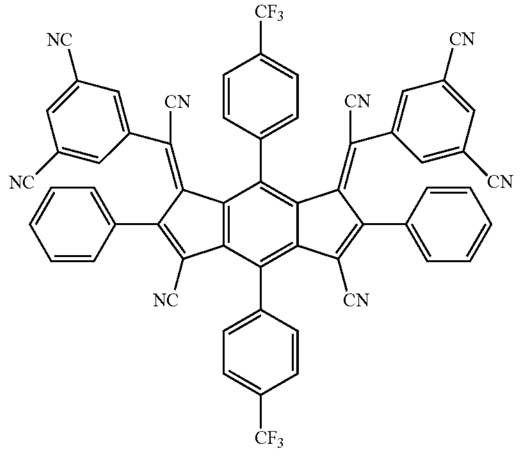
B29
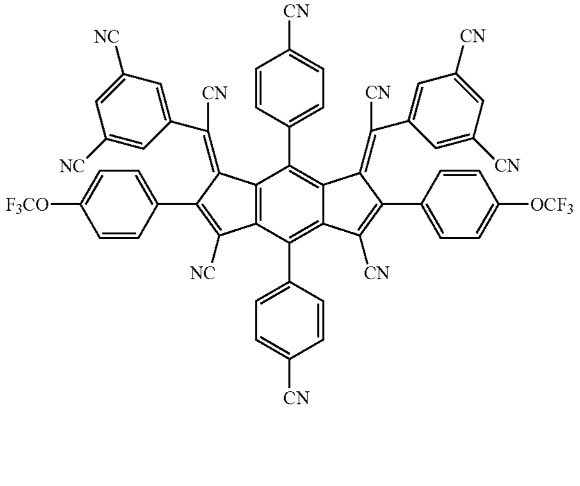
-continued
B30
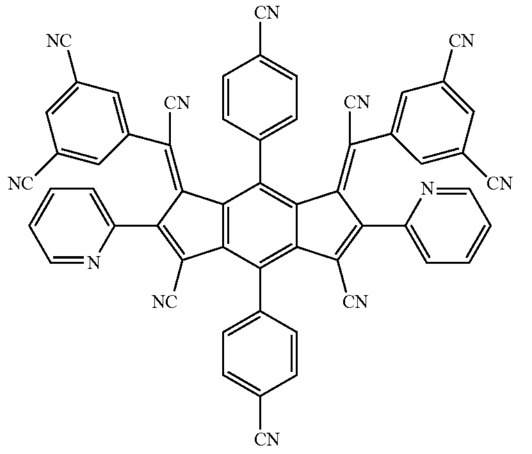
B31
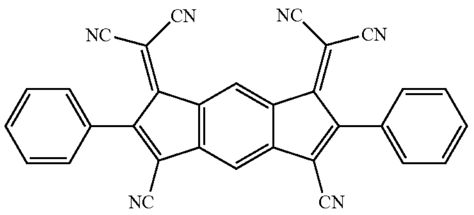
B32
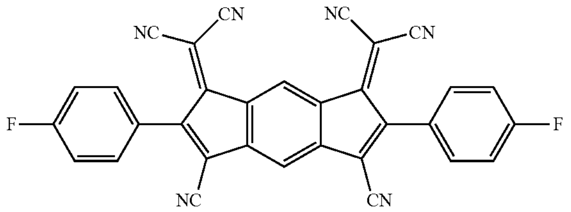
B33
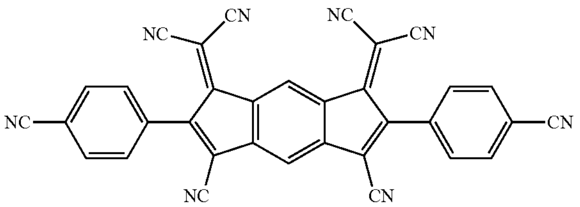
B34
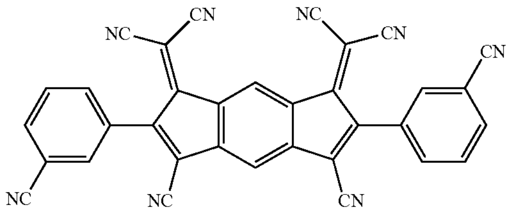
B35
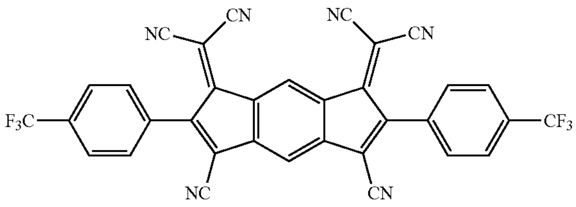

-continued
B36
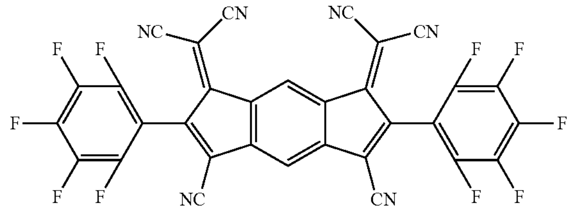
B37
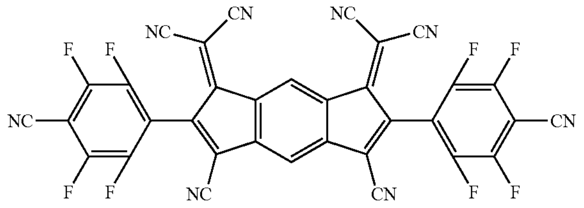
B38
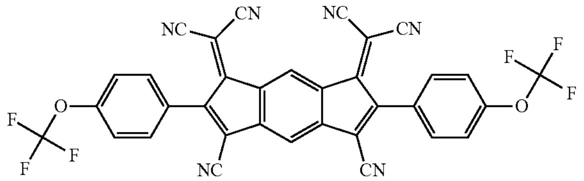
B39
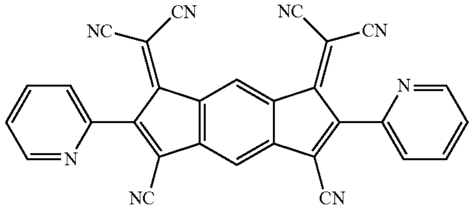
B40
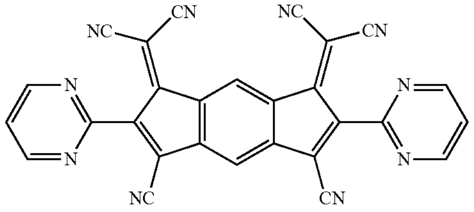
B41
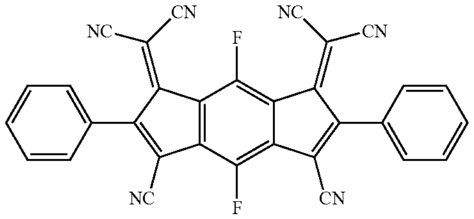
B42
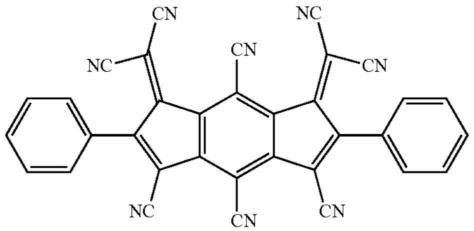
-continued
B43
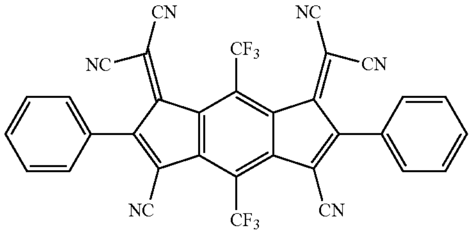
B44
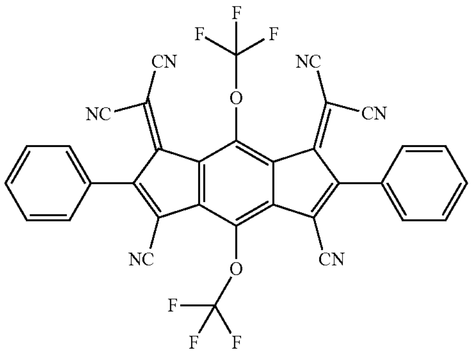
B45
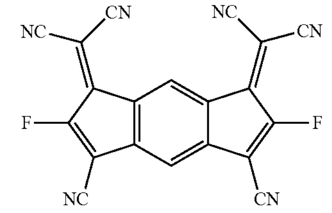
B46
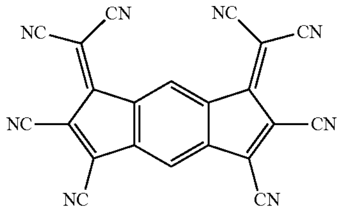
B47
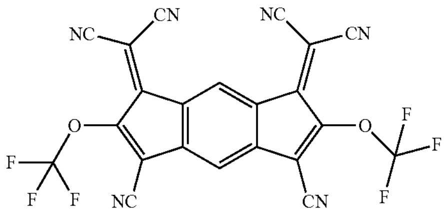
B48
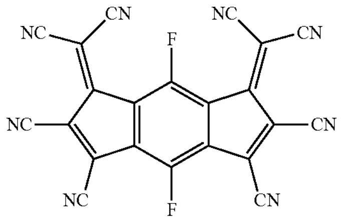

-continued

B49

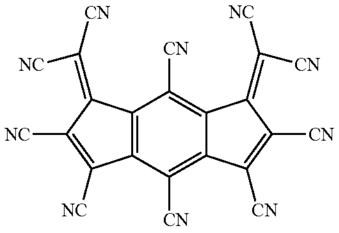

B50

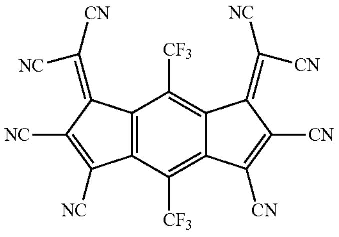

B51

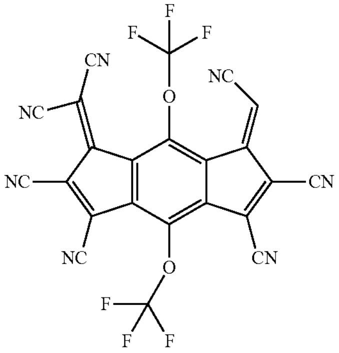

B52

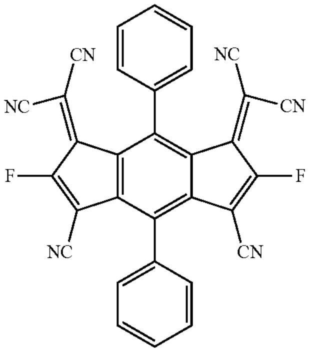

B53

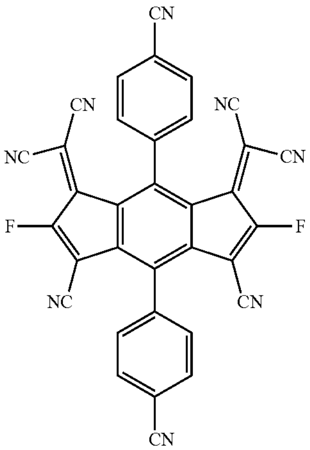

-continued

B54

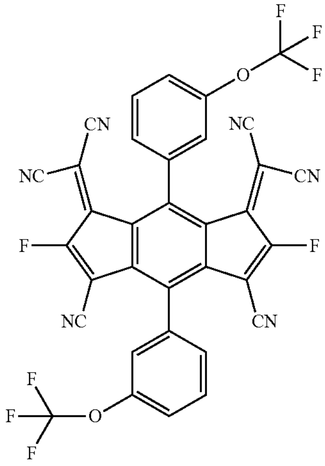

B55

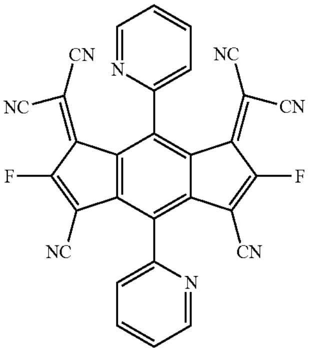

B56

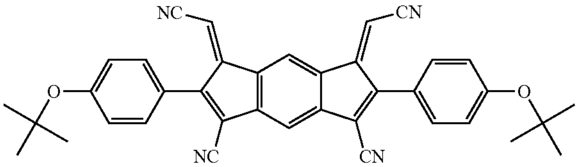

The above-described compound of this disclosure comprises indene as a core, which provides process stability against heat or deposition, thus simplifying the composition and deposition of the compound. Moreover, the compound of this disclosure improves the hole injection properties by comprising an electron-attracting substituent attached to the core and making the LUMO energy level of the compound similar to or lower than the HOMO energy level of the host of the hole injection layer, the host of the P-type charge generation layer, or the hole transport layer.

Accordingly, the hole injection layer is formed of the compound of this disclosure to ensure the process stability of the compound, simplifying the fabrication of the organic light emitting display device. Moreover, the compound of this disclosure can reduce the device's operating voltage and improve its efficiency and lifetime since the improvement in hole injection properties helps to facilitate the transfer of holes from the anode to the light emitting layer.

The hole injection layer 120 may be formed of a compound of this disclosure, or may comprise the compound as a dopant. The hole injection layer 120 may form solely of a compound of this disclosure. Also, if the hole injection layer 120 comprises a compound of this disclosure as a dopant, the hole injection layer 120 may comprise one or more hosts among CuPc (copper phthalocyanine), PEDOT (poly(3,4)-ethylenedioxythiophene), PANI (polyaniline), DNTPD (N1',N1''-(biphenyl-4,4'-diyl)bis($N^1$-phenyl-$N^4$,$N^4$-di-m-tolyl-benzene-1,4-diamine), and NPD (N,N'-bis(naphthalene-1-yl)-N,N'-bis(phenyl)-2,2'-dimethylbenzidine) and a dopant comprising the compound of this disclosure.

The hole injection layer 120 may have a 1 to 150 nm thickness. If the hole injection layer 120 has a 1 nm thickness or greater, the hole injection properties may be improved. If the hole injection layer 120 has a 150 nm thickness or less, an increase in the thickness of the hole injection layer 120 may be prevented and a rise in operating voltage may be therefore prevented.

The hole transport layer 130 may function to facilitate hole transport, and may be formed of, but is not limited to, one or more among NPD (N,N'-bis(naphthalene-1-yl)-N,N'-bis(phenyl)-2,2'-dimethylbenzidine), TPD (N,N'-bis-(3-methylphenyl)-N,N'-bis(phenyl)-benzidine), spiro-TAD (2,2'7,7'-tetrakis(N,N-diphenylamino)-9,9'-spirofluorene), NPB (N,N'-bis(naphthalene-1-yl-N,N'-bis(phenyl)-benzidine), and MTDATA (4,4',4''-Tris(N-3-methylphenyl-N-phenylamino)-triphenylamine). The hole transport layer 130 may have a 1 to 150 nm thickness. If the hole transport layer 130 has a 1 nm thickness or greater, the hole transport properties may be improved, or if the hole transport layer 130 has a 150 nm thickness or less, an increase in the thickness of the hole transport layer 130 may be prevented, and a rise in operating voltage may be therefore prevented. Moreover, an electron blocking layer may be further formed over the hole transport layer 130.

The light emitting layer 140 may emit light of red (R), green (G), or blue (B), and may be formed of a fluorescent material or phosphorescent material.

If the light emitting layer 140 is a red light emitting layer, it may be formed of, but is not limited to, a fluorescent material comprising PBD:$Eu(DBM)_3$(Phen) or perylene. If the light emitting layer 140 is a green light emitting layer, it may be formed of, but is not limited to, a fluorescent material comprising $Alq_3$(tris(8-hydroxyquinolinato)aluminum). If the light emitting layer 140 is a blue light emitting layer, it may be formed of, but is not limited to, a fluorescent material comprising one among spiro-BDAVBi (2,7-bis[4-(diphenylamino)styryl]-9,9-spirofluorene), spiro-CBP (2,2',7,7'-tetrakis(carbozol-9-yl)-9,9-spirofluorene), distyrylbenzene (DSB), distyrylarylene (DSA), a PFO (polyfluorene) polymer, and a PPV (polyphenylenevinylene) polymer.

The electron transport layer 150 may function to facilitate the transport of electrons, and may be formed of, but is not limited to, one or more among $Alq_3$ (tris(8-hydroxyquinolinato)aluminum), PBD (2-4-biphenyl)-5-(4-tert-butylphenyl)-1,3,4-oxadiazole), TAZ (3-(4-biphenyl)-4-pheynyl-5-tert-butylphenyl-1,2,4-triazole), DPT (2-biphenyl-4-yl-4,6-bis-(4'-pyridin-2-yl-biphenyl-4-yl)-[1,3,5]triazine), and BAlq (Bis(2-methyl-8-quinolinolato)-4-(phenylphenolato) aluminum). The electron transport layer 150 may have a 1 to 150 nm thickness. If the electron transport layer 150 has a 1 nm thickness or greater, a degradation of the electron transport properties may be prevented. If the electron transport layer 150 has a 150 nm thickness or less, an increase in the thickness of the electron transport layer 150 may be prevented, and a rise in operating voltage may be therefore prevented.

The electron injection layer 210 functions to facilitate electron injection, and may be formed of, but is not limited to, one among $Alq_3$ (tris(8-hydroxyquinolinato)aluminum), PBD (2-4-biphenyl)-5-(4-tert-butylphenyl)-1,3,4-oxadiazole), TAZ (3-(4-biphenyl)-4-pheynyl-5-tert-butylphenyl-1,2,4-triazole), and BAlq (Bis(2-methyl-8-quinolinolato)-4-(phenylphenolato)aluminum). On the other hand, the electron injection layer 210 may be formed of a metal compound, and the metal compound may be, for example, but is not limited to, one or more among LiQ, LiF, NaF, KF, RbF, CsF, FrF, $BeF_2$, $MgF_2$, $CaF_2$, $SrF_2$, $BaF_2$, and $RaF_2$. The electron injection layer 210 may have a 1 to 50 nm thickness. If the electron injection layer 210 has a 1 nm thickness or greater, a degradation of the electron injection properties may be prevented. If the electron injection layer 210 has a 50 nm thickness or less, an increase in the thickness of the electron injection layer 210 may be prevented, and a rise in operating voltage may be therefore prevented. The electron injection layer 210 may not be included in the elements of the organic light emitting display device, depending on the structure or characteristics of the device.

The cathode 220 is an electron injection electrode, and may be formed of magnesium (Mg), calcium (Ca), aluminum (Al), silver (Ag), or an alloy thereof, having a low work function. If the organic light emitting display device is a top-emission type or a dual-emission type, the cathode 220 may be formed thin enough to pass light therethrough. If the organic light emitting display device is a bottom-emission type, the cathode 220 may be formed thick enough to reflect light.

As above, a compound of this disclosure comprises indene as a core, which provides process stability against heat or deposition, thus simplifying the composition and deposition of the compound. Moreover, the compound of this disclosure improves the hole injection properties by comprising an electron-attracting substituent attached to the core and making the LUMO energy level of the compound similar to or lower than the HOMO energy level of the host of the hole injection layer, the host of the P-type charge generation layer, or the hole transport layer.

Accordingly, the hole injection layer is formed of the compound of this disclosure to ensure the process stability of the compound, which simplifies the fabrication of the organic light emitting display device. Moreover, the compound of this disclosure can reduce the device's operating voltage and improve its efficiency and lifetime since the improvement in hole injection properties helps to facilitate the transfer of holes from the anode to the light emitting layer.

Figure 2:
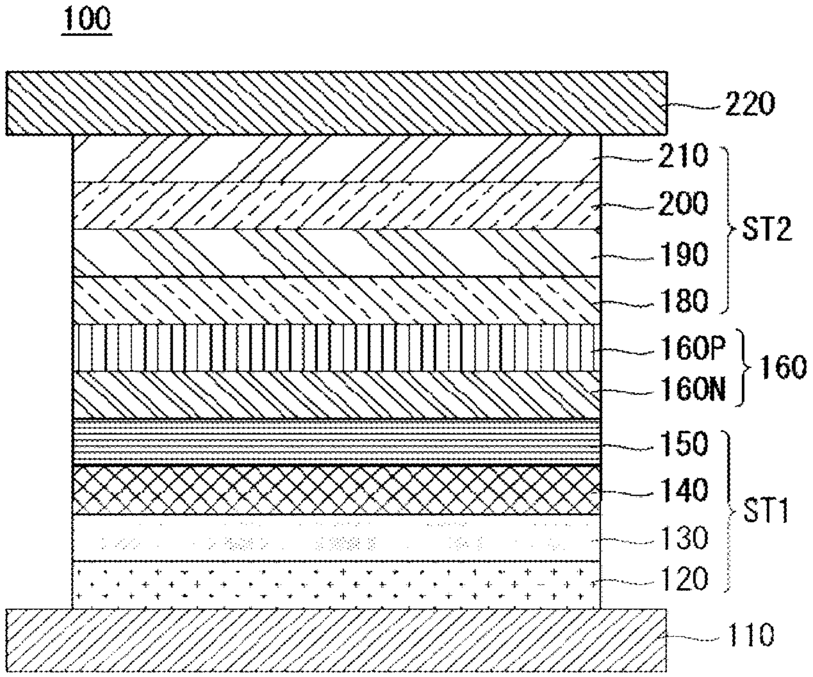
FIG. 2 is a cross-sectional view showing an organic light emitting display device according to a second exemplary embodiment of the present disclosure.

FIG. 2 is a view showing an organic light emitting display device according to a second exemplary embodiment of the present disclosure. The same elements as the first exemplary embodiment are denoted by the same reference numerals, so descriptions of these elements will be omitted or may be brief below.

Referring to FIG. 2, an organic light emitting display device 100 of the present disclosure comprises light emitting parts ST1 and ST2 between an anode 110 and a cathode 220, and a charge generation layer 160 between the light emitting parts ST1 and ST2.

The first light emitting part ST1 comprises a first light emitting layer 140. The first light emitting layer 140 may emit light of red (R), green (G), or blue (B), and may be formed of a fluorescent or phosphorescent material. In this exemplary embodiment, the first light emitting layer 140 may be a blue light emitting layer. The blue light emitting layer comprises one among a blue light emitting layer, a dark blue light emitting layer, and a sky blue light emitting layer. Alternatively, the first light emitting layer 140 may form of a blue light emitting layer and a red light emitting layer, a blue light emitting layer and a yellow-green light emitting layer, or a blue light emitting layer and a green light emitting layer. If the first light emitting layer 140 is a blue light emitting layer, it may emit light over a wavelength range of 440 to 480 nm. If the first light emitting layer 140 forms of a blue light emitting layer and a red light emitting layer, it may emit light over a wavelength range of 440 to 650 nm. If the first light emitting layer 140 forms of a blue light emitting layer and a yellow-green light emitting layer, it may emit light over a wavelength range of 440 to 590 nm. If the first light emitting layer 140 forms of a blue light emitting layer and a green light emitting layer, it may emit light over a wavelength range of 440 to 580 nm.

The first light emitting part ST1 comprises a hole injection layer 120 and a first hole transport layer 130 that are between the anode 110 and the first light emitting layer 140, and a first electron transport layer 150 on the first light emitting layer 140. Accordingly, the first light emitting part ST1 comprising the hole injection layer 120, first hole transport layer 130, first light emitting layer 140, and first electron transport layer 150 is formed on the anode 110. The first hole transport layer 130 may be formed of, but is not limited to, the same material as the hole transport layer 130 explained with reference to FIG. 1.

A charge generation layer (CGL) 160 is between the first light emitting part ST1 and the second light emitting part ST2. The first light emitting part ST1 and the second light emitting part ST2 are connected by the charge generation layer 160. The charge generation layer 160 may be a PN-junction charge generation layer formed by joining an N-type charge generation layer 160N and a P-type charge generation layer 160P. The PN junction charge generation layer 160 generates a charge, or injects the charge (i.e., electrons and holes), separately into the light emitting layer. That is, the N-type charge generation layer 160N transfers electrons to the first electron transport layer 150, and the first electron transport layer 150 supplies the electrons to the first light emitting layer 140 adjacent to the anode, and the P-type charge generation layer 160P transfers holes to the second hole transport layer 180, and the second hole transport layer 180 supplies the holes to the second light emitting layer 190 of the second light emitting part ST2. As such, the luminous efficiency of the first and second light emitting layers 140 and 190 may be further increased, and the operating voltage may be reduced.

The N-type charge generation layer 160N may be formed of a metal or an N-doped organic material. The metal may be one among Li, Na, K, Rb, Cs, Mg, Ca, Sr, Ba, La, Ce, Sm, Eu, Tb, Dy, and Yb. An N-type dopant and host for the N-doped organic material may be commonly-used materials. For example, the N-type dopant may be an alkali metal, an alkali metal compound, an alkali earth metal, or an alkali earth metal compound. Specifically, the N-type dopant may be one among Li, Cs, K, Rb, Mg, Na, Ca, Sr, Eu, and Yb. The host material may be an organic matter that has a nitrogen atom-containing hetero ring, with 20 to 60 carbon atoms, for example, one material among $Alq_3$ (tris(8-hydroxyquinolinato)aluminum), triazine, a hydroxyquinoline derivative, a benzazole derivative, and a silole derivative.

The P-type charge generation layer 160P may be formed of the same material as the hole injection layer 120 of the above-described first exemplary embodiment. A compound of this disclosure comprises indene as a core, which provides process stability against heat or deposition, thus simplifying the composition and deposition of the compound. Moreover, the compound of this disclosure improves the hole injection properties by comprising an electron-attracting substituent attached to the core and making the LUMO energy level of the compound similar to or lower than the HOMO energy level of the hole transport layer.

Accordingly, the P-type charge generation layer is formed of the compound of this disclosure to ensure the process stability of the compound, which simplifies the fabrication of the organic light emitting display device. Moreover, the compound of this disclosure can reduce the device's operating voltage and improve its efficiency and lifetime since the improvement in hole injection properties helps to facilitate the transfer of holes from the anode to the light emitting layer.

The second light emitting part ST2 comprising a second hole transport layer 180, the second light emitting layer 190, a second electron transport layer 200, and an electron injection layer 210 is on the charge generation layer 160.

The second light emitting layer 190 may emit light of red (R), green (G), blue (B), or yellow-green (YG), and may be formed of a fluorescent or phosphorescent material. In this exemplary embodiment, the second light emitting layer 190 may be a light emitting layer that emits yellow-green light. The second light emitting layer 190 may have a single layer structure of a yellow-green light emitting layer or a green light emitting layer, or a multilayer structure formed of a yellow-green light emitting layer and a green light emitting layer. The second light emitting layer 190 comprises a yellow-green light emitting layer, a green light emitting layer, or a multilayer structure formed of a yellow-green light emitting layer and a green light emitting layer, a yellow light emitting layer and a red light emitting layer, a green light emitting layer and a red light emitting layer, or a yellow-green light emitting layer and a red light emitting layer. If the second light emitting layer 190 forms of a yellow-green light emitting layer, a green light emitting layer, or a yellow-green light emitting layer and a green light emitting layer, it may emit light over a wavelength range of 510 to 590 nm. If the second light emitting layer 190 is formed of a yellow light emitting layer and a red light emitting layer, a green light emitting layer and a red light emitting layer, or a yellow-green light emitting layer and a red light emitting layer, it may emit light over a wavelength range of 510 to 650 nm.

This exemplary embodiment will be described by taking as an example a single layer structure of a second light emitting layer 190 that emits yellow-green light. The second light emitting layer 190 may comprise, but is not limited to, at least one host of CBP (4,4'-bis(carbazol-9-yl)biphenyl) and BAlq (Bis(2-methyl-8-quinolinolato)-4-(phenylphenolato)aluminum) and a phosphorescent yellow-green dopant that emits yellow-green light.

The second light emitting part ST2 comprises the second hole transport layer 180 between the charge generation layer 160 and the second light emitting layer 190, and comprises the second electron transport layer 200 and electron injection layer 210 on the second light emitting layer 190. The second hole transport layer 180 may be formed of, but is not limited to, the same material as the hole transport layer 130 explained with reference to FIG. 1.

Accordingly, the second light emitting part ST2 comprising the second hole transport layer 180, second light emitting layer 190, second electron transport layer 200, and electron injection layer 210 is formed on the charge generation layer 160. The cathode 220 is provided on the second light emitting part ST2 to constitute the organic light emitting display device according to the second exemplary embodiment of the present disclosure.

The above-described second exemplary embodiment of the present disclosure has disclosed that the P-type charge generation layer 160P comprise a compound of this disclosure. As in the above-described first exemplary embodiment, the compound of this disclosure may be also used as the hole injection layer 120. The compound of this disclosure may be included in at least one among the hole injection layer 120 and the P-type charge generation layer 160P.

As above, a compound of this disclosure comprises indene as a core, which provides process stability against heat or deposition, thus simplifying the composition and deposition of the compound. Moreover, the compound of this disclosure improves the hole injection properties by comprising an electron-attracting substituent attached to the core and making the LUMO energy level of the compound similar to or lower than the HOMO energy level of host of the hole injection layer, the host of the P-type charge generation layer, or the hole transport layer.

Accordingly, at least one among the hole injection layer and the P-type charge generation layer is formed of the compound of this disclosure to ensure the process stability of the compound, which simplifies the fabrication of the organic light emitting display device. Moreover, the compound of this disclosure can reduce the device's operating voltage and improve its efficiency and lifetime since the improvement in hole injection properties helps to facilitate the transfer of holes from the anode to the light emitting layer.

Figure 3:
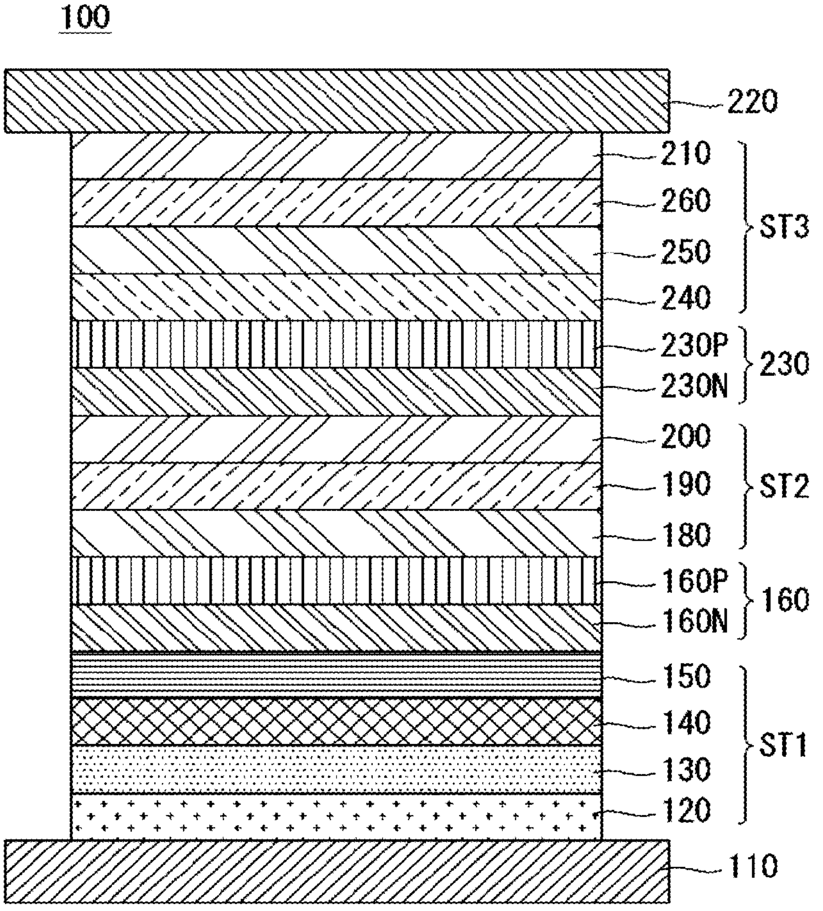
FIG. 3 is a cross-sectional view showing an organic light emitting display device according to a third exemplary embodiment of the present disclosure.

FIG. 3 is a view showing an organic light emitting display device according to a third exemplary embodiment of the present disclosure. The same elements as the first and second exemplary embodiments are denoted by the same reference numerals, so descriptions of these elements will be omitted or may be brief below.

Referring to FIG. 3, an organic light emitting display device 100 of the present disclosure comprises a plurality of light emitting parts ST1, ST2, and ST3 between an anode 110 and a cathode 220, and a first charge generation layer 160 and a second charge generation layer 230 that are between the light emitting parts ST1, ST2, and ST3. Although this exemplary embodiment has been illustrated and described with an example where three light emitting parts are between the anode 110 and the cathode 220, the present disclosure is not limited to this example and four or more light emitting parts may be between the anode 110 and the cathode 220.

Among the light emitting parts, the first light emitting part ST1 comprises a first light emitting layer 140. The first light emitting layer 140 may emit light one among red, green, and blue. For example, it may be a blue light emitting layer in this exemplary embodiment. The blue light emitting layer comprises one among a blue light emitting layer, a dark blue light emitting layer, and a sky blue light emitting layer. Alternatively, the first light emitting layer 140 may form of a blue light emitting layer and a red light emitting layer, a blue light emitting layer and a yellow-green light emitting layer, or a blue light emitting layer and a green light emitting layer. If the first light emitting layer 140 is a blue light emitting layer, it may emit light over a wavelength range of 440 to 480 nm. If the first light emitting layer 140 forms of a blue light emitting layer and a red light emitting layer, it may emit light over a wavelength range of 440 to 650 nm. If the first light emitting layer 140 forms of a blue light emitting layer and a yellow-green light emitting layer, it may emit light over a wavelength range of 440 to 590 nm. If the first light emitting layer 140 forms of a blue light emitting layer and a green light emitting layer, it may emit light over a wavelength range of 440 to 580 nm.

The first light emitting part ST1 comprises a hole injection layer 120 and a first hole transport layer 130 that are between the anode 110 and the first light emitting layer 140, and a first electron transport layer 150 on the first light emitting layer 140. Accordingly, the first light emitting part ST1 comprising the hole injection layer 120, the first hole transport layer 130, the first light emitting layer 140, and the first electron transport layer 150 is formed on the anode 110.

The second light emitting part ST2 comprising a second light emitting layer 190 is on the first light emitting part ST1. The second light emitting layer 190 may emit light of one among red, green, blue, and yellow-green. For example, it may be a yellow-green light emitting layer in this exemplary embodiment. The second light emitting layer 190 comprises a yellow-green light emitting layer, a green light emitting layer, or a multilayer structure formed of a yellow-green light emitting layer and a green light emitting layer, a yellow light emitting layer and a red light emitting layer, a green light emitting layer and a red light emitting layer, or a yellow-green light emitting layer and a red light emitting layer. If the second light emitting layer 190 forms of a yellow-green light emitting layer, a green light emitting layer, or a yellow-green light emitting layer and a green light emitting layer, it may emit light over a wavelength range of 510 to 590 nm. If the second light emitting layer 190 forms of a yellow light emitting layer and a red light emitting layer, a green light emitting layer and a red light emitting layer, or a yellow-green light emitting layer and a red light emitting layer, it may emit light over a wavelength range of 510 to 650 nm.

The second light emitting part ST2 further comprises a second hole transport layer 180 on the first light emitting part ST1, and comprises a second electron transport layer 200 on the second light emitting layer 190. Accordingly, the second light emitting part ST2 comprising the second hole transport layer 180, the second light emitting layer 190, and the second electron transport layer 200 is formed on the first light emitting part ST1.

A first charge generation layer 160 is between the first light emitting part ST1 and the second light emitting part ST2. The first charge generation layer 160 is a PN-junction charge generation layer formed by joining an N-type charge generation layer 160N and a P-type charge generation layer 160P. The first charge generation layer 160 generates a charge, or injects the charge, i.e., electrons and holes, separately into the first and second light emitting layers 140 and 190.

The third light emitting part ST3 comprising a third light emitting layer 250 is on the second light emitting part ST2. The third light emitting layer 250 may emit light one among red, green, and blue, and be formed of a fluorescent material. For example, it may be a blue light emitting layer in this exemplary embodiment. The blue light emitting layer comprises one among a blue light emitting layer, a dark blue light emitting layer, and a sky blue light emitting layer. Alternatively, the third light emitting layer 250 may form of a blue light emitting layer and a red light emitting layer, a blue light emitting layer and a yellow-green light emitting layer, or a blue light emitting layer and a green light emitting layer. If the third light emitting layer 250 is a blue light emitting layer, it may emit light over a wavelength range of 440 to 480 nm. If the third light emitting layer 250 forms of a blue light emitting layer and a red light emitting layer, it may emit light over a wavelength range of 440 to 650 nm. If the third light emitting layer 250 forms of a blue light emitting layer and a yellow-green light emitting layer, it may emit light over a wavelength range of 440 to 590 nm. If the third light emitting layer 250 forms of a blue light emitting layer and a green light emitting layer, it may emit light over a wavelength range of 440 to 580 nm.

The third light emitting part ST3 further comprises a third hole transport layer 240 on the second light emitting part ST2, and a third electron transport layer 260 and an electron injection layer 210 that are on the third light emitting layer 250. Accordingly, the third light emitting part ST3 comprising the third hole transport layer 240, third light emitting layer 250, third electron transport layer 260, and electron injection layer 210 is formed on the second light emitting part ST2. The electron injection layer 210 may not be included in the elements of the third light emitting part ST3, depending on the structure or characteristics of the device.

The second charge generation layer 230 is between the second light emitting part ST2 and the third light emitting part ST3. The second charge generation layer 230 is a PN junction charge generation layer formed by joining the N-type charge generation layer 230N and the P-type charge generation layer 230P. The second charge generation layer 230 generates a charge, or injects the charge (i.e., electrons and holes), separately into the second and third light emitting layers 190 and 250. The cathode 220 is provided on the third light emitting part ST3 to constitute the organic light emitting display device according to the third exemplary embodiment of the present disclosure.

At least one among the hole injection layer 120, the P-type charge generation layer 160P of the first charge generation layer 160, and the P-type charge generation layer 260P of the second charge generation layer 260 is formed of a compound of this disclosure, as in the case of the foregoing exemplary embodiments. A compound of this disclosure comprises indene as a core, which provides process stability against heat or deposition, thus simplifying the composition and deposition of the compound. Moreover, the compound of this disclosure improves the hole injection properties by comprising an electron-attracting substituent attached to the core and making the LUMO energy level of the compound similar to or lower than the HOMO energy level of host of the hole injection layer, the host of the P-type charge generation layer, or the hole transport layer.

Accordingly, at least one among the hole injection layer and the P-type charge generation layer is formed of the compound of this disclosure to ensure the process stability of the compound, which simplifies the fabrication of the organic light emitting display device. Moreover, the compound of this disclosure can reduce the device's operating voltage and improve its efficiency and lifetime since the improvement in hole injection properties helps to facilitate the transfer of holes from the anode to the light emitting layer.

Organic light emitting displays using the organic light emitting display device according to the first to third exemplary embodiments of the present disclosure may include top emission displays, bottom emission displays, dual emission displays, and vehicle lighting. The vehicle lighting may include, but are not necessarily limited to, headlights, high beams, taillights, brake lights, and back-up lights. Moreover, organic light emitting displays using the organic light emitting display devices according to the first to third exemplary embodiments of the present disclosure may be applied to mobile devices, tablet PCs, monitors, smartwatches, laptop computers, vehicle displays, etc. Besides, these organic light emitting displays may be applied to vehicle displays, wearable displays, foldable displays, rollable displays, etc.

Also, organic light emitting displays using the organic light emitting display device according to the second exemplary embodiment of the present disclosure may be applied to displays in which the first and second light emitting layers emit light of the same color.

Also, organic light emitting displays using the organic light emitting display device according to the third exemplary embodiment of the present disclosure may be applied to displays in which at least two of the first, second, and third light emitting layers emit light of the same color.

Figure 4:
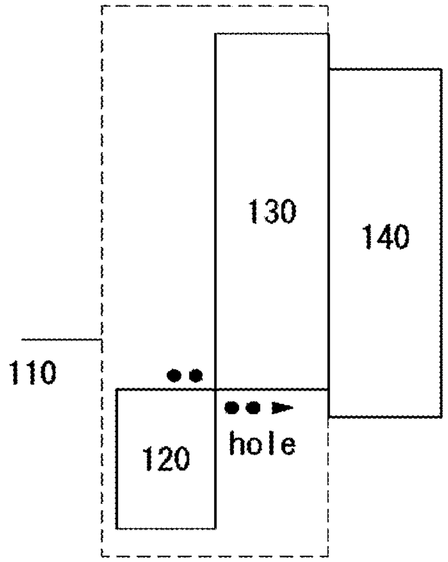
FIGS. 4 and 5 are energy band diagrams of an organic light emitting display device according to one or more embodiments of the present disclosure.
Figure 5:
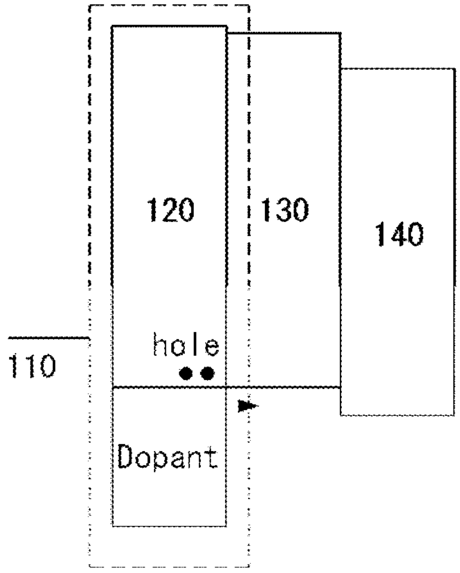

FIGS. 4 and 5 are energy band diagrams of an organic light emitting display device of the present disclosure. Referring to FIG. 4, the anode 110, the hole injection layer 120, the hole transport layer 130, and the light emitting layer 140 are illustrated. The hole injection layer 120 may be formed of a single material comprising a compound of this disclosure. The hole transport layer 130 may be formed of, for example, NPD. Since the LUMO energy level of the compound in the hole injection layer 120 is similar to or lower than the HOMO energy level of the hole transport layer 130, electrons are accepted from the HOMO energy level of the hole transport layer 130 to the LUMO energy level of the compound, thereby forming a hole transport path. Accordingly, holes can be smoothly injected from the hole injection layer 120 into the hole transport layer 130 through the hole transport path (indicated by the arrows) between the hole injection layer 120 and the hole transport layer 130.

Referring to FIG. 5, the hole injection layer 120 may comprise a dopant introduced into a host. Accordingly, a compound of this disclosure acts as the dopant. Since the LUMO energy level of the compound used as a dopant for the hole injection layer 120 is similar to or lower than the HOMO energy level of the host, electrons are accepted from the HOMO energy level of the host to the LUMO energy level of the compound of this disclosure, thereby forming a hole transport path (indicated by the arrow). Accordingly, holes can be smoothly injected from the hole injection layer 120 into the hole transport layer 130 through the hole transport path between the HOMO energy level of the host and the LUMO energy level of the compound of this disclosure, within the hole injection layer 120. As a result, the use of the compound of this disclosure as a dopant for the hole injection layer 120 facilitates the transfer of holes from the hole injection layer 120 into the hole transport layer 130, leading to a reduction in operating voltage.

Although FIGS. 4 and 5 are explained with respect to the hole injection layer by way of example, the same may apply when the hole injection layer 120 is replaced with the P-type charge generation layer 160P of FIG. 2 and the hole transport layer 130 is replaced with the second hole transport layer 170 of FIG. 2. Accordingly, referring to FIG. 4, if the hole injection layer 120 is replaced with the P-type charge generation layer 160P of FIG. 2, the P-type charge generation layer 160P may be formed of a single material comprising a compound of this disclosure. Also, referring to FIG. 5, the P-type charge generation layer 160P may comprise a compound of this disclosure as a dopant.

Moreover, the same applies when the hole injection layer 120 is replaced with the P-type charge generation layer 160P of FIG. 3 and the hole transport layer 130 is replaced with the second hole transport layer 170 of FIG. 3. Accordingly, referring to FIG. 4, if the hole injection layer 120 is replaced with the P-type charge generation layer 160P of FIG. 3, the P-type charge generation layer 160P may be formed of a single material comprising a compound of this disclosure. Also, referring to FIG. 5, the P-type charge generation layer 160P may comprise a compound of this disclosure as a dopant.

Furthermore, the same applies when the hole injection layer 120 is replaced with the P-type charge generation layer 230P of FIG. 3 and the hole transport layer 130 is replaced with the third hole transport layer 240 of FIG. 3. Accordingly, referring to FIG. 4, if the hole injection layer 120 is replaced with the P-type charge generation layer 230P of FIG. 3, the P-type charge generation layer 230P may be formed of a single material comprising a compound of this disclosure. Also, referring to FIG. 5, the P-type charge generation layer 230P may comprise a compound of this disclosure as a dopant.

Hereinafter, synthesis examples of compounds of the present disclosure will be described in detail. However, the following examples are only for illustration, and the present disclosure is not limited thereto.

Synthesis of Compound B31

1) Preparation of 1,5-bis(chloromethyl)-2,4-bis(2-phenylethynyl)benzene

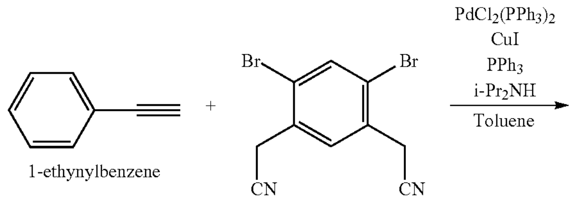

1-ethynylbenzene 1,5-dibromophenyl-2,4-dicarbonitrile

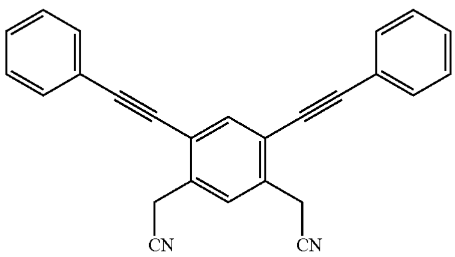

2-bromophenyl)acetonitrile (0.12 mol), bis(triphenylphosphine)palladium(II)chloride ($PdCl_2(PPh_3)_2$) (2 mmol), copper iodide (CuI) (2 mmol), triphenylphosphine ($PPh_3$) (4 mmol), and diisopropylamine (i-$Pr_2NH$) (0.1 mol) were put into a 250 ml two-necked flask under a nitrogen atmosphere and stirred for 5 min at room temperature, and then 1,5-dibromophenyl-2,4-dicarbonitrile (0.05 mol) was added to the mixture and stirred for 24 hours at 50° C. An organic layer was obtained by extraction with $H_2O$/ethyl acetate, dried over magnesium sulfate ($MgSO_4$), and then subjected to column chromatography to give 10.9 g of solid (yield: 61%).

2) Preparation of 3,5-dihydro-3,5-dioxo-2,6-diphenyl-s-indacene-1,7-dicarbonitrile

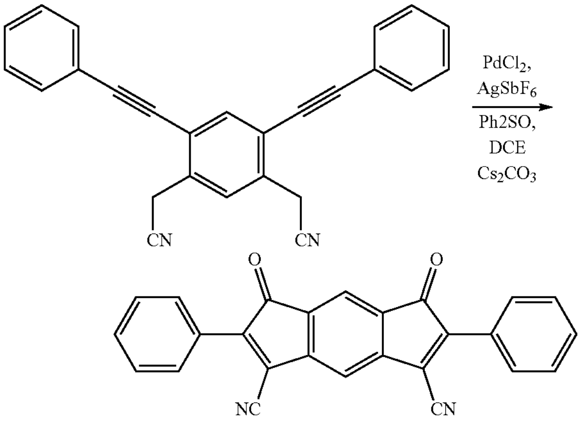

1,5-bis(chloromethyl)-2,4-bis(2-phenylethynyl)benzene (0.03 mol), palladium(II) chloride ($PdCl_2$) (6.1 mmol), silver hexafluoroantimonate ($AgSbF_6$) (9.1 mmol), and diphenylsulfoxide ($Ph_2SO$) (0.18 mol) were dissolved in a 250 ml two-necked flask with dichloroethylene (DCE) and stirred for 24 hours at 60° C., and then cesium carbonate ($Cs_2CO_3$) (0.074 mol) was added to the mixture and stirred for 12 hours. After the reaction, an extract was obtained by extraction with dichloromethane ($CH_2Cl_2$), which was dried up after the extraction, and then put into 35% hydrochloric acid (HCl) and stirred for 2 hours. An organic layer was obtained by extraction with a dichloromethane/ammonium chloride ($CH_2Cl_2$/aq.$NH_4Cl$) solution, dried over magnesium sulfate ($MgSO_4$), and then subjected to column chromatography to give 4.4 g of solid (yield: 38%).

3) Preparation of 3,5-bis(dicyanomethylene)-3,5-dihydro-2,6-diphenyl-s-indacene-1,7-dicarbonitrile

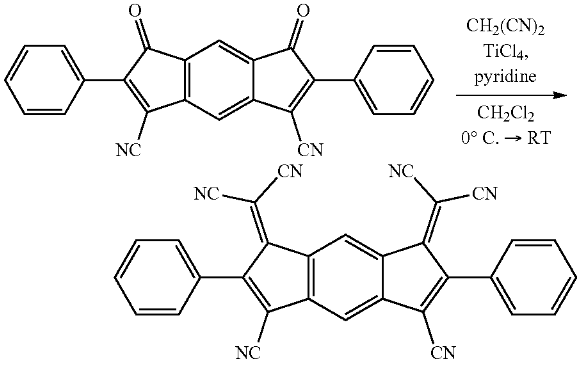

B31

3,5-dihydro-3,5-dioxo-2,6-diphenyl-s-indacene-1,7-dicarbonitrile (0.01 mol), malononitrile (0.062 mol), and dichloromethane ($CH_2Cl_2$) were put into a 100 ml two-necked flask and stirred for 30 min under an argon atmosphere. Titanium(IV) chloride ($TiCl_4$) (0.062 mol) was slowly added to the mixture, followed by the addition of pyridine (0.1 mol), and stirred at room temperature. An organic layer was obtained by extraction with a dichloromethane/ammonium chloride ($CH_2Cl_2$/aq.$NH_4Cl$) solution, dried over magnesium sulfate ($MgSO_4$), and then subjected to column chromatography to give 1.6 g of solid, i.e., Compound B31 (yield: 32%).

Synthesis of Intermediate

1) Preparation of 1,5-bis(chloromethyl)-2,4-bis(2-phenylethynyl)benzene

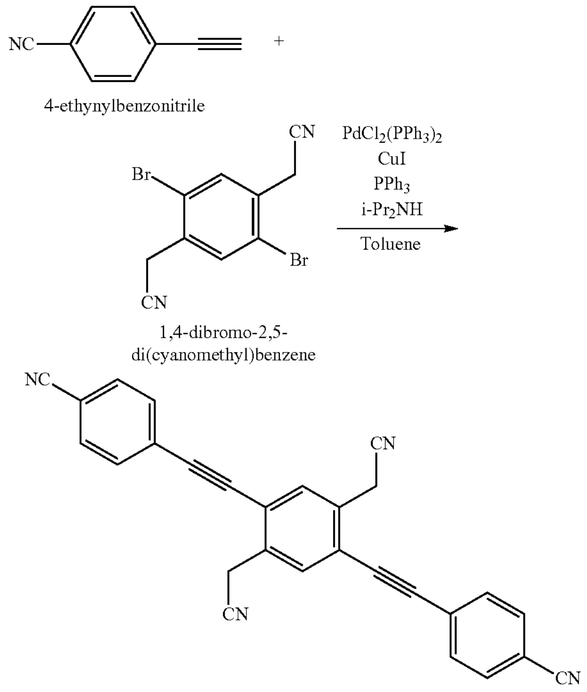

4-ethynylbenzonitrile 1,4-dibromo-2,5-di(cyanomethyl)benzene 4-ethynylbenzonitrile (0.12 mol), bis(triphenylphosphine) palladium(II)chloride ($PdCl_2(PPh_3)_2$) (2 mmol), copper iodide (CuI) (2 mmol), triphenylphosphine ($PPh_3$) (4 mmol), and diisopropylamine (i-$Pr_2NH$) (0.1 mol) were put into a 250 ml two-necked flask under a nitrogen atmosphere and stirred for 5 min at room temperature, and then 1,4-dibromo-2,5-di(cyanomethyl)benzene (0.05 mol) was added to the mixture and stirred for 24 hours at 50° C. An organic layer was obtained by extraction with $H_2O$/ethyl acetate, dried over magnesium sulfate ($MgSO_4$), and then subjected to column chromatography to give 13.8 g of solid (yield: 68%).

2) Preparation of 2,6-bis(4-cyanophenyl)-3,7-dihydro-3,7-dioxo-s-indacene-1,5-dicarbonitrile

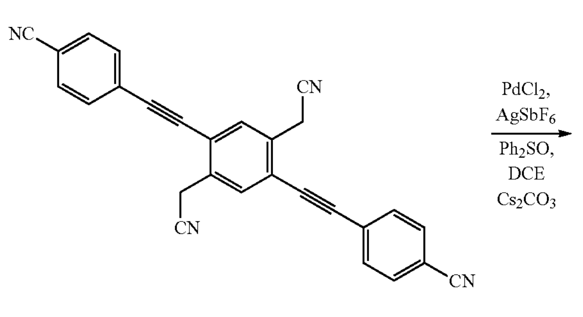

-continued

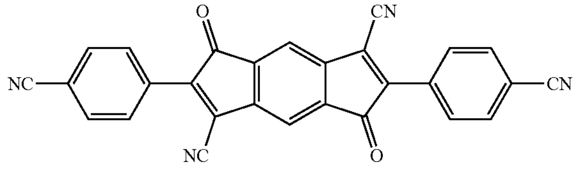

1,4-di(cyanomethyl)-2,5-bis(2-(4-cyanophenyl)ethynyl) benzene (0.034 mol), palladium(II)chloride ($PdCl_2$) (6.8 mmol), silver hexafluoroantimonate ($AgSbF_6$) (10.2 mmol), and diphenylsulfoxide ($Ph_2SO$) (0.2 mol) were dissolved in a 250 ml two-necked flask with dichloroethylene (DCE) and stirred for 24 hours at 60° C. After the reaction, an extract was obtained by extraction with dichloromethane ($CH_2Cl_2$), which was dried up after the extraction, and then put into 35% hydrochloric acid (HCl) and stirred for 2 hours. An organic layer was obtained by extraction with a dichloromethane/ammonium chloride ($CH_2Cl_2$/aq.$NH_4Cl$) solution, dried over magnesium sulfate ($MgSO_4$), and then subjected to column chromatography to give 5.9 g of solid, i.e., an intermediate, (yield: 48%).

Synthesis of Compound A33

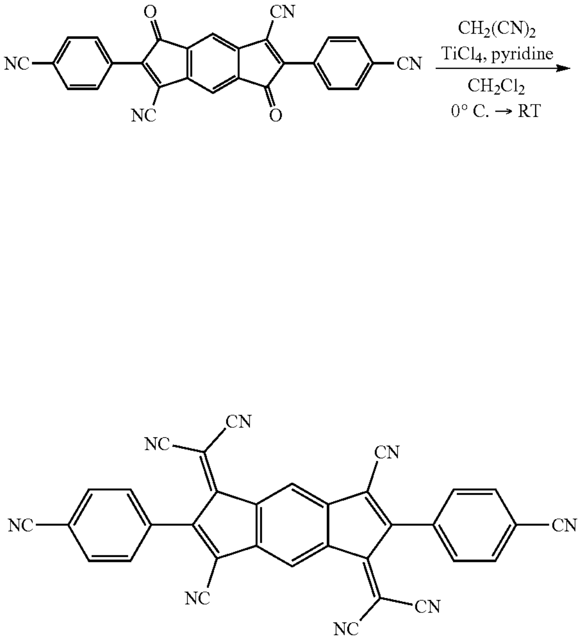

A33

2,6-bis(4-cyanophenyl)-3,7-dihydro-3,7-dioxo-s-indacene-1,5-dicarbonitrile (13.6 mmol), malononitrile (0.082 mol), and dichloromethane ($CH_2Cl_2$) were put into a 100 ml two-necked flask and stirred for 30 min under an argon atmosphere. Titanium(IV)chloride ($TiCl_4$) (0.082 mol) was slowly added to the mixture, followed by the addition of pyridine (0.1 mol), and stirred at room temperature. After the reaction, an organic layer was obtained by extraction with a dichloromethane/ammonium chloride ($CH_2Cl_2$/aq.$NH_4Cl$) solution, dried over magnesium sulfate ($MgSO_4$), and then subjected to column chromatography to give 2.5 g of solid, i.e., Compound A33 (yield: 35%).

Synthesis of Compound A62

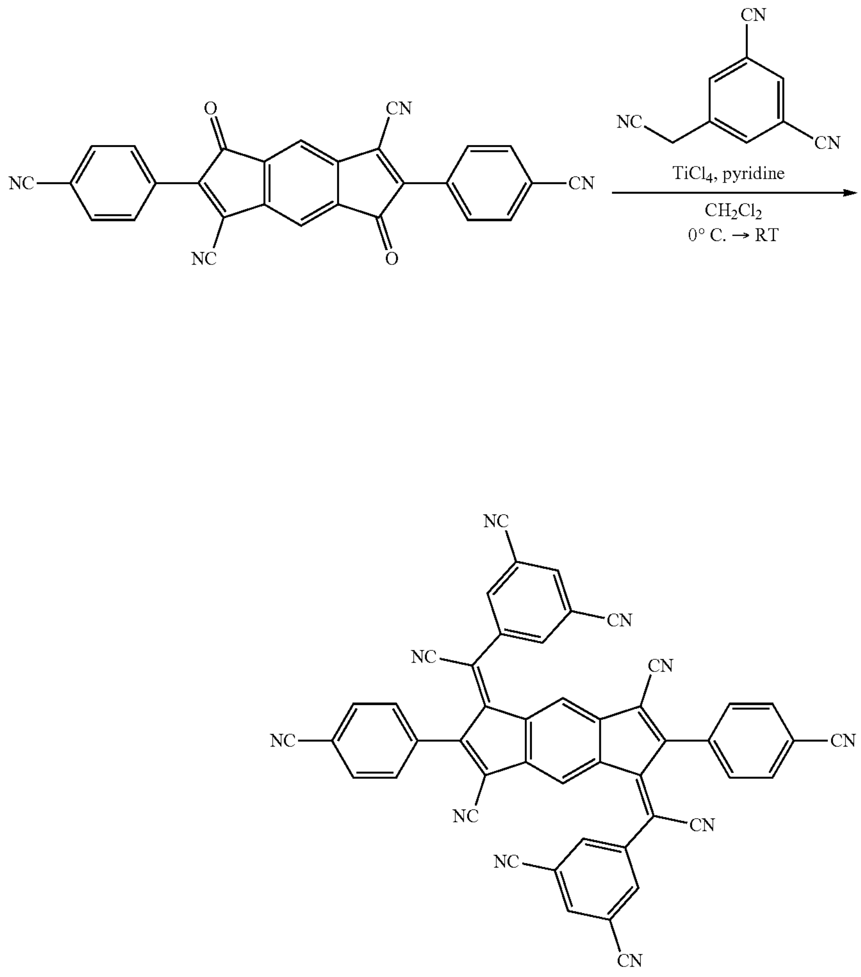

A62

2,6-bis(4-cyanophenyl)-3,7-dihydro-3,7-dioxo-s-indacene-1,5-dicarbonitrile (0.01 mol), 5-(cyanomethyl)benzene-1,3-dinitrile (0.06 mol), and chloromethane ($CH_2Cl_2$) were put into a 100 ml two-necked flask and stirred for 30 min under an argon atmosphere. Titanium(IV)chloride ($TiCl_4$) (0.06 mol) was slowly added to the mixture, followed by the addition of pyridine (0.1 mol), and stirred at room temperature. An organic layer was obtained by extraction with a dichloromethane/ammonium chloride ($CH_2Cl_2$/aq.$NH_4Cl$) solution, dried over magnesium sulfate ($MgSO_4$), and then subjected to column chromatography to give 2.3 g of solid, i.e., Compound A62 (yield: 31%).

Synthesis of Compound A63

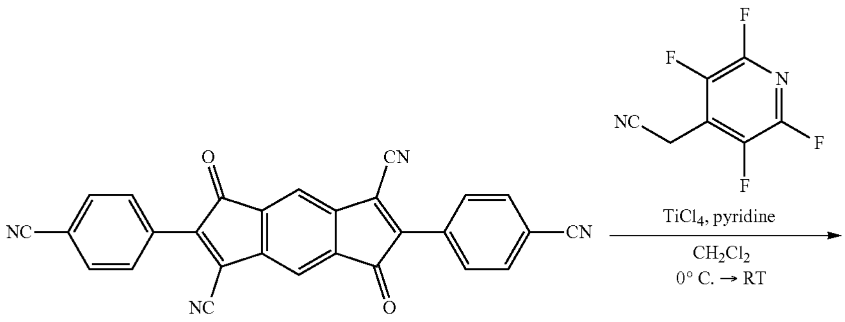

-continued

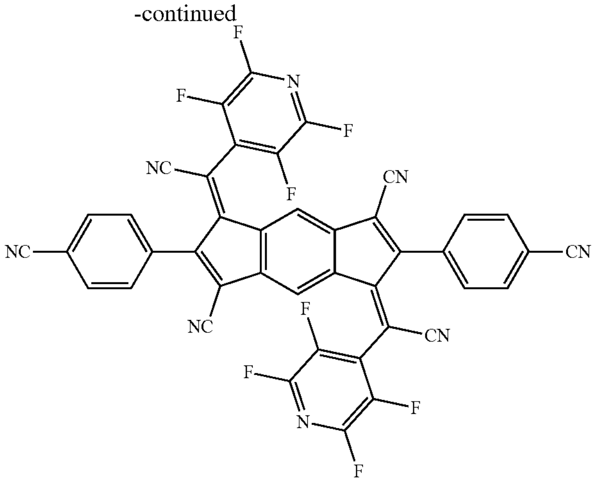

A63

2,6-bis(4-cyanophenyl)-3,7-dihydro-3,7-dioxo-s-indacene-1,5-dicarbonitrile (0.01 mol), 2-(perfluoropyridin-4-yl)acetonitrile (0.06 mol), and chloromethane ($CH_2Cl_2$) were put into a 100 ml two-necked flask and stirred for 30 min under an argon atmosphere. Titanium(IV)chloride ($TiCl_4$) (0.06 mol) was slowly added to the mixture, followed by the addition of pyridine (0.1 mol), and stirred at room temperature. After the reaction, an organic layer was obtained by extraction with a dichloromethane/ammonium chloride ($CH_2Cl_2$/aq.$NH_4Cl$) solution, dried over magnesium sulfate ($MgSO_4$), and then subjected to column chromatography to give 2.2 g of solid, i.e., Compound A63 (yield: 28%).

Hereinafter, examples for fabricating an organic light emitting display device of this disclosure will be disclosed. It should be noted that materials of the following hole injection layer and P-type charge generation layer do not limit the scope of this disclosure.

Test 1: Monolithic Device

Example 1

An organic light emitting display device was fabricated by forming, an anode, a hole injection layer, a hole transport layer, a blue light emitting layer, an electron transport layer, an electron injection layer, and a cathode on a substrate. Here, the hole injection layer was formed of Compound B31. After the deposition of these layers, the device was transferred from the deposition chamber into a dry box for encapsulation, and was subsequently encapsulated using an UV-curable epoxy resin and a moisture getter. The organic light emitting display device thus obtained was connected to an external power supply source, and upon application of direct current voltage, the results in Table 1 were obtained. The characteristics of all the fabricated devices were evaluated using a constant current source (KEITHLEY) and a photometer (PR650) at room temperature.

Example 2

It has the same elements as the above-described Example 1, and the hole injection layer was formed of NPD doped with 10% Compound B31.

Example 3

It has the same elements as the above-described Example 1, and the hole injection layer was formed of Compound A33.

Example 4

It has the same elements as the above-described Example 1, and the hole injection layer was formed of NPD doped with 10% Compound A33.

Example 5

It has the same elements as the above-described Example 1, and the hole injection layer was formed of Compound A62.

Example 6

It has the same elements as the above-described Example 1, and the hole injection layer was formed of NPD doped with 10% Compound A62.

Example 7

It has the same elements as the above-described Example 1, and the hole injection layer was formed of Compound A63.

Example 8

It has the same elements as the above-described Example 1, and the hole injection layer was formed of NPD doped with 10% Compound A63.

Comparative Example 1

It has the same elements as the above-described Example 1, and the hole injection layer was formed HAT-CN.

Comparative Example 2

It has the same elements as the above-described Example 2, and the hole injection layer was formed of NPD doped with 10% HAT-CN.

Comparative Example 3

It has the same elements as the above-described Example 2, but without the hole injection layer.

The operating voltage, efficiency, and external quantum efficiency of the devices fabricated according to Examples 1 to 8 of the present disclosure and Comparative Examples 1, 2, and 3 set forth above were measured and shown in the following Table 1. (The devices were driven at a drive current of 10 $mA/cm^2$ to measure the operating voltage, efficiency, and external quantum efficiency).

TABLE 1

| | Operating voltage (V) | Efficiency (Cd/A) | External quantum efficiency (%) |
|---|---|---|---|
| Example 1 | 4.2 | 4.0 | 4.5 |
| Example 2 | 4.1 | 4.4 | 4.9 |
| Example 3 | 3.9 | 4.5 | 5.2 |
| Example 4 | 3.8 | 4.5 | 5.2 |
| Example 5 | 4.0 | 4.3 | 5.0 |
| Example 6 | 4.0 | 4.4 | 5.1 |
| Example 7 | 4.1 | 4.2 | 5.0 |
| Example 8 | 4.0 | 4.4 | 5.0 |
| Comparative Example 1 | 4.2 | 4.1 | 4.7 |
| Comparative Example 2 | 6.0 | 3.0 | 3.9 |
| Comparative Example 3 | 6.8 | 1.8 | 2.3 |

Referring to Table 1, Example 1 in which the hole injection layer comprises Compound B31 of this disclosure and Comparative Example 1 in which HAT-CN is used as the hole injection layer showed similar levels of operating voltage, efficiency, and external quantum efficiency. Example 2 in which a hole injection layer of NPD is doped with Compound B31 of this disclosure showed a 1.9 V decrease in operating voltage, a 1.4 cd/A increase in efficiency, and 1.0% increase in external quantum efficiency, compared to Comparative Example 2 in which a hole injection layer of NPD is doped with HAT-CN. Example 1 of this disclosure showed a 2.6 V decrease in operating voltage, a 2.2 cd/A increase in efficiency, and 2.2% increase in external quantum efficiency, and Example 2 showed a 2.7 V decrease in operating voltage, a 2.6 cd/A increase in efficiency, and a 2.6% increase in external quantum efficiency, compared to Comparative Example 3 in which the hole injection layer was not formed.

Also, Example 3 in which the hole injection layer comprises Compound A33 of this disclosure showed a 0.3 V decrease in operating voltage, a 0.4 cd/A increase in efficiency, and a 0.5% increase in external quantum efficiency, compared to Comparative Example 1 in which HAT-CN is used as the hole injection layer. Example 4 in which a hole injection layer of NPD is doped with Compound A33 of this disclosure showed a 2.2 V decrease in operating voltage, a 1.5 cd/A increase in efficiency, and 1.3% increase in external quantum efficiency, compared to Comparative Example 2 in which a hole injection layer of NPD is doped with HAT-CN. Example 3 of this disclosure showed a 2.9 V decrease in operating voltage, a 2.7 cd/A increase in efficiency, and 2.9% increase in external quantum efficiency, and Example 4 showed a 3.0 V decrease in operating voltage, a 2.7 cd/A increase in efficiency, and a 2.9% increase in external quantum efficiency, compared to Comparative Example 3 in which the hole injection layer was not formed.

Also, Example 5 in which the hole injection layer comprises Compound A62 of this disclosure showed a 0.2 V decrease in operating voltage, a 0.2 cd/A increase in efficiency, and a 0.3% increase in external quantum efficiency, compared to Comparative Example 1 in which HAT-CN is used as the hole injection layer. Example 6 in which a hole injection layer of NPD is doped with Compound A62 of this disclosure showed a 2.0 V decrease in operating voltage, a 1.4 cd/A increase in efficiency, and 1.2% increase in external quantum efficiency, compared to Comparative Example 2 in which a hole injection layer of NPD is doped with HAT-CN. Example 5 of this disclosure showed a 2.8 V decrease in operating voltage, a 2.5 cd/A increase in efficiency, and 2.7% increase in external quantum efficiency, and Example 6 showed a 2.8 V decrease in operating voltage, a 2.6 cd/A increase in efficiency, and a 2.8% increase in external quantum efficiency, compared to Comparative Example 3 in which the hole injection layer was not formed.

Also, Example 7 in which the hole injection layer comprises Compound A63 of this disclosure showed a 0.1 V decrease in operating voltage, a 0.1 cd/A increase in efficiency, and a 0.3% increase in external quantum efficiency, compared to Comparative Example 1 in which HAT-CN is used as the hole injection layer. Example 8 in which a hole injection layer of NPD is doped with Compound A63 of this disclosure showed a 2.0 V decrease in operating voltage, a 1.4 cd/A increase in efficiency, and 1.1% increase in external quantum efficiency, compared to Comparative Example 2 in which a hole injection layer of NPD is doped with HAT-CN. Example 7 of this disclosure showed a 2.7 V decrease in operating voltage, a 2.4 cd/A increase in efficiency, and 2.7% increase in external quantum efficiency, and Example 8 showed a 2.8 V decrease in operating voltage, a 2.6 cd/A increase in efficiency, and a 2.7% increase in external quantum efficiency, compared to Comparative Example 3 in which the hole injection layer was not formed From these results, it can be concluded that the organic light emitting display devices of Examples 1 to 8 in which the hole injection layer comprises a compound of this disclosure achieved a reduction in operating voltage and improvements in efficiency and external quantum efficiency, compared to the organic light emitting display devices of Comparative Examples 1 to 3 in which the hole injection layer is formed of a well-known material. Also, the hole injection layer may form solely of a compound of this disclosure, or this compound may be used as a dopant.

Test 2: Device with Multiple Light Emitting Parts

Example 9

An organic light emitting display device was fabricated by forming, a first light emitting part comprising a hole injection layer, a first hole transport layer, a fluorescent blue light emitting layer, and a first electron transport layer, a charge generation layer comprising an N-type charge generation layer and a P-type charge generation layer, a second light emitting part comprising a second electron injection layer, a fluorescent blue light emitting layer, a second electron transport layer, and an electron injection layer, and a cathode on a substrate. Here, the hole injection layer and the P-type charge generation layer were formed of Compound B31. After the deposition of these layers, the device was transferred from the deposition chamber into a dry box for encapsulation, and was subsequently encapsulated using an UV-curable epoxy resin and a moisture getter. The organic light emitting display device thus obtained was connected to an external power supply source, and upon application of direct current voltage, the results in Table 2 were obtained. The characteristics of all the fabricated devices were evaluated using a constant current source (KEITHLEY) and a photometer (PR650) at room temperature. Here, the light emitting layers in the first and second light emitting parts are blue light emitting layers, but is not limited thereto.

Example 10

It has the same elements as the above-described Example 9, and the hole injection layer and the P-type charge generation layer were formed of NPD doped with 10% Compound B31.

Example 11

It has the same elements as the above-described Example 9, and the hole injection layer and the P-type charge generation layer were formed of Compound A33.

Example 12

It has the same elements as the above-described Example 9, and the hole injection layer and the P-type charge generation layer were formed of NPD doped with 10% Compound A33.

Example 13

It has the same elements as the above-described Example 9, and the hole injection layer and the P-type charge generation layer were formed of Compound A62.

Example 14

It has the same elements as the above-described Example 9, and the hole injection layer and the P-type charge generation layer were formed of NPD doped with 10% Compound A62.

Example 15

It has the same elements as the above-described Example 9, and the hole injection layer and the P-type charge generation layer were formed of Compound A63.

Example 16

It has the same elements as the above-described Example 9, and the hole injection layer and the P-type charge generation layer were formed of NPD doped with 10% Compound A63.

Comparative Example 4

It has the same elements as the above-described Example 9, and the hole injection layer and the P-type charge generation layer were formed of HAT-CN.

Comparative Example 5

It has the same elements as the above-described Example 9, and the hole injection layer and the P-type charge generation layer were formed of NPD doped with 10% HAT-CN.

Comparative Example 6

It has the same elements as the above-described Example 9, but without the hole injection layer and the P-type charge generation layer.

The operating voltage, efficiency, and external quantum efficiency of the devices fabricated according to Examples 9 to 16 of the present disclosure and Comparative Examples 4, 5, and 6 set forth above were measured and shown in the following Table 2. (The devices were driven at a drive current of 10 mA/cm$^2$ to measure the operating voltage, efficiency, and external quantum efficiency).

TABLE 2

| | Operating voltage (V) | Efficiency (Cd/A) | External quantum efficiency (%) |
|---|---|---|---|
| Example 9 | 9.2 | 5.3 | 6.4 |
| Example 10 | 8.6 | 6.5 | 7.5 |
| Example 11 | 8.2 | 7.2 | 8.3 |
| Example 12 | 8.1 | 7.2 | 8.3 |
| Example 13 | 8.4 | 6.7 | 7.8 |
| Example 14 | 8.5 | 6.7 | 7.7 |
| Example 15 | 8.5 | 6.7 | 7.7 |
| Example 16 | 8.4 | 6.8 | 7.8 |
| Comparative Example 4 | 9.1 | 5.4 | 6.6 |
| Comparative Example 5 | 13.5 | 4.5 | 5.1 |
| Comparative Example 6 | — | — | — |

Referring to Table 2, Example 9 in which the hole injection layer and the P-type charge generation layer comprise Compound B31 of this disclosure and Comparative Example 4 in which HAT-CN is used as the hole injection layer and the P-type charge generation layer showed similar levels of operating voltage, efficiency, and external quantum efficiency. Example 10 in which a hole injection layer and P-type charge generation layer of NPD are doped with Compound B31 of this disclosure showed a 4.9 V decrease in operating voltage, a 2.0 cd/A increase in efficiency, and 2.4% increase in external quantum efficiency, compared to Comparative Example 5 in which a hole injection layer and P-type charge generation layer of NPD are doped with HAT-CN.

Also, Example 11 in which the hole injection layer and the P-type charge generation layer comprise Compound A33 of this disclosure showed a 0.9 V decrease in operating voltage, a 1.8 cd/A increase in efficiency, and a 1.7% increase in external quantum efficiency, compared to Comparative Example 4 in which HAT-CN is used as the hole injection layer and the P-type charge generation layer. Example 12 in which a hole injection layer and P-type charge generation layer of NPD are doped with Compound A33 of this disclosure showed a 5.4 V decrease in operating voltage, a 2.7 cd/A increase in efficiency, and 3.2% increase in external quantum efficiency, compared to Comparative Example 5 in which a hole injection layer and P-type charge generation layer of NPD are doped with HAT-CN.

Also, Example 13 in which the hole injection layer and the P-type charge generation layer comprise Compound A62 of this disclosure showed a 0.7 V decrease in operating voltage, a 1.3 cd/A increase in efficiency, and a 1.2% increase in external quantum efficiency, compared to Comparative Example 4 in which HAT-CN is used as the hole injection layer and the P-type charge generation layer. Example 14 in which a hole injection layer and P-type charge generation layer of NPD are doped with Compound A62 of this disclosure showed a 5.0 V decrease in operating voltage, a 2.2 cd/A increase in efficiency, and 2.6% increase in external quantum efficiency, compared to Comparative Example 5 in which a hole injection layer and P-type charge generation layer of NPD are doped with HAT-CN.

Also, Example 15 in which the hole injection layer and the P-type charge generation layer comprise Compound A63 of this disclosure showed a 0.6 V decrease in operating voltage, a 1.3 cd/A increase in efficiency, and a 1.1% increase in external quantum efficiency, compared to Comparative Example 4 in which HAT-CN is used as the hole injection layer and the P-type charge generation layer. Example 16 in which a hole injection layer and P-type charge generation layer of NPD are doped with Compound A63 of this disclosure showed a 5.1 V decrease in operating voltage, a 2.3 cd/A increase in efficiency, and 2.7% increase in external quantum efficiency, compared to Comparative Example 5 in which a hole injection layer and P-type charge generation layer of NPD are doped with HAT-CN.

In Comparative Example 6 in which the hole injection layer was not formed, the device could not be driven.

Also, at least one among the hole injection layer and the P-type charge generation layer may form solely of a compound of this disclosure, or this compound may be used as a dopant.

For reference, the energy levels of the well-known compounds and the compounds used in the examples of the present disclosure are shown in the following Table 3. The energy levels are calculated by DFT (Density Functional Theory) simulation. The DFT is one of the electronic structure computational methods. The function (basis set) used in the simulation is B3LYP/6-31G*, but is not limited thereto.

TABLE 3

| | HOMO (eV) | LUMO (eV) |
|---|---|---|
| NPD | −5.45 | −2.30 |
| HAT-CN | −9.55 | −6.07 |
| $F_4$-TCNQ | −8.33 | −5.78 |
| B31 | −7.9 | −5.72 |

Referring to Table 3, it can be found out that a compound of this disclosure showed a LUMO energy level closer to −5.45 eV, which is the HOMO energy level of NPD used as a host for the hole injection layer or P-type charge generation layer, compared to HAT-CN and $F_4$-TCNQ, known as p-type dopant materials. As such, the LUMO energy level of the compound of this disclosure is similar to or lower than the HOMO energy level of the host for the hole injection layer or P-type charge generation layer, which may lead to an improvement in the hole injection properties.

From these results, it can be concluded that the organic light emitting display device of Example 9 in which the hole injection layer and the P-type charge generation layer comprise a compound of this disclosure achieved almost the same levels of operating voltage, efficiency, and external quantum efficiency as the organic light emitting display device of Comparative Example 4. Also, it can be concluded that the organic light emitting display device of Example 10 in which the hole injection layer and the P-type charge generation layer comprise a compound of this disclosure achieved a 4.9 V decrease in operating voltage, a 2.0 cd/A increase in efficiency, and a 2.4% increase in external quantum efficiency, compared to the organic light emitting display device of Comparative Example 5.

As discussed above, a compound of this disclosure comprises indene as a core, which provides process stability against heat or deposition, thus simplifying the composition and deposition of the compound. Moreover, the compound of this disclosure can improve the hole injection properties by comprising an electron-attracting substituent attached to the core and making the LUMO energy level of the compound similar to or lower than the HOMO energy level of host of the hole injection layer, the host of the P-type charge generation layer, or the hole transport layer.

Accordingly, at least one among the hole injection layer and the P-type charge generation layer is formed of the compound of this disclosure to ensure the process stability of the compound, which simplifies the fabrication of the organic light emitting display device. Moreover, the compound of this disclosure can reduce the device's operating voltage and improve its efficiency and lifetime since the improvement in hole injection properties helps to facilitate the transfer of holes from the anode to the light emitting layer.

It will be apparent to those skilled in the art that various modifications and variations can be made in the organic light emitting display device of the present disclosure without departing from the spirit or scope of the disclosure. Thus, it is intended that the present disclosure cover the modifications and variations of this disclosure provided they come within the scope of the appended claims and their equivalents.

The invention claimed is:

1. An organic light emitting display device, comprising:

at least one light emitting part between an anode and a cathode, wherein the at least one light emitting part comprises at least one organic layer, wherein the at least one organic layer comprises a first P-type charge generation layer, wherein the first P-type charge generation layer comprises a compound represented by Chemical Formula 1:

Chemical Formula 1

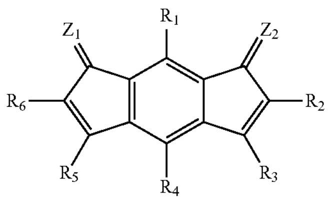

where $R_1$ to $R_6$ include independently one among hydrogen, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted or unsubstituted alkyl group with 1 to 12 carbon atoms, a substituted or unsubstituted alkoxy group with 1 to 12 carbon atoms, a substituted or unsubstituted ether group with 2 to 12 carbon atoms, a cyano group, a fluorine group, a trifluoromethyl group, a trifluoromethoxy group, and a trimethylsilyl group, and at least one of $R_1$ to $R_6$ comprises a cyano group, and $Z_1$ and $Z_2$ are independently represented by the following Chemical Formula 2:

Chemical Formula 2

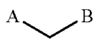

where A and B independently represent one among a hydrogen atom, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted or unsubstituted alkyl group with 1 to 12 carbon atoms, a substituted or unsubstituted alkoxy group with 1 to 12 carbon atoms, a substituted or unsubstituted ether group with 2 to 12 carbon atoms, a cyano group, a fluorine group, a trifluoromethyl group, a trifluoromethoxy group, and a trimethylsilyl group, wherein $Z_1$ and $Z_2$ are attached via a double bond between a carbon atom bound to A and B of Chemical Formula 2 and the indacene ring of Chemical Formula 1.

2. The organic light emitting display device of claim 1, wherein a substituent of the substituted aryl group, the substituted heteroaryl group, the substituted alkyl group, the substituted alkoxy group or the substituted ether group includes an alkyl with 2 to 12 carbon atoms, an aryl with 6 to 15 carbon atoms, a hetero alkyl with 1 to 15 carbon atoms and 1 to 4 heteroatoms one among O, N, S, and Si, a cyano group, a fluorine group, a trifluoromethyl group, a trifluoromethoxy group, or a trimethylsilyl group.

3. The organic light emitting display device of claim 1, wherein the compound represented by Chemical Formula 1 is one among the following compounds:

B1

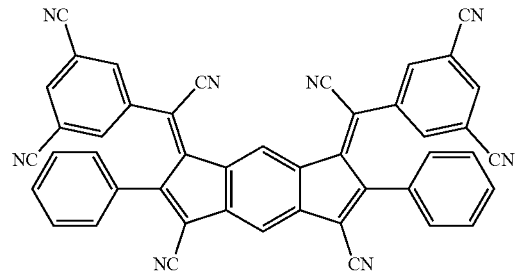

B2

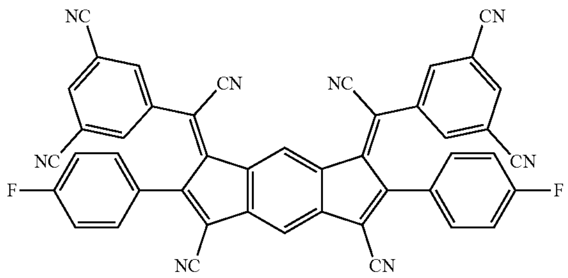

B3

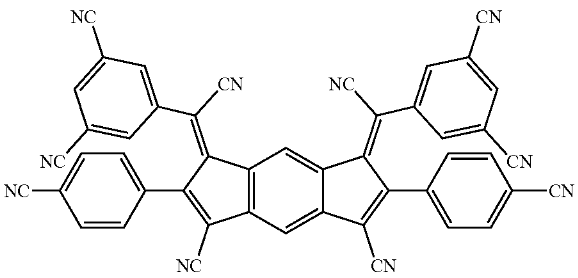

-continued

B4

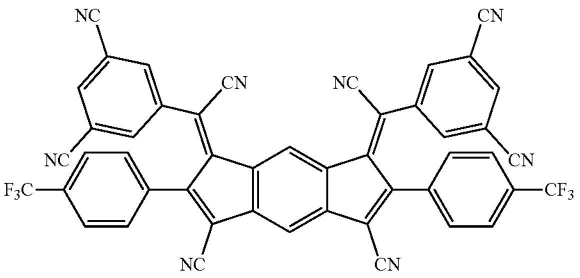

B5

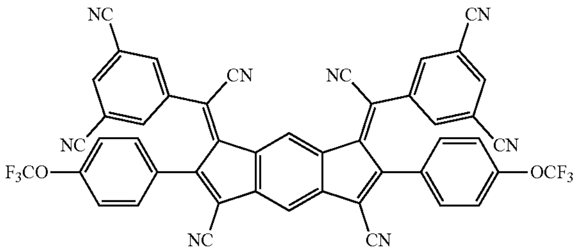

B6

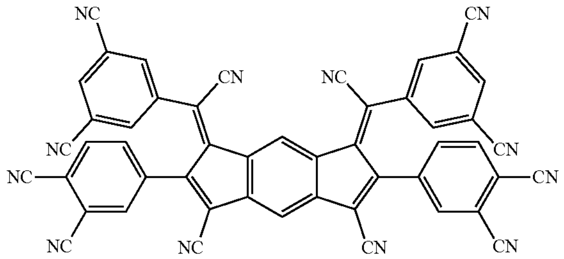

B7

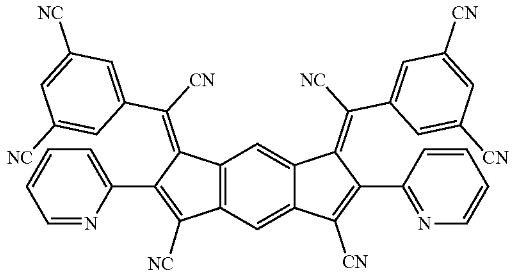

B8

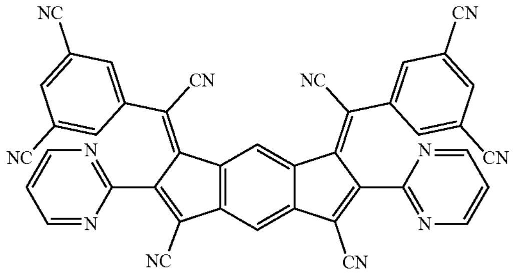

-continued
B9
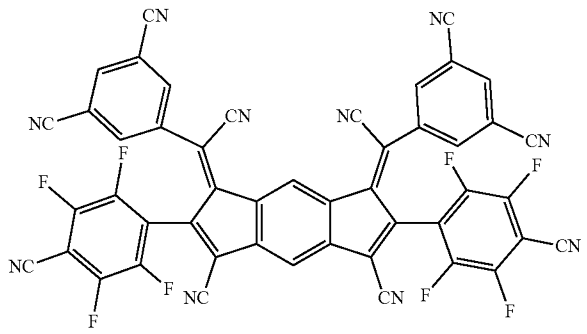
B10
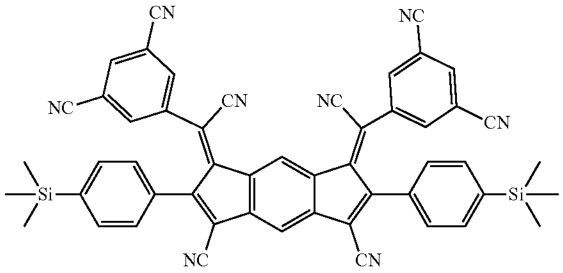
B11
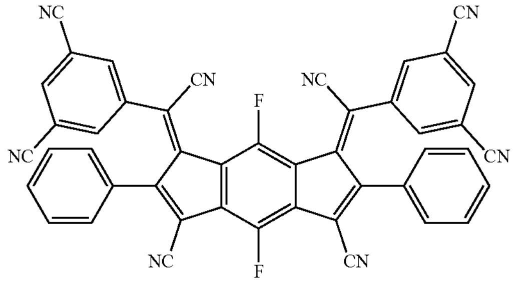
B12
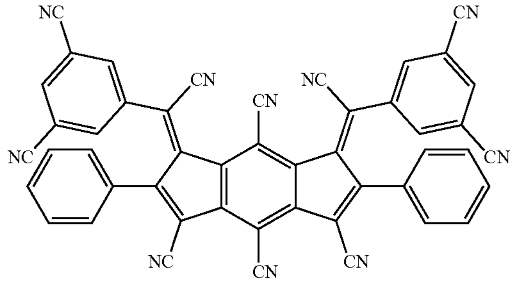
B13
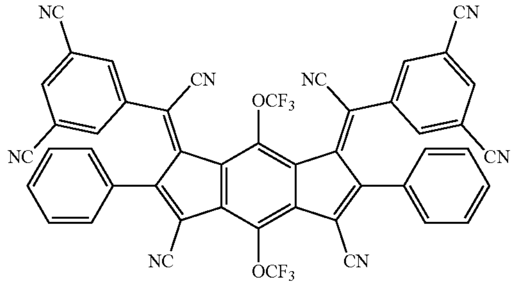
-continued
B14
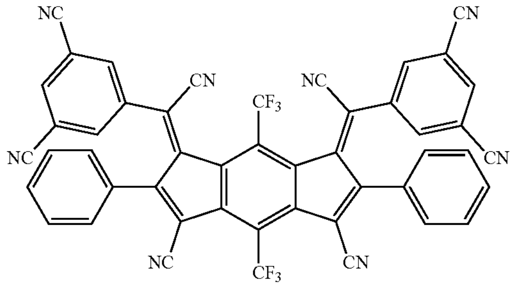
B15
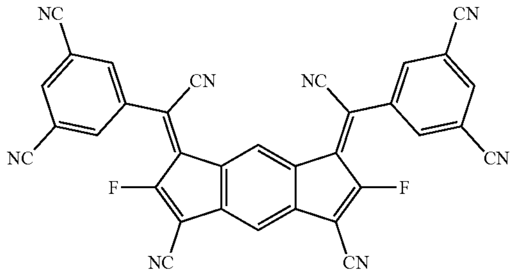
B16
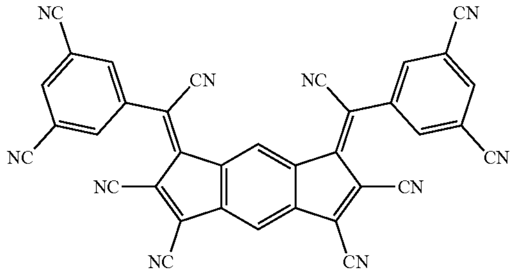
B17
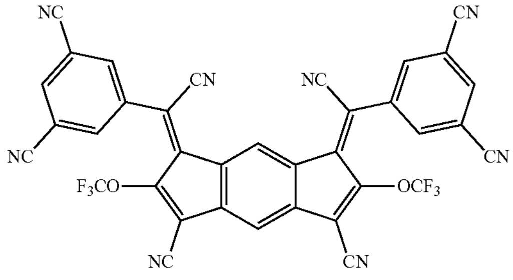
B18
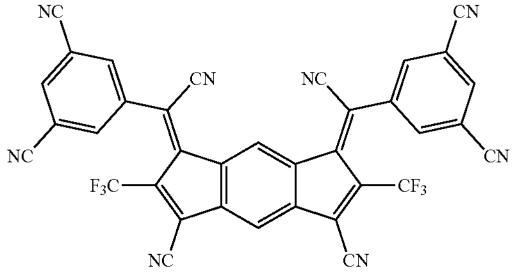

-continued
B19
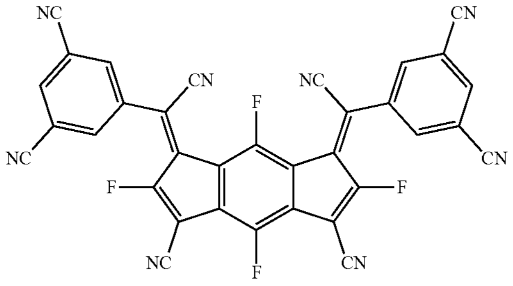
B20
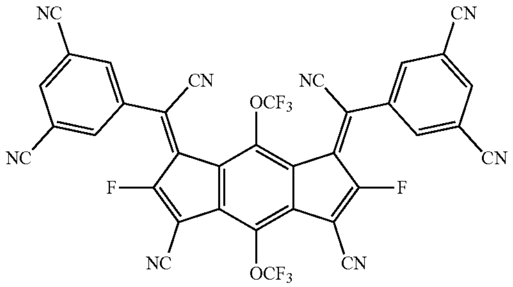
B21
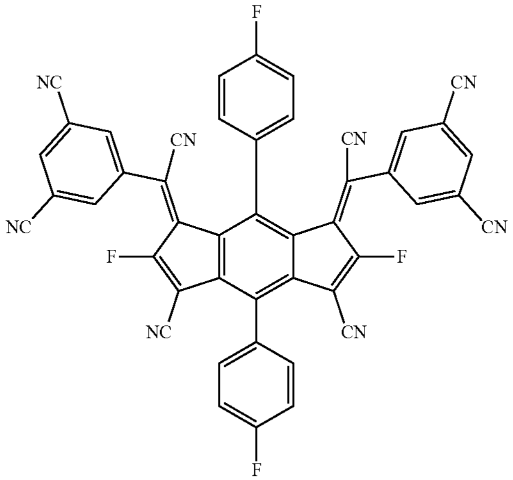
B22
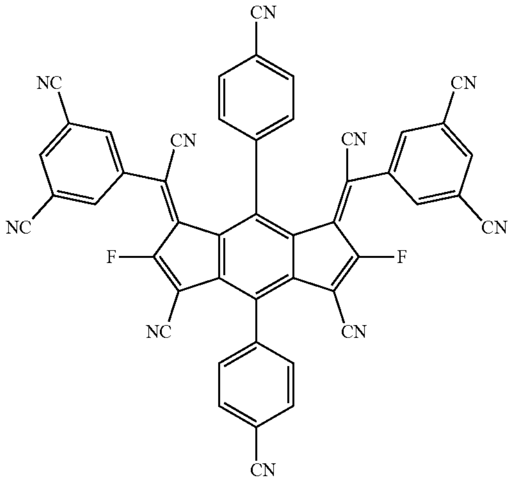
-continued
B23
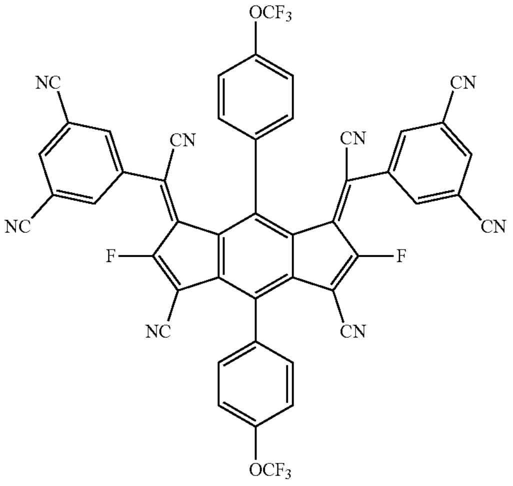
B24
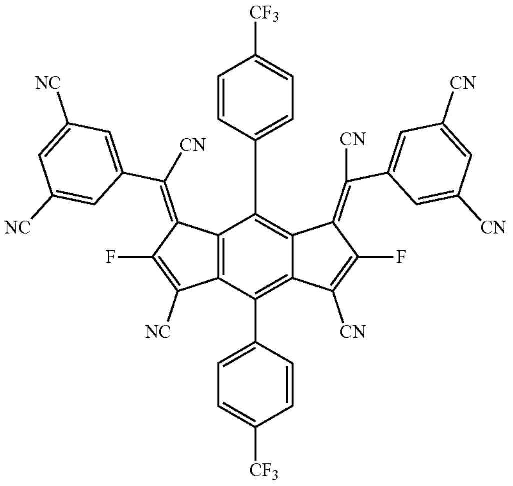
B25
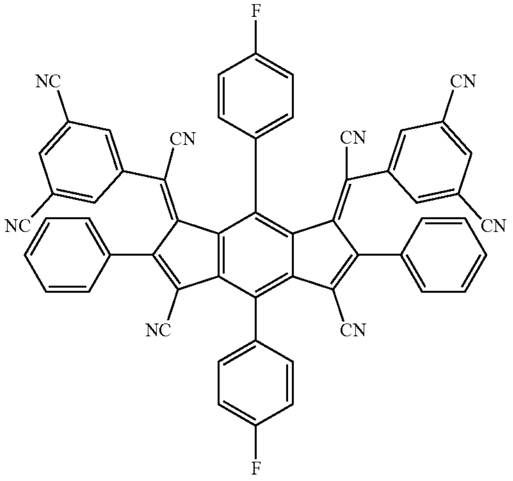

-continued
B26
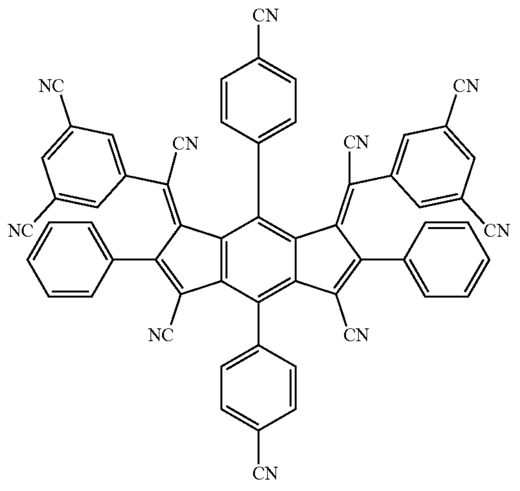
B27
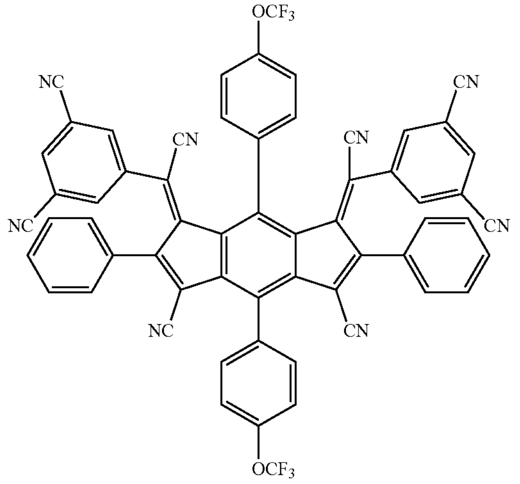
B28
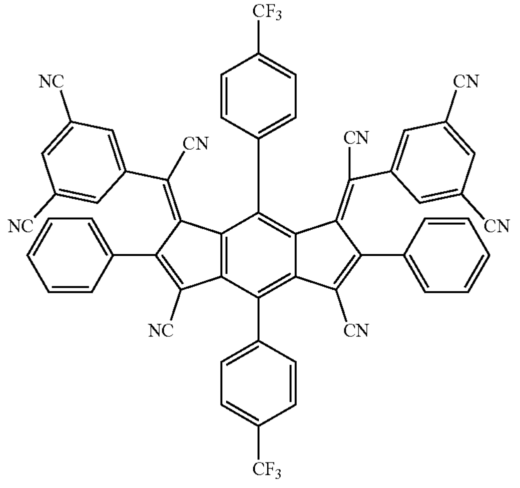
-continued
B29
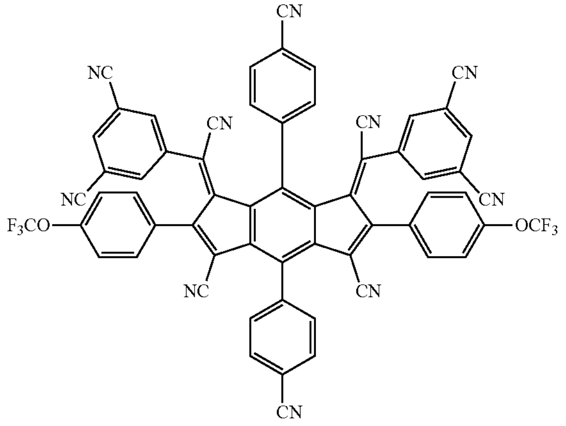
B30
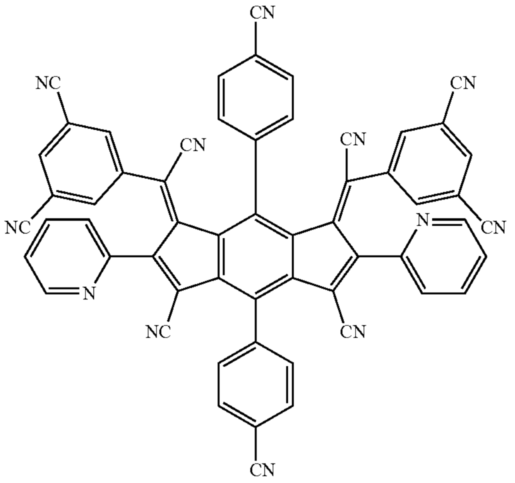
B31
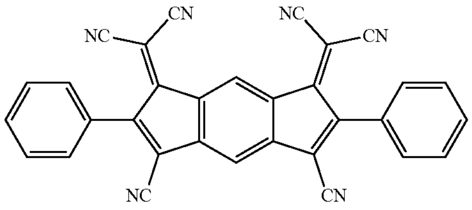
B32
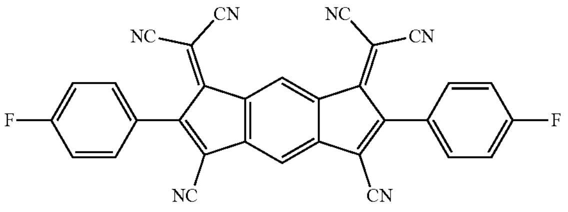
B33
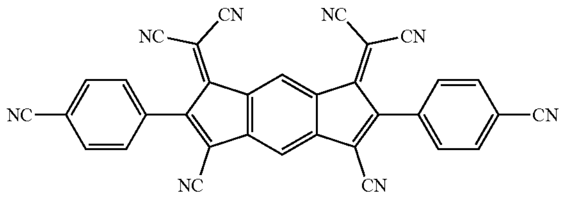

-continued
B34
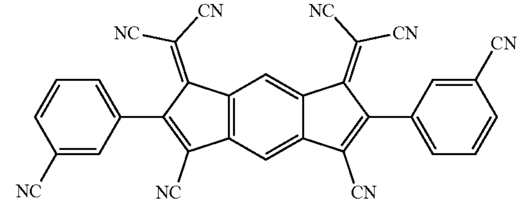
B35
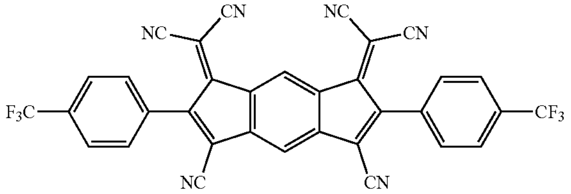
B36
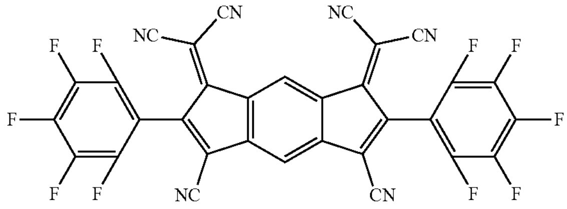
B37
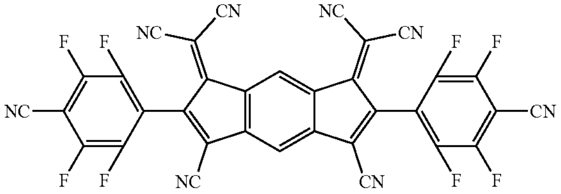
B38
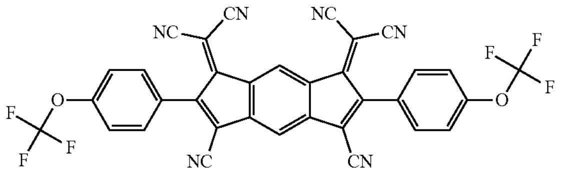
B39
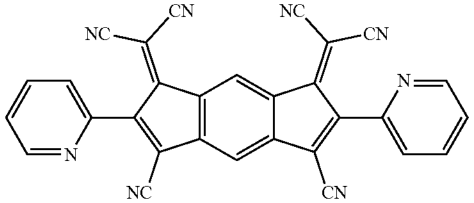
B40
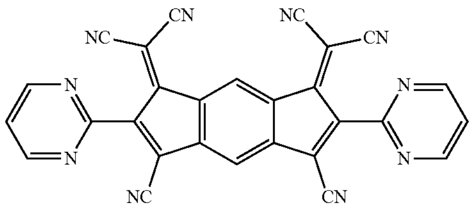
-continued
B41
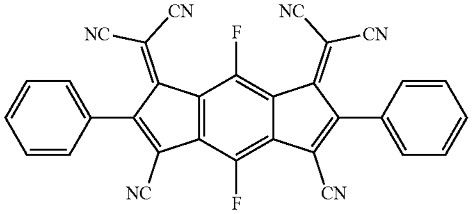
B42
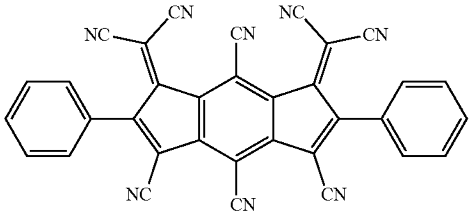
B43
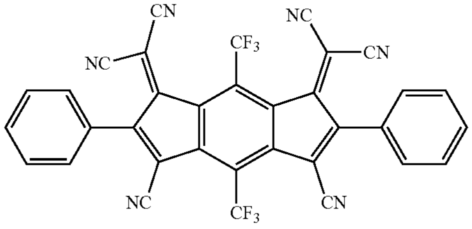
B44
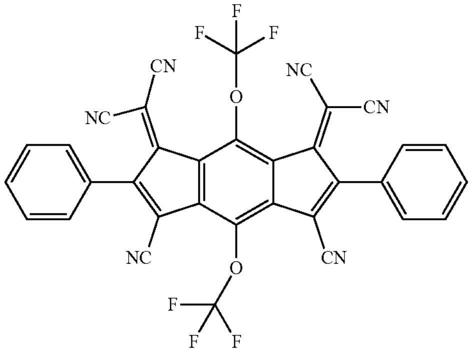
B45
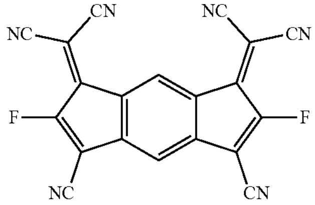
B46
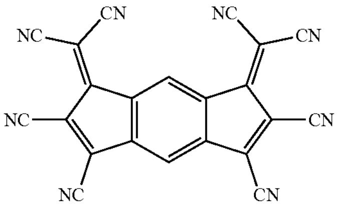

-continued

B47

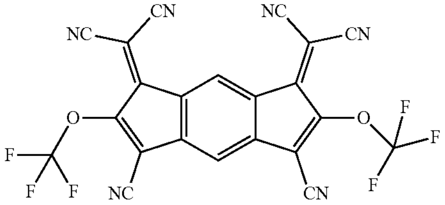

B48

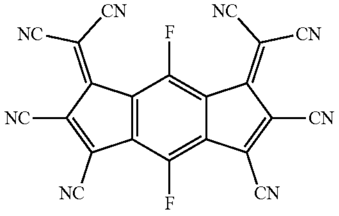

B49

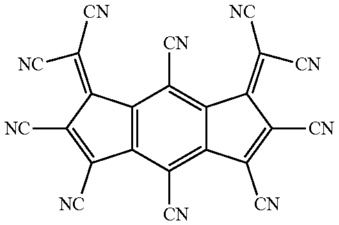

B50

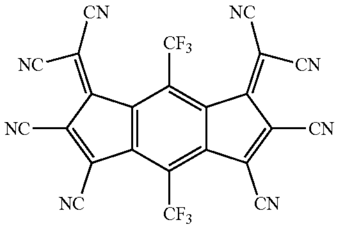

B51

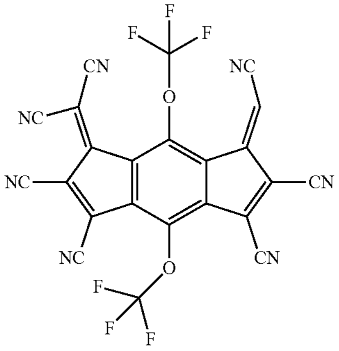

B52

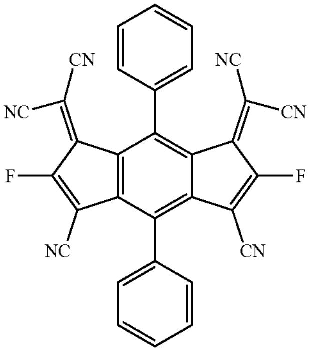

-continued

B53

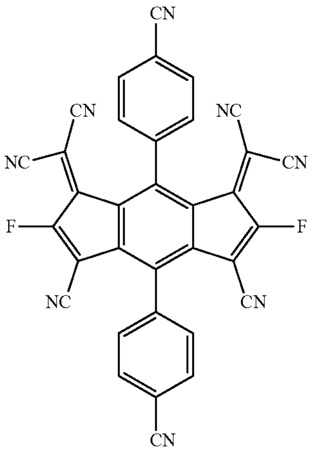

B54

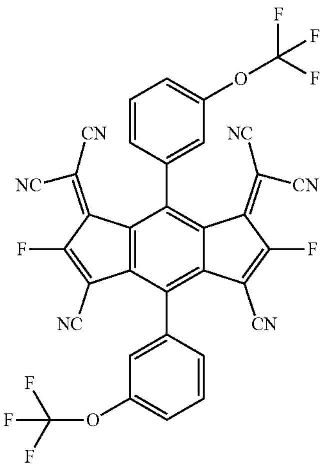

B55

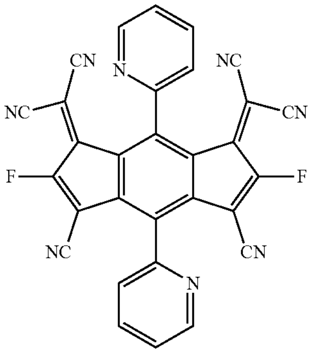

B56

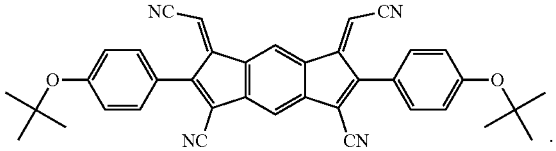

.

4. The organic light emitting display device of claim 1, wherein a dopant of the first P-type charge generation layer includes the compound represented by Chemical Formula 1.

5. The organic light emitting display device of claim 3, wherein a dopant of the first P-type charge generation layer includes the compound represented by Chemical Formula 1.

6. The organic light emitting display device of claim 1, wherein the at least one light emitting part includes a first light emitting part and a second light emitting part, wherein the first light emitting part includes a first light emitting layer, and wherein the second light emitting part includes a second light emitting layer.

7. The organic light emitting display device of claim 6, wherein:

the first light emitting layer emits light of a color of at least one among red, green, and blue; and the second light emitting layer emits light of a color of at least one among red, green, and blue.

8. The organic light emitting display device of claim 6, wherein the first light emitting layer and the second light emitting layer emit light of the same color.

9. The organic light emitting display device of claim 6, wherein the at least one organic layer includes a hole injection layer including the compound represented by Chemical Formula 1.

10. The organic light emitting display device of claim 3, wherein the at least one organic layer includes a hole injection layer including the compound represented by Chemical Formula 1.

11. The organic light emitting display device of claim 6, wherein:

the first light emitting layer includes a blue light emitting layer, a dark blue emitting layer, a sky blue emitting layer, a combination of a blue light emitting layer and a red light emitting layer, a combination of a blue light emitting layer and a yellow-green emitting layer, or a combination of a blue light emitting layer and a green emitting layer; and the second light emitting layer includes a yellow-green emitting layer, a green emitting layer, a combination of a yellow-green emitting layer and a green emitting layer, a combination of a yellow emitting layer and a red emitting layer, a combination of a green emitting layer and a red emitting layer, or a combination of a yellow-green emitting layer and a red emitting layer.

12. The organic light emitting display device of claim 1, wherein the at least one light emitting part includes a first light emitting part, a second light emitting part, and a third light emitting part, and the first light emitting part includes a first light emitting layer, the second light emitting part includes a second light emitting layer, and the third light emitting part includes a third light emitting layer.

13. The organic light emitting display device of claim 12, wherein:

the first light emitting layer includes a blue light emitting layer, a dark blue emitting layer, a sky blue emitting layer, a combination of a blue light emitting layer and a red light emitting layer, a combination of a blue light emitting layer and a yellow-green emitting layer, or a combination of a blue light emitting layer and a green emitting layer;

the second light emitting layer includes a yellow-green emitting layer, a green emitting layer, a combination of a yellow-green emitting layer and a green emitting layer, a combination of a yellow emitting layer and a red emitting layer, a combination of a green emitting layer and a red emitting layer, or a combination of a yellow-green emitting layer and a red emitting layer; and the third light emitting layer includes a blue light emitting layer, a dark blue emitting layer, a sky blue emitting layer, a combination of a blue light emitting layer and a red light emitting layer, a combination of a blue light emitting layer and a yellow-green emitting layer, or a combination of a blue light emitting layer and a green emitting layer.

14. The organic light emitting display device of claim 12, further comprising a second P-type charge generation layer between the second light emitting part and the third light emitting part, a dopant of the second P-type generation layer including the compound.

15. An organic light emitting display device, comprising:

a first light emitting part between an anode and a cathode;

a second light emitting part on the first light emitting part; and a charge generation layer having a first P-type charge generation layer between the first light emitting part and the second light emitting part, wherein the first P-type charge generation layer comprises a compound represented by Chemical Formula 1:

Chemical Formula 1

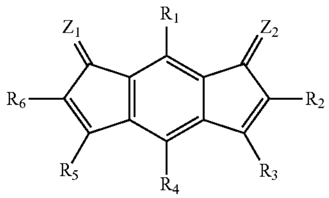

where $R_1$ to $R_6$ each independently represents one among a hydrogen atom, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted alkyl group with 1 to 12 carbon atoms, a substituted or unsubstituted alkoxy group with 1 to 12 carbon atoms, a substituted or unsubstituted ether group with 2 to 12 carbon atoms, a cyano group, a fluorine group, a trifluoromethyl group, a trifluoromethoxy group, and a trimethylsilyl group, and at least one among $R_1$ to $R_6$ comprises a cyano group, and $Z_1$ and $Z_2$ are independently represented by the following Chemical Formula 2:

Chemical Formula 2

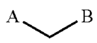

where A and B independently represent one among a hydrogen atom, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted or unsubstituted alkyl group with 1 to 12 carbon atoms, a substituted or unsubstituted alkoxy group with 1 to 12 carbon atoms, a substituted or unsubstituted ether group with 2 to 12 carbon atoms, a cyano group, a fluorine group, a trifluoromethyl group, a trifluoromethoxy group, and a trimethylsilyl group, wherein $Z_1$ and $Z_2$ are attached via a double bond between a carbon atom bound to A and B of Chemical Formula 2 and the indacene ring of Chemical Formula 1.

16. The organic light emitting display device of claim 15, wherein a substituent of the substituted aryl group, the substituted heteroaryl group, the substituted alkyl group, the substituted alkoxy group, or the substituted ether group includes an alkyl with 2 to 12 carbon atoms, an aryl with 6 to 15 carbon atoms, a hetero alkyl with 1 to 15 carbon atoms and 1 to 4 heteroatoms one among O, N, S, and Si, a cyano group, a fluorine group, a trifluoromethyl group, a trifluoromethoxy group, or a trimethylsilyl group.

17. The organic light emitting display device of claim 15, wherein the compound represented by Chemical Formula 1 is one among the following compounds:

B1

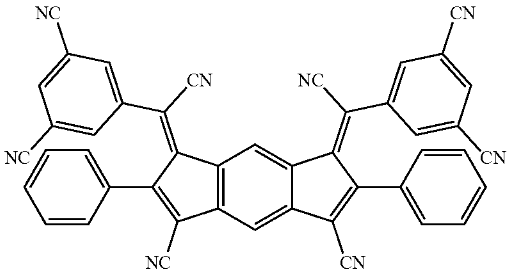

B2

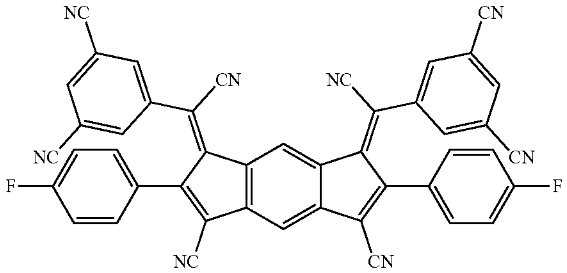

B3

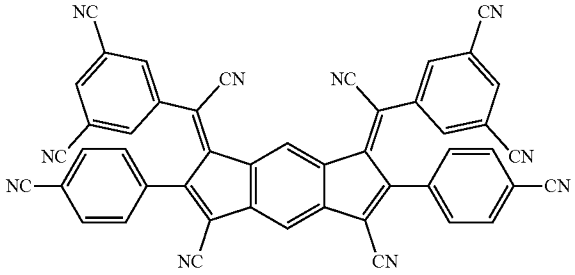

B4

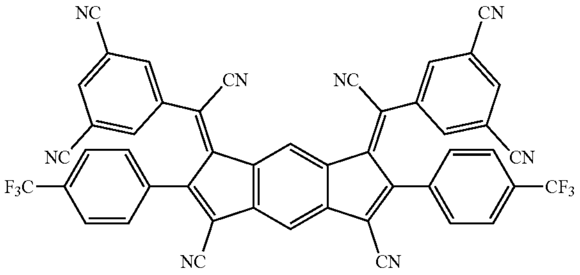

-continued

B5

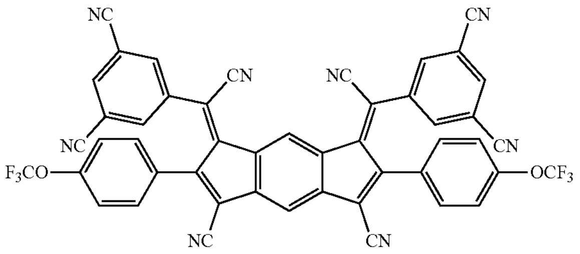

B6

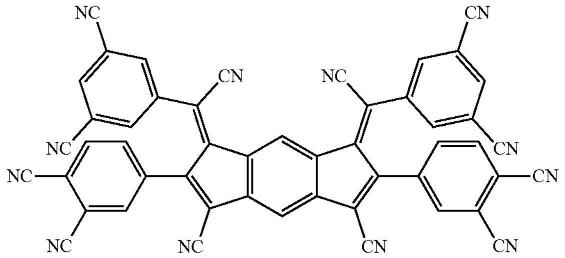

B7

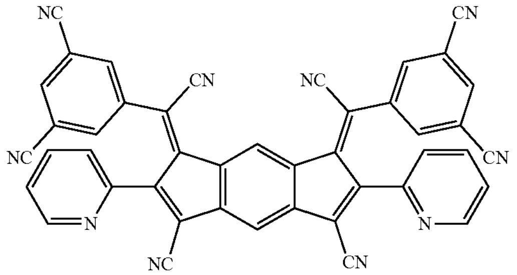

B8

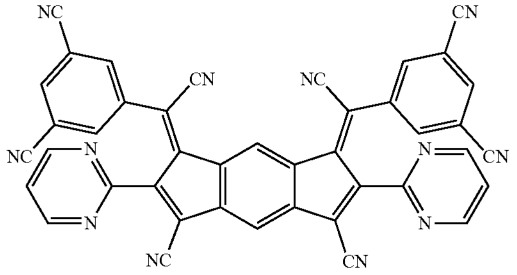

B9

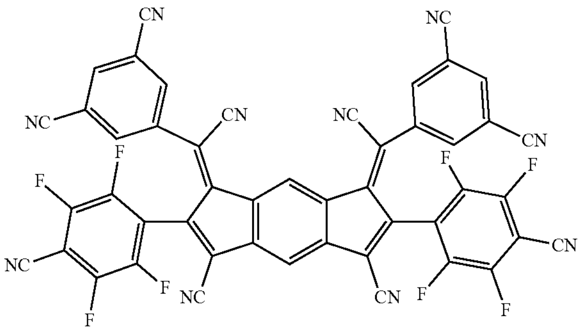

-continued
B10
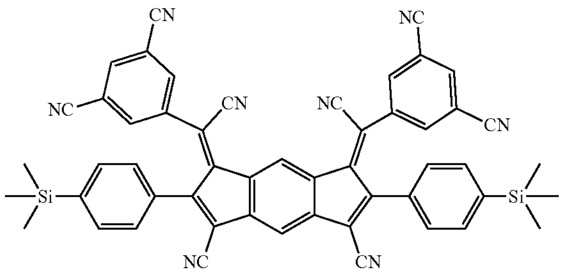
B11
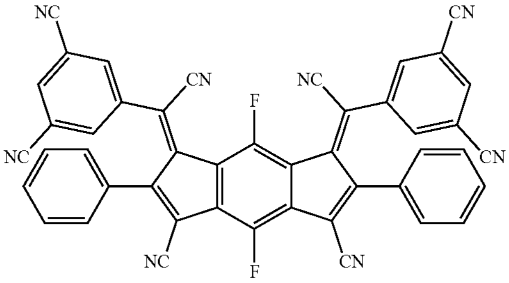
B12
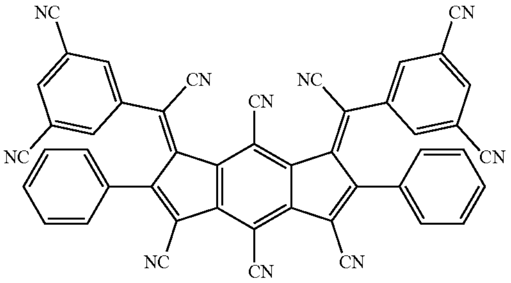
B13
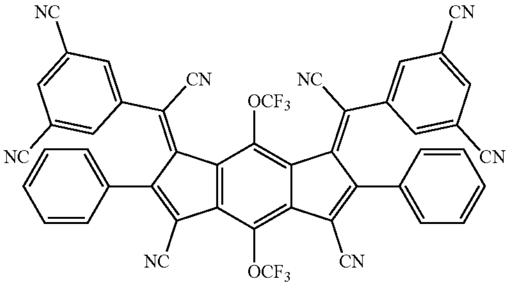
B14
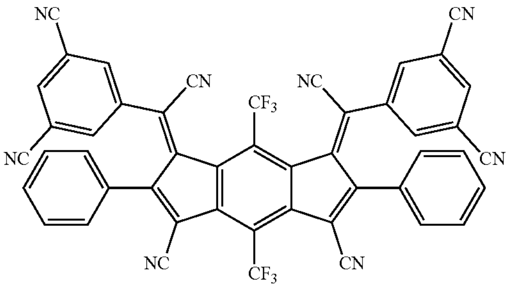
-continued
B15
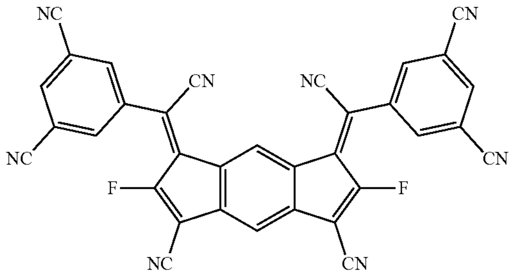
B16
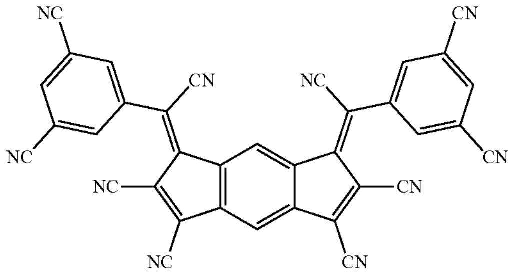
B17
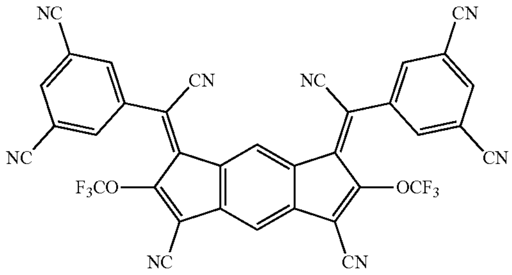
B18
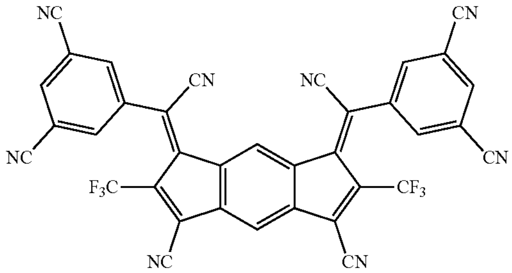
B19
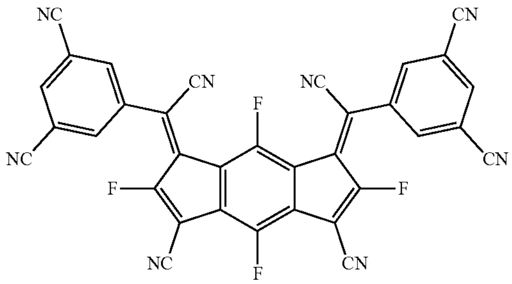

B20
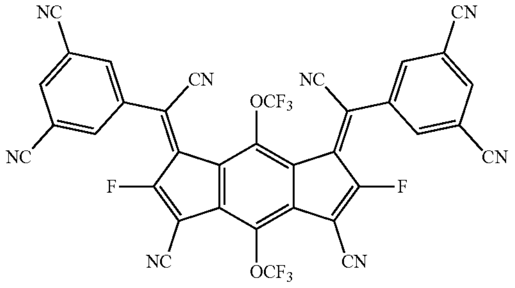
B21
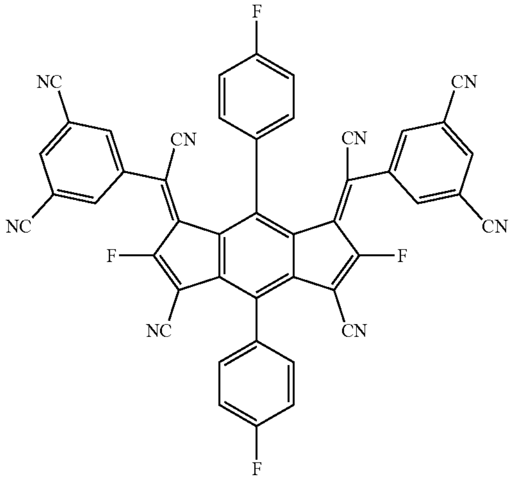
B22
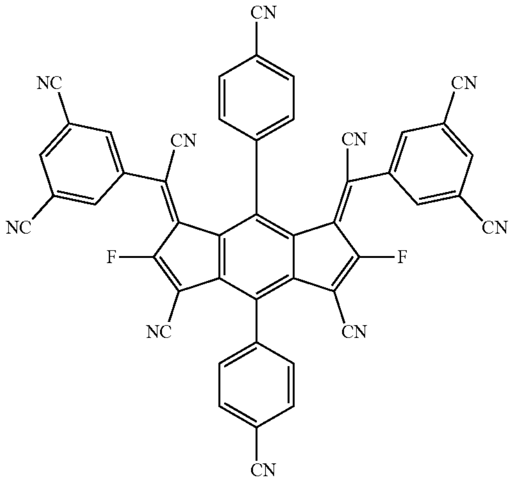
B23
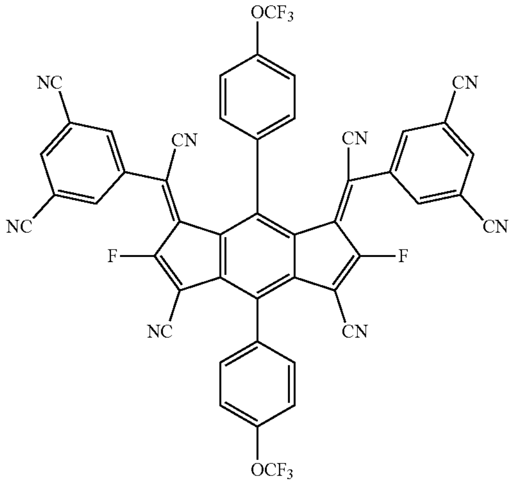
B24
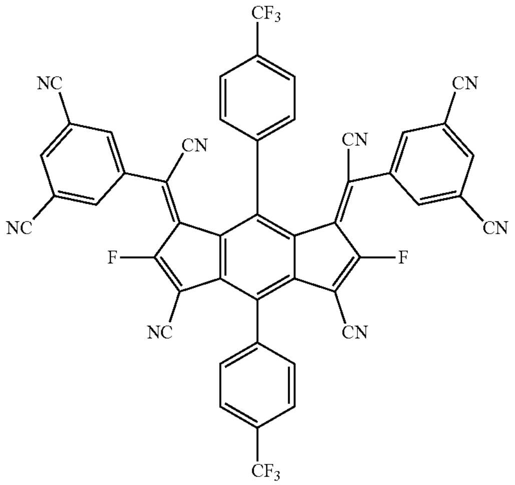
B25
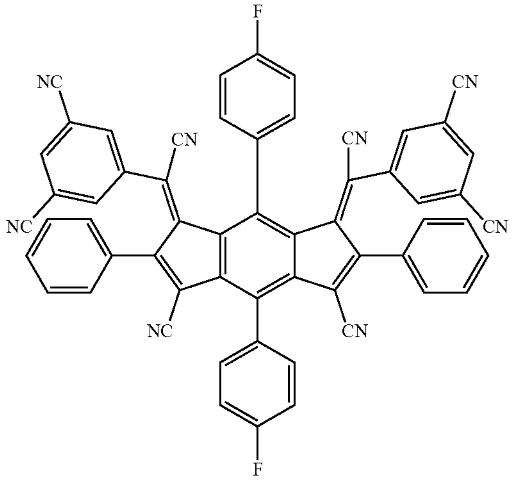

-continued
B26
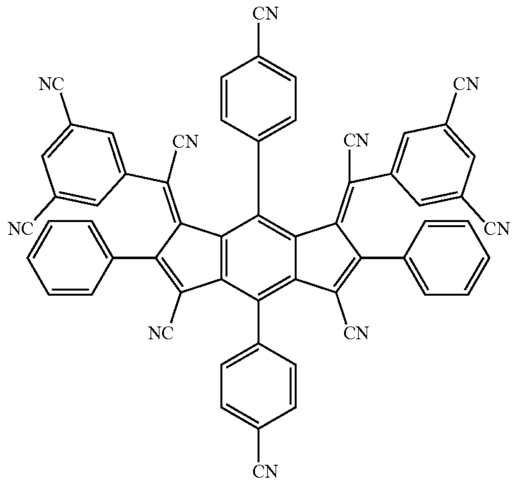
B27
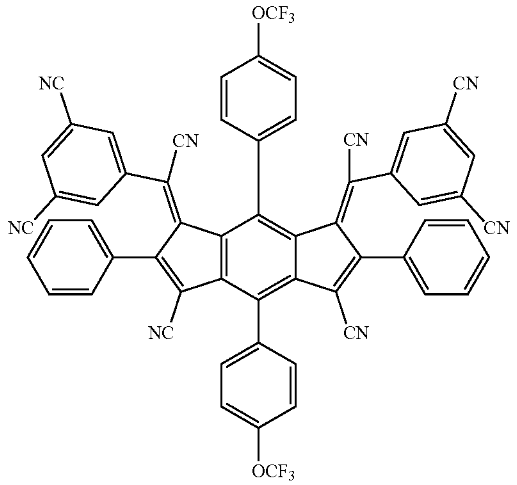
B28
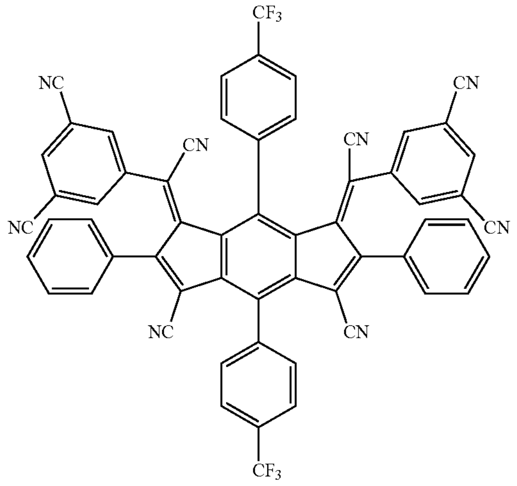
-continued
B29
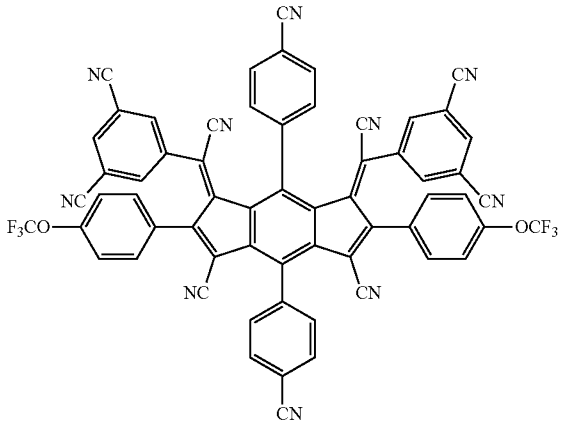
B30
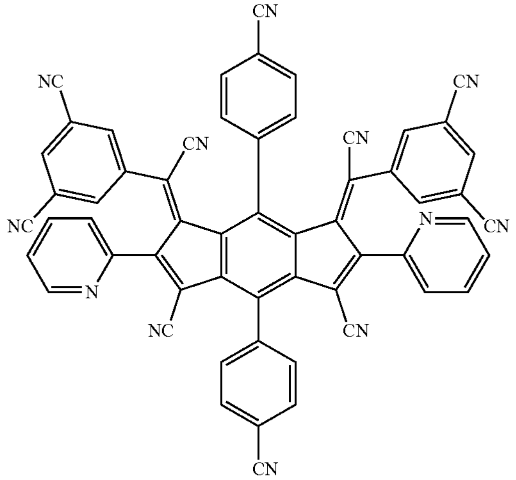
B31
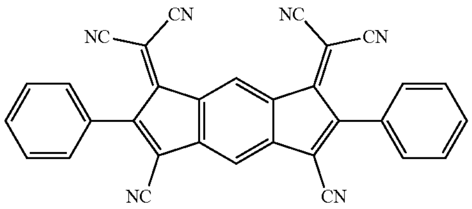
B32
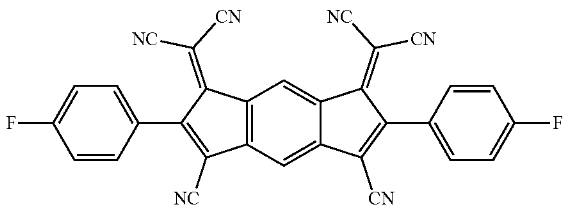
B33
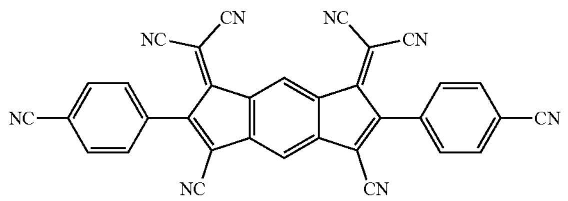

-continued
B34
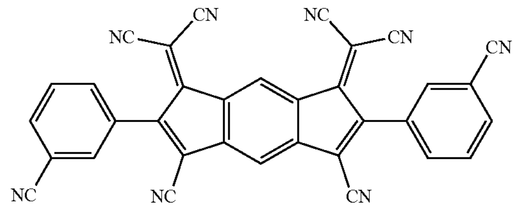
B35
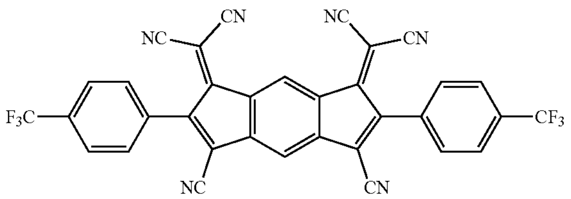
B36
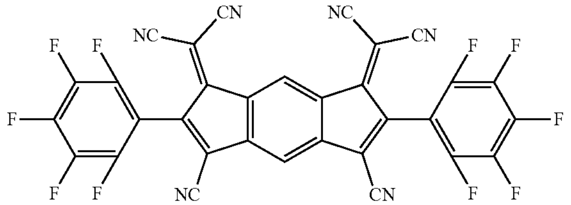
B37
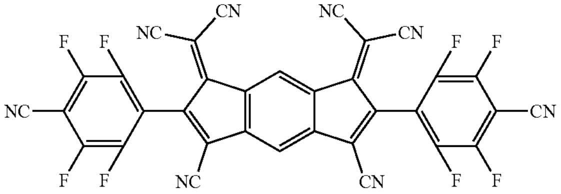
B38
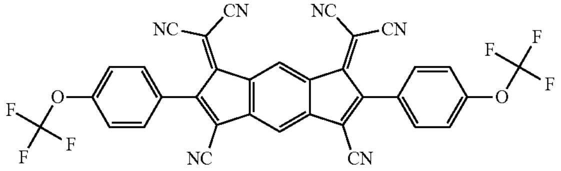
B39
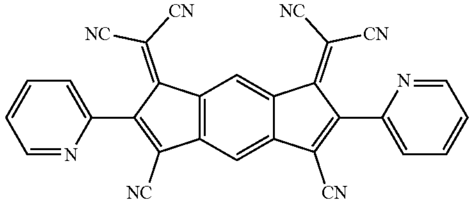
B40
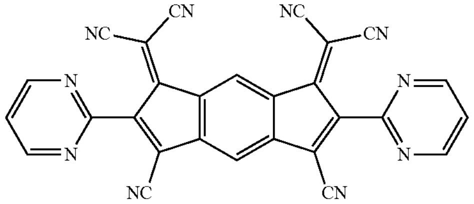
-continued
B41
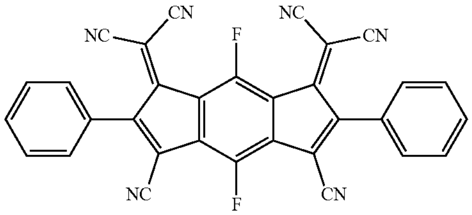
B42
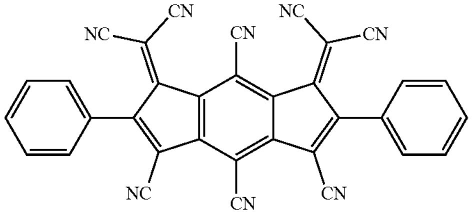
B43
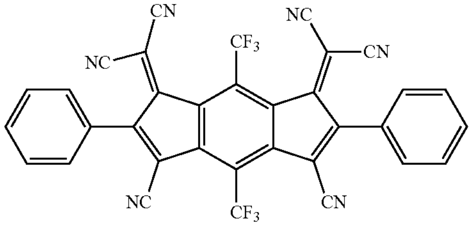
B44
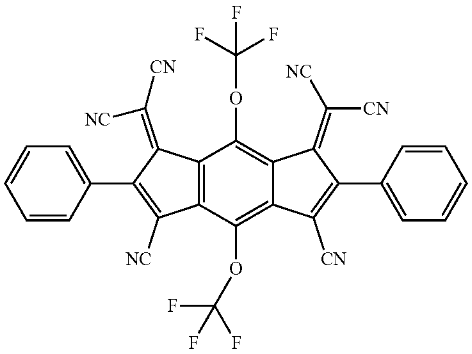
B45
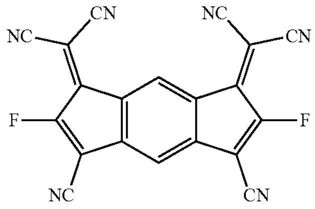
B46
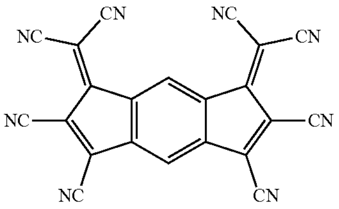

-continued

B47

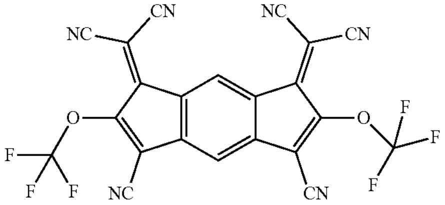

B48

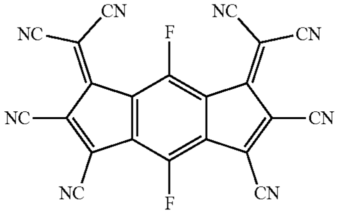

B49

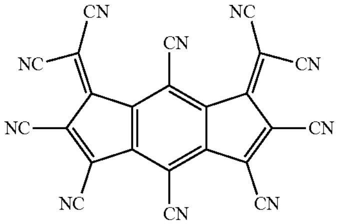

B50

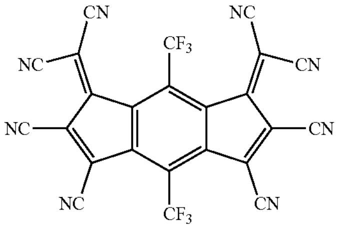

B51

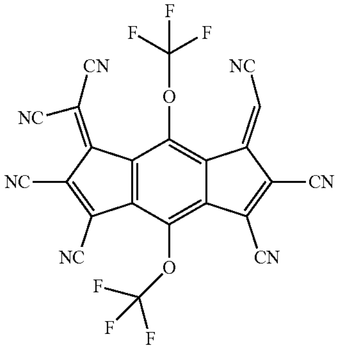

B52

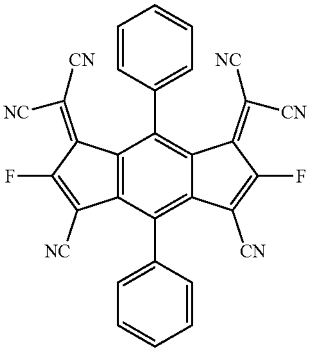

-continued

B53

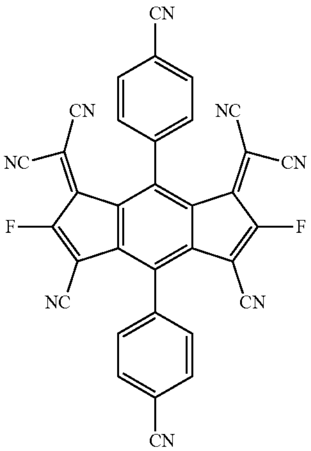

B54

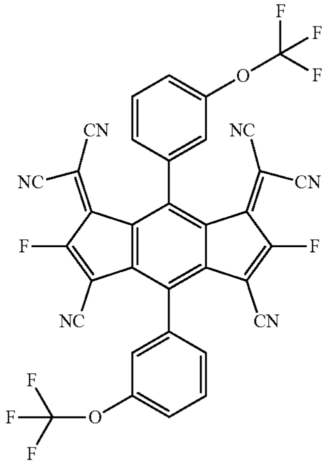

B55

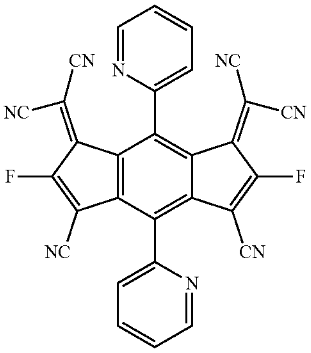

B56

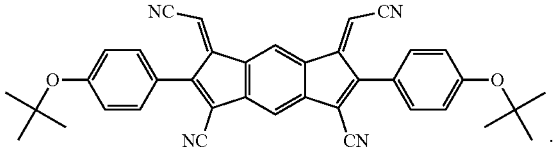

.

18. The organic light emitting display device of claim 15, wherein a dopant of the first P-type charge generation layer includes the compound represented by Chemical Formula 1.

19. The organic light emitting display device of claim 17, wherein a dopant of the first P-type charge generation layer includes the compound represented by Chemical Formula 1.

20. The organic light emitting display device of claim 15, wherein the first light emitting part includes a first light emitting layer and the second light emitting part includes a second light emitting layer.

21. The organic light emitting display device of claim 20, wherein:

the first light emitting layer emits light of a color of at least one among red, green, and blue; and the second light emitting layer emits light of a color of at least one among red, green, and blue.

22. The organic light emitting display device of claim 20, wherein the first light emitting layer and the second light emitting layer emit light of the same color.

23. The organic light emitting display device of claim 17, wherein the first light emitting part further includes a hole injection layer including the compound represented by Chemical Formula 1.

24. The organic light emitting display device of claim 20, wherein the first light emitting part further includes a hole injection layer including the compound represented by Chemical Formula 1.

25. The organic light emitting display device of claim 20, wherein:

the first light emitting layer includes a blue light emitting layer, a dark blue emitting layer, a sky blue emitting layer, a combination of a blue light emitting layer and a red light emitting layer, a combination of a blue light emitting layer and a yellow-green emitting layer, or a combination of a blue light emitting layer and a green emitting layer; and the second light emitting layer includes a yellow-green emitting layer, a green emitting layer, a combination of a yellow-green emitting layer and a green emitting layer, a combination of a yellow emitting layer and a red emitting layer, a combination of a green emitting layer and a red emitting layer, or a combination of a yellow-green emitting layer and a red emitting layer.

26. The organic light emitting display device of claim 15, wherein:

the at least one light emitting part includes a first light emitting part, a second light emitting part, and a third light emitting part, the first light emitting part includes a first light emitting layer, the second light emitting part includes a second light emitting layer, and the third light emitting part includes a third light emitting layer.

27. The organic light emitting display device of claim 26, wherein:

the first light emitting layer includes a blue light emitting layer, a dark blue emitting layer, a sky blue emitting layer, a combination of a blue light emitting layer and a red light emitting layer, a combination of a blue light emitting layer and a yellow-green emitting layer, or a combination of a blue light emitting layer and a green emitting layer;

the second light emitting layer includes a yellow-green emitting layer, a green emitting layer, a combination of a yellow-green emitting layer and a green emitting layer, a combination of a yellow emitting layer and a red emitting layer, a combination of a green emitting layer and a red emitting layer, or a combination of a yellow-green emitting layer and a red emitting layer; and the third light emitting layer includes a blue light emitting layer, a dark blue emitting layer, a sky blue emitting layer, a combination of a blue light emitting layer and a red light emitting layer, a combination of a blue light emitting layer and a yellow-green emitting layer, or a combination of a blue light emitting layer and a green emitting layer.

28. The organic light emitting display device of claim 26, further comprising a second P-type charge generation layer between the second light emitting part and the third light emitting part, and a dopant of the second P-type generation layer including the compound represented by Chemical Formula 1.

29. An organic light emitting display device, comprising:

a hole injection layer on an anode;

a hole transport layer on the hole injection layer;

a light emitting layer on the hole transport layer;

an electron transport layer on the light emitting layer; and a cathode on the electron transport layer, wherein the hole injection layer comprises a compound represented by Chemical Formula 1:

Chemical Formula 1

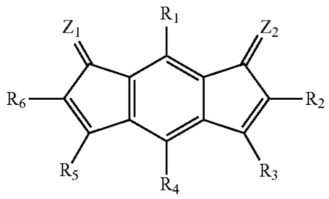

where $R_1$ to $R_6$ each independently represents one among a hydrogen atom, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted alkyl group with 1 to 12 carbon atoms, a substituted or unsubstituted alkoxy group with 1 to 12 carbon atoms, a substituted or unsubstituted ether group with 2 to 12 carbon atoms, a cyano group, a fluorine group, a trifluoromethyl group, a trifluoromethoxy group, and a trimethylsilyl group, and at least one among $R_1$ to $R_6$ comprises a cyano group, and $Z_1$ and $Z_2$ are independently represented by the following Chemical Formula 2:

Chemical Formula 2

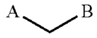

where A and B independently represent one among a hydrogen atom, a substituted or unsubstituted aryl group with 6 to 12 carbon atoms, a substituted or unsubstituted heteroaryl group with 1 to 12 carbon atoms and 1 to 4 heteroatoms one among O, N, S, and Si, a substituted or unsubstituted alkyl group with 1 to 12 carbon atoms, a substituted or unsubstituted alkoxy group with 1 to 12 carbon atoms, a substituted or unsubstituted ether group with 2 to 12 carbon atoms, a cyano group, a fluorine group, a trifluoromethyl group, a trifluoromethoxy group, and a trimethylsilyl group, wherein $Z_1$ and $Z_2$ are attached via a double bond between a carbon atom bound to A and B of Chemical Formula 2 and the indacene ring of Chemical Formula 1.

30. The organic light emitting display device of claim 29, wherein a substituent of the substituted aryl group, the substituted heteroaryl group, the substituted alkyl group, the substituted alkoxy group, or the substituted ether group includes an alkyl with 2 to 12 carbon atoms, an aryl with 6 to 15 carbon atoms, a hetero alkyl with 1 to 15 carbon atoms and 1 to 4 heteroatoms one among O, N, S, and Si, a cyano group, a fluorine group, a trifluoromethyl group, a trifluoromethoxy group, or a trimethylsilyl group.

31. The organic light emitting display device of claim 29, wherein the compound represented by Chemical Formula 1 is one among the following compounds:

B1

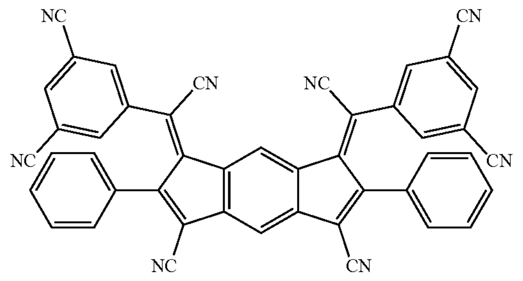

B2

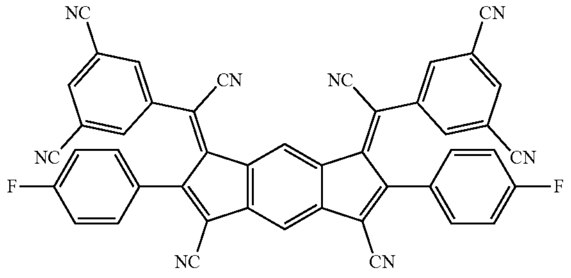

B3

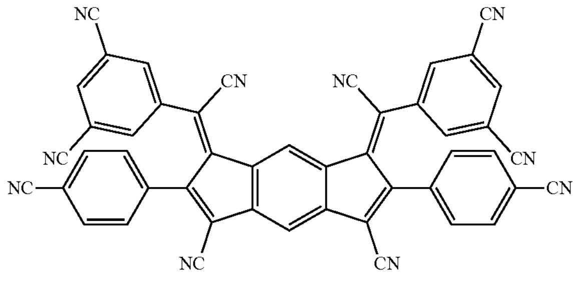

B4

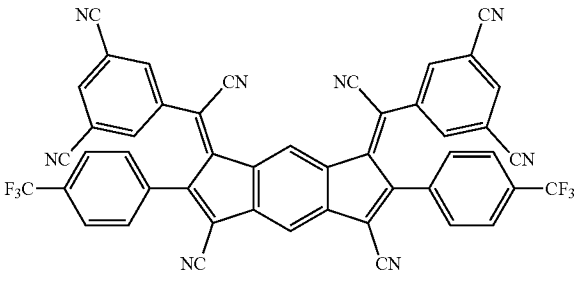

-continued

B5

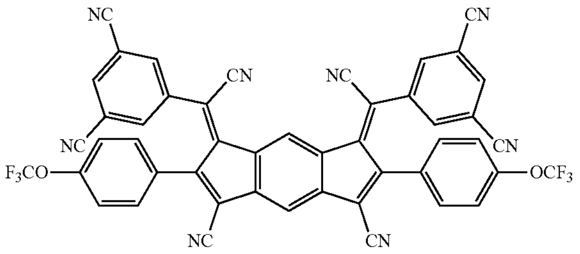

B6

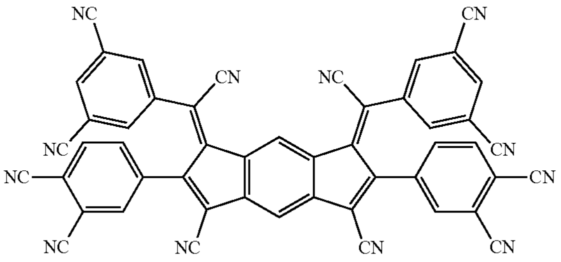

B7

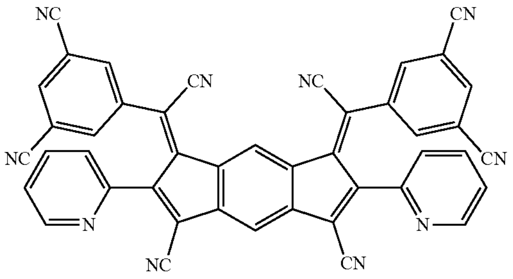

B8

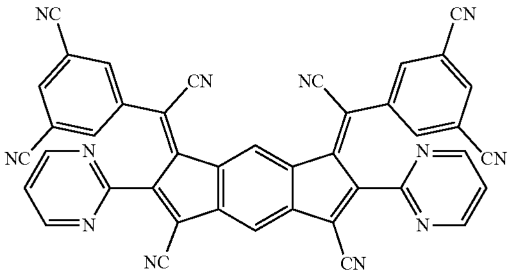

B9

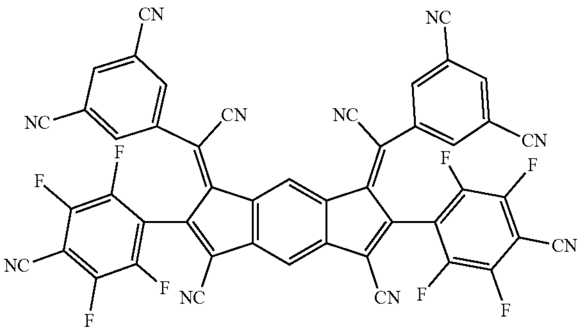

-continued
B10
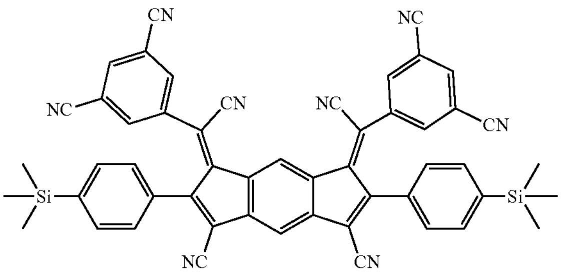
B11
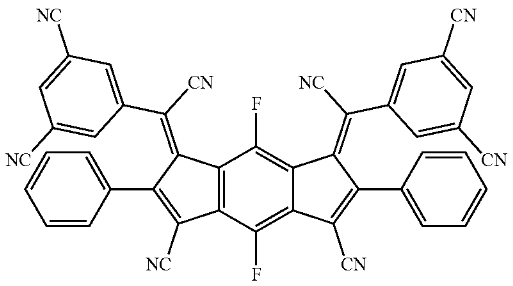
B12
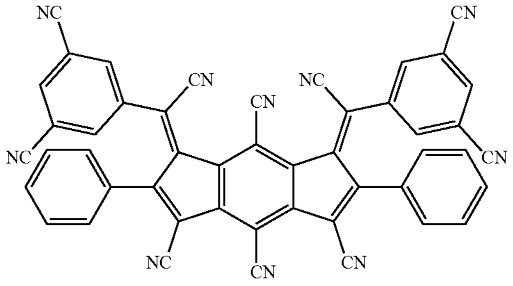
B13
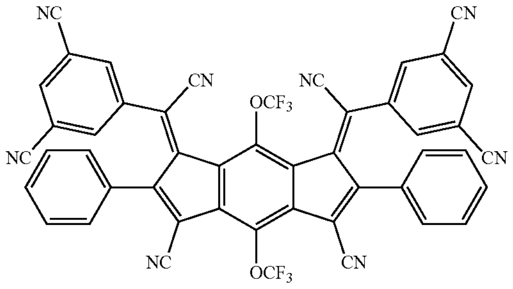
B14
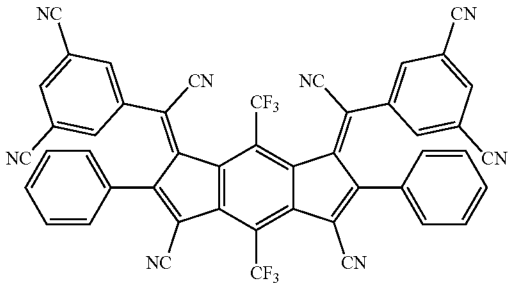
-continued
B15
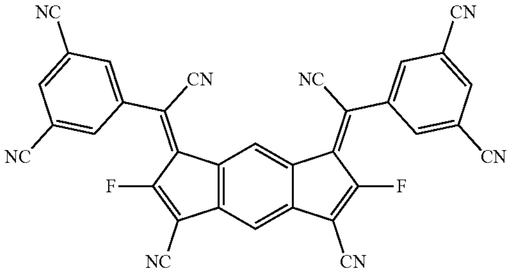
B16
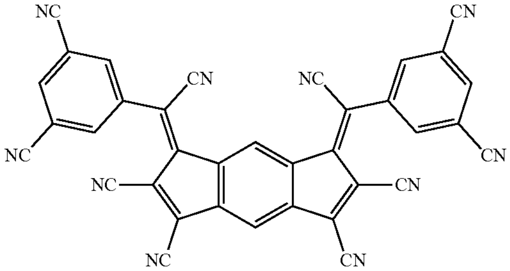
B17
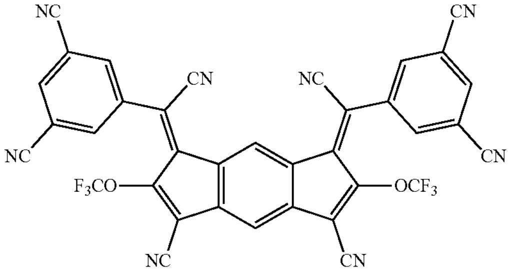
B18
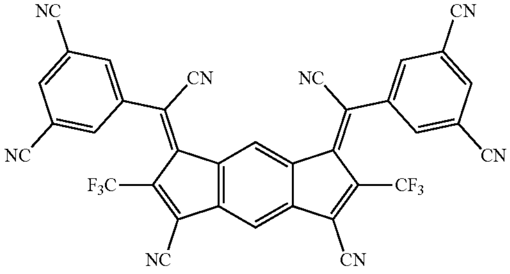
B19
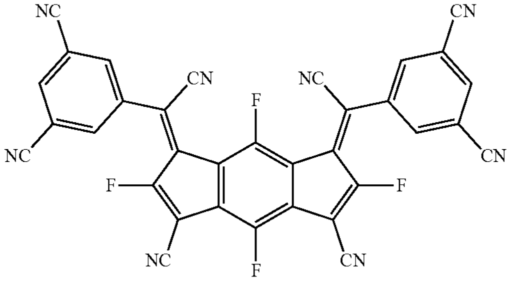

-continued
B20
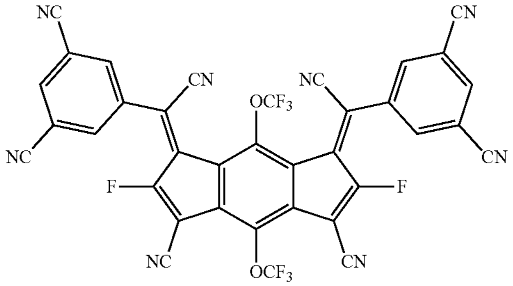
B21
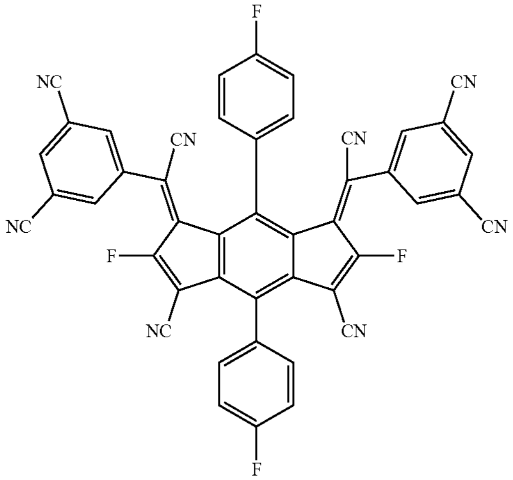
B22
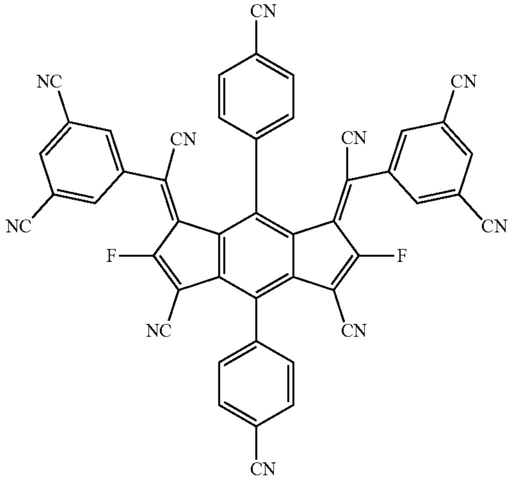
-continued
B23
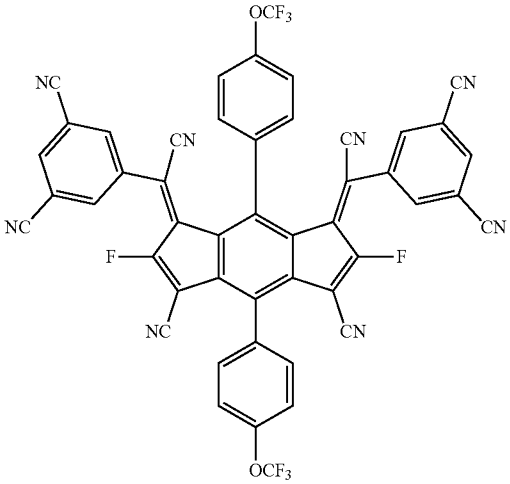
B24
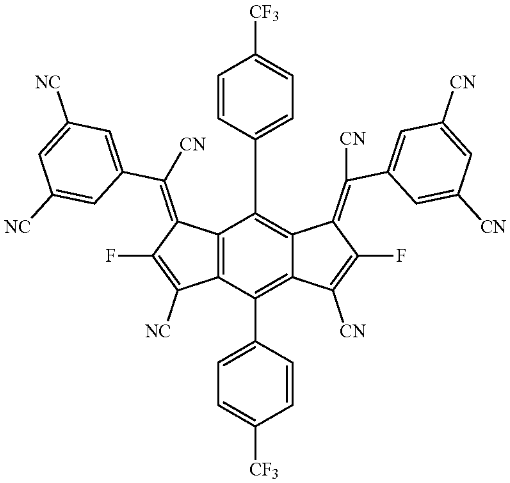
B25
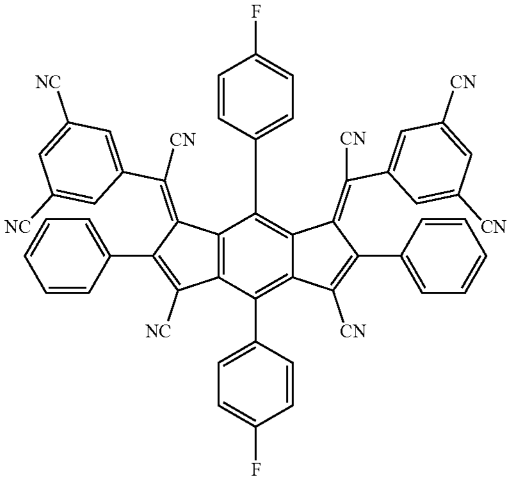

-continued
B26
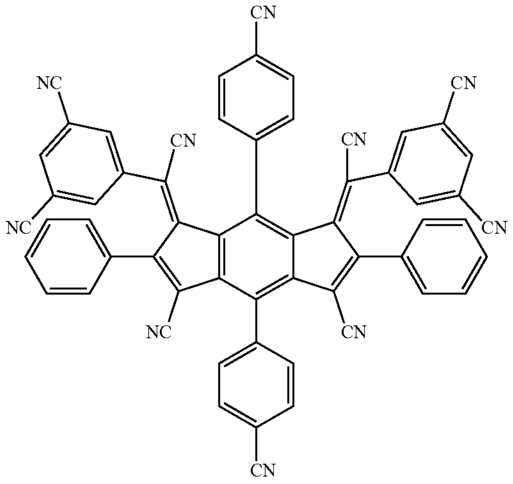
B27
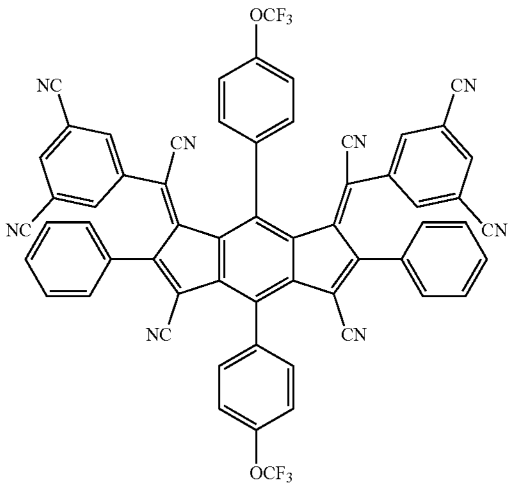
B28
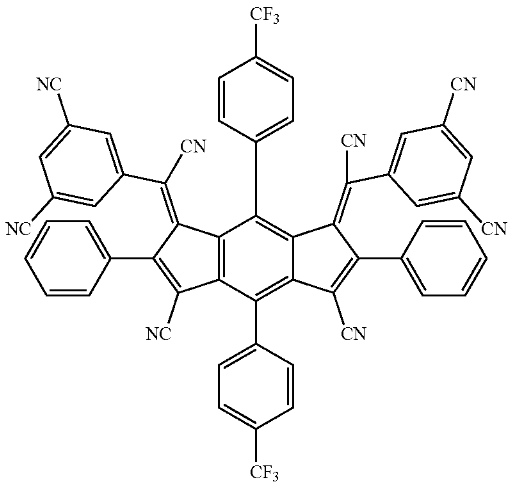
-continued
B29
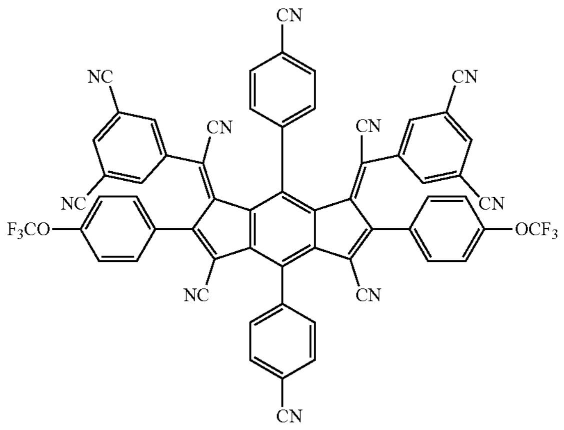
B30
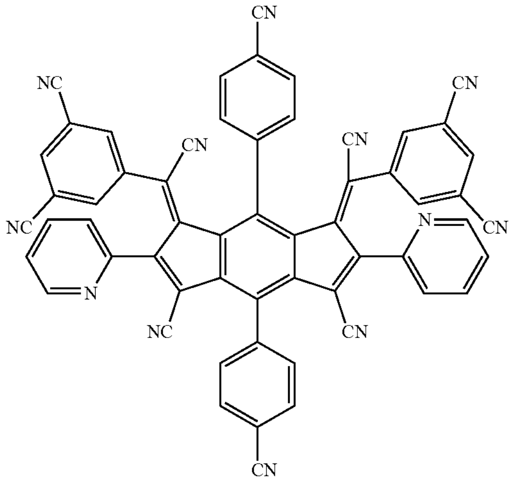
B31
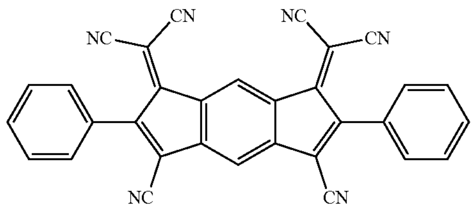
B32
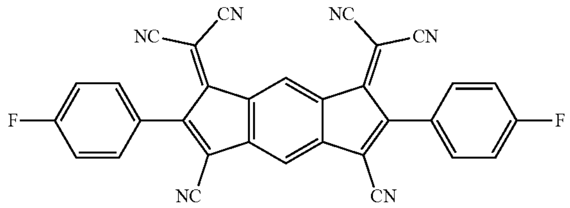
B33
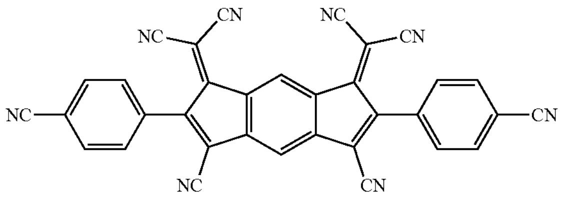

-continued
B34
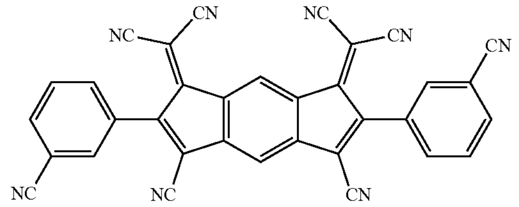
B35
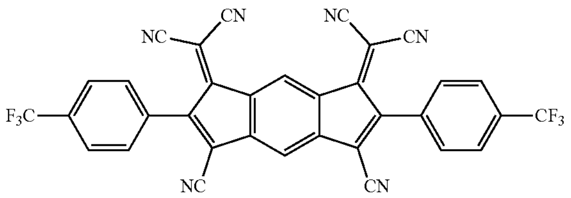
B36
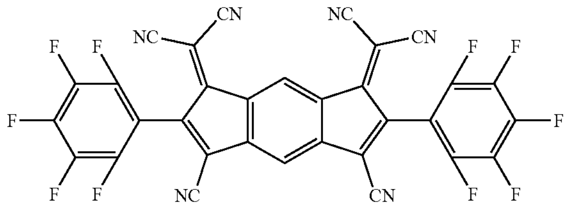
B37
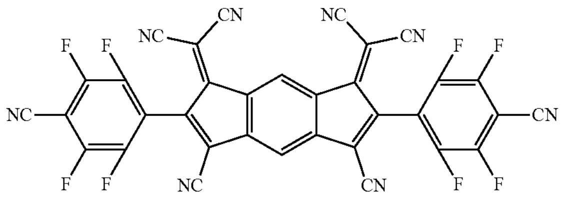
B38
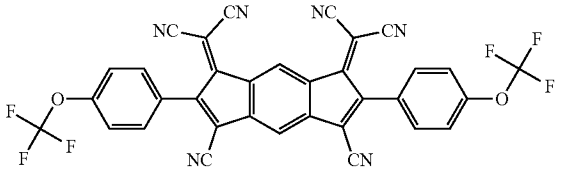
B39
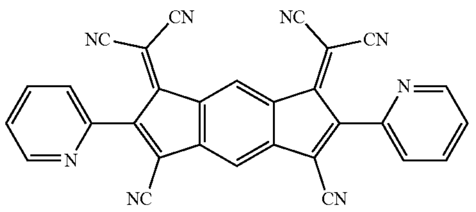
B40
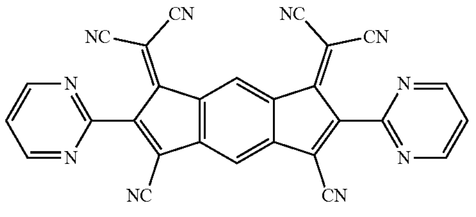
-continued
B41
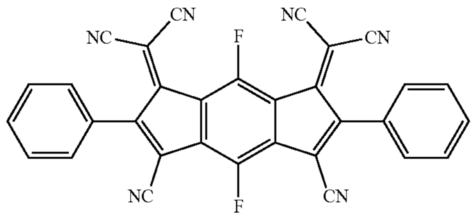
B42
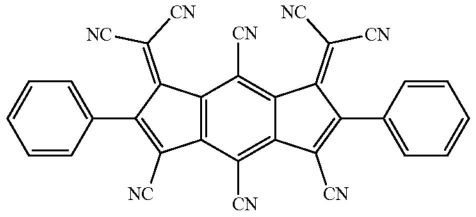
B43
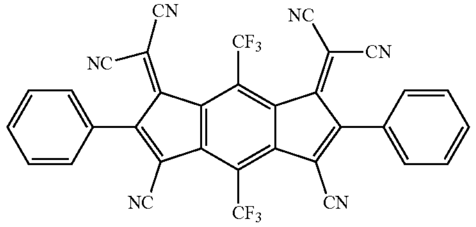
B44
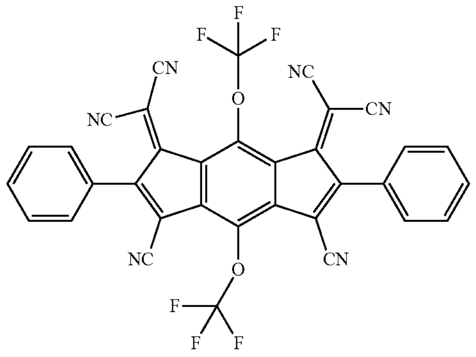
B45
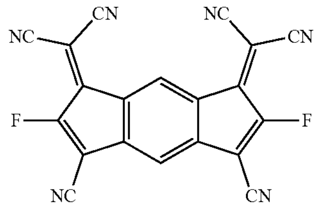
B46
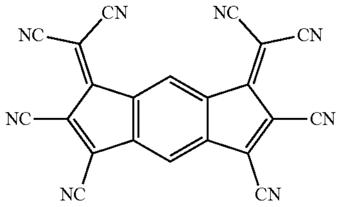

-continued
B47
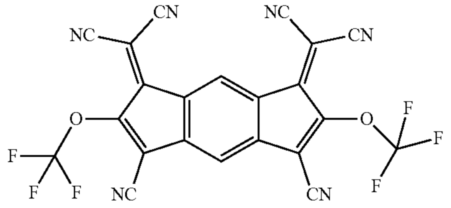
B48
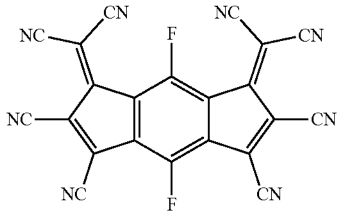
B49
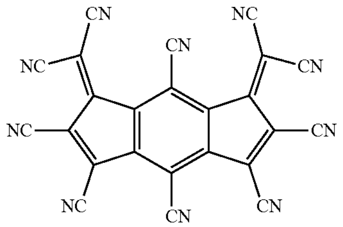
B50
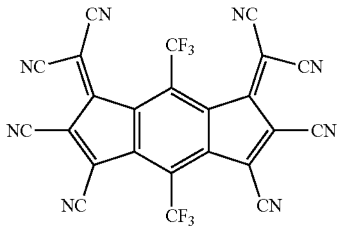
B51
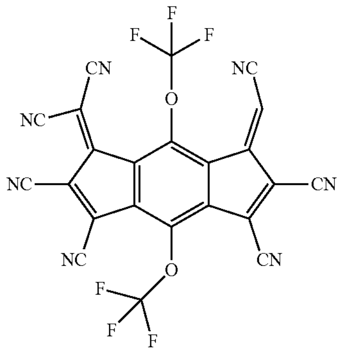
B52
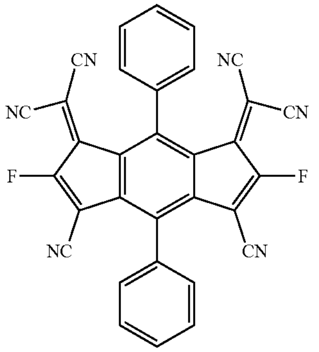
-continued
B53
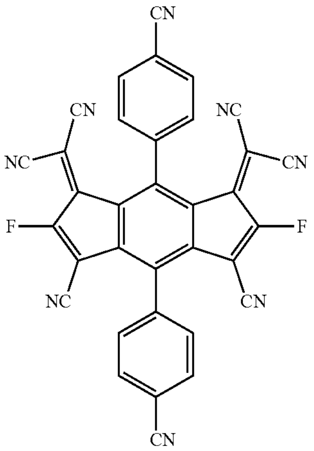
B54
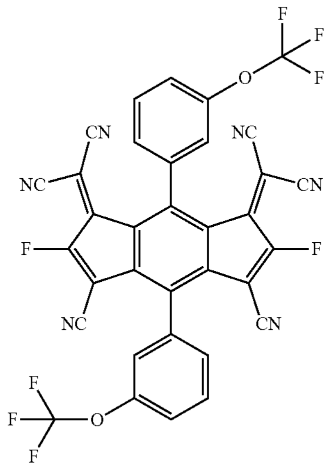
B55
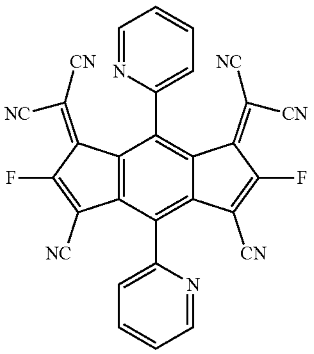
B56
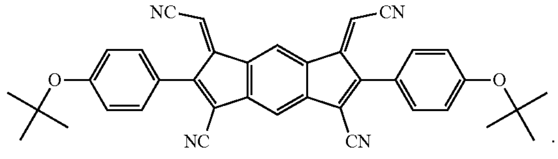
32. The organic light emitting display device of claim 31, wherein the hole injection layer includes the compound.
33. The organic light emitting display device of claim 29, further comprising an electron injection layer on the electron transport layer.

34. The organic light emitting display device of claim 29, wherein the light emitting layer emits light of a color of at least one among red, green, and blue.

* * * * *